US006551618B2

(12) United States Patent
Baird et al.

(10) Patent No.: US 6,551,618 B2
(45) Date of Patent: Apr. 22, 2003

(54) COMPOSITIONS AND METHODS FOR DELIVERY OF AGENTS FOR NEURONAL REGENERATION AND SURVIVAL

(75) Inventors: Andrew Baird, San Diego, CA (US); Ana Maria Gonzalez, San Diego, CA (US); Ann Logan, Worcester (GB); Martin Berry, Birmingham (GB)

(73) Assignees: University of Birmingham, Birmingham (GB); King's College, London (GB); Selective Genetics, Inc., San Diego, CA (US)

( * ) Notice: Subject to any disclaimer, the term of this patent is extended or adjusted under 35 U.S.C. 154(b) by 0 days.

(21) Appl. No.: 09/178,286

(22) Filed: Oct. 23, 1998

(65) Prior Publication Data

US 2002/0168338 A1 Nov. 14, 2002

Related U.S. Application Data

(63) Continuation-in-part of application No. 09/088,419, filed on Jun. 1, 1998, now abandoned, which is a continuation-in-part of application No. 08/805,381, filed on Feb. 24, 1997, now abandoned, and a continuation-in-part of application No. 08/805,382, filed on Feb. 24, 1997, now abandoned, and a continuation-in-part of application No. 08/805,383, filed on Feb. 24, 1997, now abandoned, and a continuation-in-part of application No. 08/718,904, filed on Sep. 24, 1996, now Pat. No. 6,037,329, which is a continuation-in-part of application No. 08/441,979, filed on May 16, 1995, now abandoned, which is a continuation-in-part of application No. 08/213,446, filed on Mar. 15, 1994, now abandoned, and a continuation-in-part of application No. 08/213,447, filed on Mar. 15, 1994, now abandoned, and a continuation-in-part of application No. 08/297,961, filed on Aug. 29, 1994, now abandoned, and a continuation-in-part of application No. 08/305,771, filed on Sep. 13, 1994, now abandoned.

(51) Int. Cl.$^7$ .......................... A61K 9/14; A61K 48/00
(52) U.S. Cl. ...................... 424/484; 424/468; 424/469; 424/486; 435/320.1; 435/91.4; 435/455; 514/44
(58) Field of Search ............................ 514/44; 424/93.2, 424/423, 424, 425, 468, 469, 484, 486, 143.1; 435/320.1, 91.4, 455; 536/24.5, 24.1, 24.2

(56) References Cited

U.S. PATENT DOCUMENTS

| 3,277,033 A | 10/1966 | Ugi |
| 3,839,297 A | 10/1974 | Wasserman et al. |
| 3,956,044 A | 5/1976 | Bowen et al. |
| 4,044,126 A | 8/1977 | Cook et al. |
| 4,045,238 A | 8/1977 | Battista et al. |
| 4,137,921 A | 2/1979 | Okuzumi et al. |
| 4,166,800 A | 9/1979 | Fong |
| 4,181,983 A | 1/1980 | Kulkarni |
| 4,243,775 A | 1/1981 | Rosensaft et al. |
| 4,279,249 A | 7/1981 | Vert et al. |
| 4,300,565 A | 11/1981 | Rosensaft et al. |
| 4,328,803 A | 5/1982 | Pape |
| 4,364,923 A | 12/1982 | Cook et al. |
| 4,374,234 A | 2/1983 | Stricklen et al. |
| 4,384,975 A | 5/1983 | Fong |
| 4,390,519 A | 6/1983 | Sawyer |
| 4,409,332 A | 10/1983 | Jefferies et al. |
| 4,414,209 A | 11/1983 | Cook et al. |
| 4,455,256 A | 6/1984 | Urist |
| 4,468,382 A | 8/1984 | Bacha et al. |
| 4,472,840 A | 9/1984 | Jefferies |
| 4,497,796 A | 2/1985 | Salser et al. |
| 4,517,295 A | 5/1985 | Bracke et al. |
| 4,530,449 A | 7/1985 | Nozawa et al. |
| 4,534,958 A | 8/1985 | Adams et al. |
| 4,538,603 A | 9/1985 | Pawelchak et al. |

(List continued on next page.)

FOREIGN PATENT DOCUMENTS

| DE | 42 19626 A1 | 12/1993 |
| EP | 466 222 A2 | 1/1992 |
| EP | 488 196 A2 | 6/1992 |
| EP | 614 974 A2 | 9/1994 |
| EP | 372 031 B1 | 9/1996 |
| GB | 2194241 | 3/1988 |
| GB | 2216891 | 10/1989 |
| WO | WO 85/03508 | 8/1985 |
| WO | WO 92/59904 | 3/1988 |
| WO | WO 88/05077 | 7/1988 |
| WO | WO 89/00198 | 1/1989 |
| WO | WO 89/04836 | 6/1989 |
| WO | WO 89/10962 | 11/1989 |
| WO | WO 90/00563 | 1/1990 |
| WO | WO 90/01870 | 3/1990 |
| WO | WO 90/02800 | 3/1990 |
| WO | WO 90/03733 | 4/1990 |
| WO | WO 90/05522 | 5/1990 |

(List continued on next page.)

OTHER PUBLICATIONS

US 5,182,365, 1/1993, Oppermann et al. (withdrawn)
Beer et al., Advanced Drug delivery Reviews, 27, 59–66, 1997.*

(List continued on next page.)

*Primary Examiner*—Dave T. Nguyen
(74) *Attorney, Agent, or Firm*—Seed Intellectual Property Law Group PLLC

(57) ABSTRACT

Devices useful in the delivery of DNA encoding neurotrophic agents, anti-fibrotic agents, and related compositions are disclosed herein for use in the treatment of central and/or peripheral nervous system injury. Methods of making and using the disclosed devices and DNA are also described. In various embodiments, the invention also discloses compositions and devices that may further include a targeting agent, such as a polypeptide that is reactive with an FGF receptor (e.g., bFGF), or another ligand that binds to cell surface receptors on neuronal cells, or a support cell. The invention also discloses methods of promoting neuronal survival and regeneration via transfection of an axon as it grows through a device or composition of the present invention, or via transfection of a repair cell.

44 Claims, 7 Drawing Sheets

U.S. PATENT DOCUMENTS

| | | |
|---|---|---|
| 4,539,981 A | 9/1985 | Tunc |
| 4,563,350 A | 1/1986 | Nathan et al. |
| 4,563,489 A | 1/1986 | Urist |
| 4,568,559 A | 2/1986 | Nuwayser et al. |
| 4,578,384 A | 3/1986 | Hollinger |
| 4,585,797 A | 4/1986 | Cioca |
| 4,591,501 A | 5/1986 | Cioca |
| 4,596,574 A | 6/1986 | Urist |
| 4,619,989 A | 10/1986 | Urist |
| 4,623,588 A | 11/1986 | Nuwayser et al. |
| 4,665,913 A | 5/1987 | L'Esperance, Jr. |
| 4,670,393 A | 6/1987 | Seeburg |
| 4,703,108 A | 10/1987 | Silver et al. |
| 4,711,783 A | 12/1987 | Huc et al. |
| 4,719,179 A | 1/1988 | Barany |
| 4,732,148 A | 3/1988 | L'Esperance, Jr. |
| 4,741,337 A | 5/1988 | Smith et al. |
| 4,743,679 A | 5/1988 | Cohen et al. |
| 4,744,365 A | 5/1988 | Kaplan et al. |
| 4,745,051 A | 5/1988 | Smith et al. |
| 4,757,013 A | 7/1988 | Inouye et al. |
| 4,761,471 A | 8/1988 | Urist |
| 4,776,890 A | 10/1988 | Chu |
| 4,780,313 A | 10/1988 | Koichiro et al. |
| 4,786,079 A | 11/1988 | Gospodarowicz et al. |
| 4,789,663 A | 12/1988 | Wallace et al. |
| 4,789,732 A | 12/1988 | Urist |
| 4,795,804 A | 1/1989 | Urist |
| 4,798,786 A | 1/1989 | Tice et al. |
| 4,798,886 A | 1/1989 | Kato et al. |
| 4,806,523 A | 2/1989 | Bentz et al. |
| 4,818,542 A | 4/1989 | DeLuca et al. |
| 4,820,631 A | 4/1989 | Lacal et al. |
| 4,833,125 A | 5/1989 | Neer et al. |
| 4,837,285 A | 6/1989 | Berg et al. |
| 4,839,130 A | 6/1989 | Kaplan et al. |
| 4,844,854 A | 7/1989 | Kaplan et al. |
| 4,846,172 A | 7/1989 | Berlin |
| 4,849,350 A | 7/1989 | Yoshio et al. |
| 4,856,513 A | 8/1989 | Muller |
| 4,865,846 A | 9/1989 | Kaufman |
| 4,868,113 A | 9/1989 | Jaye et al. |
| 4,870,009 A | 9/1989 | Evans et al. |
| 4,877,029 A * | 10/1989 | Valentini et al. ............ 128/334 |
| 4,877,864 A | 10/1989 | Wang et al. |
| 4,882,150 A | 11/1989 | Kaufman |
| 4,884,854 A | 12/1989 | Joffe |
| 4,889,119 A | 12/1989 | Jamiolkowski et al. |
| 4,898,186 A | 2/1990 | Ikada et al. |
| 4,898,734 A | 2/1990 | Mathiowitz et al. |
| 4,902,508 A | 2/1990 | Badylak et al. |
| 4,914,027 A | 4/1990 | Knapp et al. .............. 435/69.6 |
| 4,916,193 A | 4/1990 | Tang et al. |
| 4,916,793 A | 4/1990 | Kuhn |
| 4,920,143 A | 4/1990 | Levy et al. ................. 514/410 |
| 4,938,763 A | 7/1990 | Dunn et al. |
| 4,941,093 A | 7/1990 | Marshall et al. ....... 364/413.01 |
| 4,946,450 A | 8/1990 | Erwin |
| 4,952,402 A | 8/1990 | Sparks et al. |
| 4,952,496 A | 8/1990 | Studier et al. ................ 435/91 |
| 4,956,178 A | 9/1990 | Badylak et al. |
| 4,956,455 A | 9/1990 | Esch et al. .................. 530/399 |
| 4,957,902 A | 9/1990 | Grinnell |
| 4,961,707 A | 10/1990 | Magnusson et al. |
| 4,962,188 A | 10/1990 | Frankel ...................... 530/389 |
| 4,968,590 A | 11/1990 | Kuberasampath et al. |
| 4,968,715 A | 11/1990 | Dougherty et al. ......... 514/410 |
| 4,975,278 A | 12/1990 | Senter et al. .............. 424/94.3 |
| 4,975,526 A | 12/1990 | Kuberasamputh et al. |
| 4,975,527 A | 12/1990 | Koezuka et al. |
| 4,988,358 A | 1/1991 | Eppley et al. |
| 4,994,559 A | 2/1991 | Moscatelli et al. ......... 530/399 |
| 5,001,169 A | 3/1991 | Nathan et al. |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,019,087 A * | 5/1991 | Nichols ...................... 606/152 |
| 5,026,839 A | 6/1991 | Moscatelli et al. ........... 536/27 |
| 5,028,594 A | 7/1991 | Carson ........................ 514/23 |
| 5,035,893 A | 7/1991 | Shioya et al. |
| 5,037,744 A | 8/1991 | Knapp et al. |
| 5,037,749 A | 8/1991 | Findlay |
| 5,039,660 A | 8/1991 | Leonard et al. |
| 5,051,272 A | 9/1991 | Hermes et al. |
| 5,053,423 A | 10/1991 | Liu |
| 5,059,123 A | 10/1991 | Jernberg |
| 5,077,049 A | 12/1991 | Dunn et al. |
| 5,080,665 A | 1/1992 | Jarrett et al. |
| 5,081,106 A | 1/1992 | Bentley et al. |
| 5,084,051 A | 1/1992 | Törmälä et al. |
| 5,087,616 A | 2/1992 | Meyers et al. |
| 5,087,617 A | 2/1992 | Smith |
| 5,087,636 A | 2/1992 | Jamieson et al. |
| 5,093,246 A | 3/1992 | Cech et al. |
| 5,093,349 A | 3/1992 | Pandey et al. |
| 5,100,784 A | 3/1992 | Latta et al. |
| 5,103,840 A | 4/1992 | Kavoussi |
| 5,106,626 A | 4/1992 | Parsons et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,108,922 A | 4/1992 | Wang et al. |
| 5,109,016 A | 4/1992 | Dixon et al. |
| 5,109,124 A | 4/1992 | Ramachandran et al. |
| 5,110,604 A | 5/1992 | Chu et al. |
| 5,116,738 A | 5/1992 | Wang et al. |
| 5,116,742 A | 5/1992 | Cech et al. |
| 5,116,753 A | 5/1992 | Beattie et al. |
| 5,116,868 A | 5/1992 | Chen et al. |
| 5,118,667 A | 6/1992 | Adams et al. |
| 5,120,322 A | 6/1992 | Davis et al. |
| 5,120,715 A | 6/1992 | Kato et al. |
| 5,122,368 A | 6/1992 | Greenfield et al. |
| 5,122,463 A | 6/1992 | Varshavsky et al. |
| 5,124,155 A | 6/1992 | Reich |
| 5,126,323 A | 6/1992 | Rogers et al. |
| 5,128,136 A | 7/1992 | Bentley et al. |
| 5,128,326 A | 7/1992 | Balazs et al. |
| 5,133,708 A | 7/1992 | Smith |
| 5,133,755 A | 7/1992 | Brekke |
| 5,135,917 A | 8/1992 | Burch |
| 5,137,669 A | 8/1992 | Leonard et al. |
| 5,141,905 A | 8/1992 | Rosen et al. |
| 5,143,730 A | 9/1992 | Fues et al. |
| 5,144,019 A | 9/1992 | Rossi et al. |
| 5,149,691 A | 9/1992 | Rutherford |
| 5,149,708 A | 9/1992 | Dolphin et al. |
| 5,149,782 A | 9/1992 | Chang et al. |
| 5,155,214 A | 10/1992 | Baird et al. |
| 5,155,217 A | 10/1992 | Goldfarb et al. |
| 5,162,114 A | 11/1992 | Kuberasampath et al. |
| 5,162,430 A | 11/1992 | Rhee et al. |
| 5,164,368 A | 11/1992 | Recker |
| 5,165,952 A | 11/1992 | Solomon et al. |
| 5,166,058 A | 11/1992 | Wang et al. |
| 5,166,320 A | 11/1992 | Wu et al. |
| 5,168,050 A | 12/1992 | Hammonds, Jr. et al. |

| | | | | | | |
|---|---|---|---|---|---|---|
| 5,168,053 A | 12/1992 | Altman et al. | | 5,268,178 A | 12/1993 | Calhoun et al. |
| 5,169,784 A | 12/1992 | Summers et al. | | 5,270,300 A * | 12/1993 | Hunziker ..................... 514/12 |
| 5,169,933 A | 12/1992 | Anderson et al. | | 5,271,961 A | 12/1993 | Mathiowitz et al. |
| 5,171,217 A | 12/1992 | March et al. | | 5,272,262 A | 12/1993 | Rossi et al. |
| 5,171,574 A | 12/1992 | Kuberasampath et al. | | 5,273,056 A | 12/1993 | Mclaughlin et al. |
| 5,171,579 A | 12/1992 | Ron et al. | | 5,273,751 A | 12/1993 | Dubroff |
| 5,171,670 A | 12/1992 | Kronenberg et al. | | 5,273,964 A | 12/1993 | Lemons |
| 5,171,749 A | 12/1992 | Levy et al. | | 5,275,826 A | 1/1994 | Badylak et al. |
| 5,173,403 A | 12/1992 | Tang et al. | | 5,278,050 A | 1/1994 | Summers |
| 5,175,147 A | 12/1992 | Folkman et al. | | 5,278,126 A | 1/1994 | Katano et al. |
| 5,175,269 A | 12/1992 | Stavrianopoulos | | 5,278,201 A | 1/1994 | Dunn et al. |
| 5,176,996 A | 1/1993 | Hogan et al. | | 5,278,202 A | 1/1994 | Dunn et al. |
| 5,180,818 A | 1/1993 | Cech et al. | | 5,281,419 A | 1/1994 | Tuan et al. |
| 5,185,152 A | 2/1993 | Peyman | | 5,281,422 A | 1/1994 | Badylak et al. |
| 5,187,076 A | 2/1993 | Wozney et al. | | 5,282,851 A | 2/1994 | Jacob-labarre |
| 5,187,153 A | 2/1993 | Cordell et al. | | 5,286,634 A | 2/1994 | Stadler et al. |
| 5,187,261 A | 2/1993 | Latta et al. | | 5,288,496 A | 2/1994 | Lewis |
| 5,190,931 A | 3/1993 | Inouye | | 5,288,735 A | 2/1994 | Trager et al. |
| 5,191,067 A | 3/1993 | Lappi et al. | | 5,292,362 A | 3/1994 | Bass et al. |
| 5,192,741 A | 3/1993 | Orsolini et al. | | 5,292,802 A | 3/1994 | Rhee et al. |
| 5,192,788 A | 3/1993 | Dixon et al. | | 5,298,422 A | 3/1994 | Schwartz et al. |
| 5,196,185 A | 3/1993 | Silver et al. | | 5,304,121 A | 4/1994 | Sahatjian |
| 5,197,977 A | 3/1993 | Hoffman, Jr. et al. | | 5,306,303 A | 4/1994 | Lynch |
| 5,202,317 A | 4/1993 | Bruice | | 5,308,622 A | 5/1994 | Casscells et al. |
| 5,204,254 A | 4/1993 | Schmid et al. | | 5,308,623 A | 5/1994 | Fues et al. |
| 5,206,028 A | 4/1993 | Li | | 5,308,889 A | 5/1994 | Rhee et al. |
| 5,208,041 A | 5/1993 | Sindrey | | 5,317,010 A | 5/1994 | Pang et al. |
| 5,208,219 A | 5/1993 | Ogawa et al. | | 5,320,624 A | 6/1994 | Kaplan et al. |
| 5,212,058 A | 5/1993 | Baker et al. | | 5,324,307 A | 6/1994 | Jarrett et al. |
| 5,212,286 A | 5/1993 | Lewicki et al. | | 5,324,519 A | 6/1994 | Dunn et al. |
| 5,214,080 A | 5/1993 | Iwamura et al. | | 5,324,520 A | 6/1994 | Dunn et al. |
| 5,215,907 A | 6/1993 | Tang et al. | | 5,324,775 A | 6/1994 | Rhee et al. |
| 5,217,966 A | 6/1993 | Bruice | | 5,324,819 A | 6/1994 | Oppermann et al. |
| 5,218,088 A | 6/1993 | Gorenstein et al. | | 5,326,350 A | 7/1994 | Li |
| 5,220,013 A | 6/1993 | Ponte et al. | | 5,326,357 A | 7/1994 | Kandel |
| 5,223,263 A | 6/1993 | Hostetler et al. | | 5,328,955 A | 7/1994 | Rhee et al. |
| 5,223,483 A | 6/1993 | Thomas et al. | | 5,344,654 A | 9/1994 | Rueger et al. |
| 5,227,157 A | 7/1993 | McGinity et al. | | 5,350,580 A | 9/1994 | Muchow et al. |
| 5,229,127 A | 7/1993 | Mckinzie | | 5,352,463 A | 10/1994 | Badylak et al. |
| 5,229,273 A | 7/1993 | Gottesman et al. | | 5,354,557 A | 10/1994 | Oppermann et al. |
| 5,229,279 A | 7/1993 | Peoples et al. | | 5,354,844 A | 10/1994 | Beug et al. |
| 5,234,829 A | 8/1993 | Brown | | 5,360,610 A | 11/1994 | Tice et al. |
| 5,236,828 A | 8/1993 | Papas et al. | | 5,366,508 A | 11/1994 | Brekke ........................ 623/16 |
| 5,237,016 A | 8/1993 | Ghosh et al. | | 5,366,733 A | 11/1994 | Brizzolara et al. |
| 5,238,925 A | 8/1993 | Bentley | | 5,366,734 A | 11/1994 | Hutchinson |
| 5,238,940 A | 8/1993 | Liu et al. | | 5,366,875 A | 11/1994 | Wozney et al. |
| 5,241,049 A | 8/1993 | Goodman et al. | | 5,372,821 A | 12/1994 | Badylak et al. |
| 5,242,687 A | 9/1993 | Tykocinski et al. | | 5,374,431 A | 12/1994 | Pang et al. |
| 5,243,041 A | 9/1993 | Fernandez-pol | | 5,376,636 A | 12/1994 | Rutherford et al. |
| 5,244,797 A | 9/1993 | Kotewicz et al. | | 5,378,451 A | 1/1995 | Gorman et al. |
| 5,244,805 A | 9/1993 | Miller | | 5,378,540 A | 1/1995 | Olson |
| 5,248,608 A | 9/1993 | Van Dooren et al. | | 5,399,677 A | 3/1995 | Wolfman et al. |
| 5,250,296 A | 10/1993 | Ootsu | | 5,416,017 A | 5/1995 | Burton et al. |
| 5,250,302 A | 10/1993 | Oppermann et al. | | 5,445,833 A | 8/1995 | Badylak et al. |
| 5,250,584 A | 10/1993 | Ikada et al. | | 5,459,047 A | 10/1995 | Wozney et al. |
| 5,252,319 A | 10/1993 | Babcock et al. | | 5,460,831 A | 10/1995 | Kossovsky et al. |
| 5,252,720 A | 10/1993 | Sessler et al. | | 5,464,650 A | 11/1995 | Berg et al. |
| 5,252,725 A | 10/1993 | Rubin et al. | | 5,470,829 A | 11/1995 | Prisell et al. |
| 5,256,408 A | 10/1993 | Babcock et al. | | 5,474,797 A | 12/1995 | Sioshansi et al. |
| 5,256,769 A | 10/1993 | Kato et al. | | 5,494,806 A | 2/1996 | Segre et al. |
| 5,257,970 A | 11/1993 | Dougherty | | 5,496,552 A | 3/1996 | Kuberasampath et al. |
| 5,258,494 A | 11/1993 | Oppermann et al. | | 5,516,533 A | 5/1996 | Badylak et al. |
| 5,258,498 A | 11/1993 | Huston et al. | | 5,521,291 A | 5/1996 | Curiel et al. |
| 5,260,223 A | 11/1993 | Brenner et al. | | 5,543,394 A | 8/1996 | Wozney et al. |
| 5,262,178 A | 11/1993 | Malfroy Camine et al. | | 5,565,334 A | 10/1996 | Kufe et al. |
| 5,263,985 A | 11/1993 | Bao et al. | | 5,574,142 A | 11/1996 | Meyer et al. |
| 5,263,992 A | 11/1993 | Guire | | 5,589,466 A | 12/1996 | Felgner et al. |
| 5,264,618 A | 11/1993 | Felgner et al. | | 5,593,974 A | 1/1997 | Rosenberg et al. |
| 5,266,317 A | 11/1993 | Tomalski et al. | | 5,618,924 A | 4/1997 | Wang et al. |
| 5,266,465 A | 11/1993 | Rubin et al. | | 5,631,142 A | 5/1997 | Wang et al. |
| 5,266,683 A | 11/1993 | Oppermann et al. | | 5,635,372 A | 6/1997 | Celeste et al. |

| | | | |
|---|---|---|---|
| 5,635,373 A | 6/1997 | Wozney et al. | |
| 5,635,383 A | 6/1997 | Wu et al. | |
| 5,637,480 A | 6/1997 | Celeste et al. | |
| 5,639,638 A | 6/1997 | Wozney et al. | |
| 5,641,518 A | 6/1997 | Badylak et al. | |
| 5,652,118 A | 7/1997 | Ozkaynak et al. | |
| 5,652,337 A | 7/1997 | Oppermann et al. | |
| 5,656,593 A | 8/1997 | Kuberasampath et al. | |
| 5,658,882 A | 8/1997 | Celeste et al. | |
| 5,661,007 A | 8/1997 | Wozney et al. | |
| 5,661,025 A | 8/1997 | Szoka et al. | |
| 5,670,336 A | 9/1997 | Oppermann et al. | |
| 5,674,703 A | 10/1997 | Woo et al. | |
| 5,674,844 A | 10/1997 | Kuberasampath et al. | |
| 5,679,637 A | 10/1997 | Lappi et al. | |
| 5,688,678 A | 11/1997 | Hewick et al. | |
| 5,695,998 A | 12/1997 | Badylak et al. | |
| 5,698,531 A | 12/1997 | Nabel et al. | |
| 5,700,774 A | 12/1997 | Hattersley et al. | |
| 5,700,911 A | 12/1997 | Wozney et al. | |
| 5,703,043 A | 12/1997 | Celeste et al. | |
| 5,707,969 A * | 1/1998 | Nabel et al. | 514/44 |
| 5,723,119 A | 3/1998 | Schwarz et al. | |
| 5,763,416 A * | 6/1998 | Bonadio et al. | 514/44 |
| 5,770,580 A | 6/1998 | Ledley et al. | |
| 5,783,558 A | 7/1998 | Duvos et al. | |
| 5,792,751 A * | 8/1998 | Ledley et al. | 514/44 |
| 5,830,686 A | 11/1998 | Henderson | |
| 5,837,510 A | 11/1998 | Goldsmith et al. | |
| 5,843,776 A | 12/1998 | Tamaoki et al. | |
| 5,922,339 A * | 7/1999 | Usala | 424/424 |
| 5,962,427 A * | 10/1999 | Goldstein et al. | 514/44 |
| 6,040,172 A * | 3/2000 | Kaplitt | 435/320.1 |
| 6,060,247 A * | 5/2000 | Miller et al. | 435/6 |
| 6,087,171 A * | 7/2000 | Neuman et al. | 435/375 |
| 6,096,716 A * | 8/2000 | Hayes et al. | 514/44 |
| 6,106,824 A * | 8/2000 | Kaplitt et al. | 424/93.2 |
| 6,106,826 A * | 8/2000 | Brandt et al. | 424/93.2 |

FOREIGN PATENT DOCUMENTS

| | | |
|---|---|---|
| WO | WO 90/06321 | 6/1990 |
| WO | WO 90/08771 | 8/1990 |
| WO | WO 90/11092 | 10/1990 |
| WO | WO 90/12597 | 11/1990 |
| WO | WO 90/13649 | 11/1990 |
| WO | WO 90/14074 | 11/1990 |
| WO | WO 91/00916 | 1/1991 |
| WO | WO 91/02058 | 2/1991 |
| WO | WO 91/08483 | 6/1991 |
| WO | WO 91/15229 | 10/1991 |
| WO | WO 91/17424 | 11/1991 |
| WO | WO 91/18012 | 11/1991 |
| WO | WO 91/18099 | 11/1991 |
| WO | WO 91/18558 | 12/1991 |
| WO | WO 92/00999 | 1/1992 |
| WO | WO 92/04918 | 4/1992 |
| WO | WO 92/05199 | 4/1992 |
| WO | WO 92/06702 | 4/1992 |
| WO | WO 92/06705 | 4/1992 |
| WO | WO 92/07004 | 4/1992 |
| WO | WO 92/07573 | 5/1992 |
| WO | WO 92/11872 | 7/1992 |
| WO | WO 92/13948 | 8/1992 |
| WO | WO 92/15323 | 9/1992 |
| WO | WO 92/15676 | 9/1992 |
| WO | WO 92/17165 | 10/1992 |
| WO | WO 93/02192 | 2/1993 |
| WO | WO 93/03709 | 3/1993 |
| WO | WO 93/05751 | 4/1993 |
| WO | WO 93/09229 | 5/1993 |
| WO | WO 93/14778 | 8/1993 |
| WO | WO 93/15109 | 8/1993 |
| WO | WO 93/15608 | 8/1993 |
| WO | WO 93/16739 | 9/1993 |
| WO | WO 93/17669 | 9/1993 |
| WO | WO 93/19660 | 10/1993 |
| WO | WO 93/21969 | 11/1993 |
| WO | WO 93/25688 | 12/1993 |
| WO | WO 94/01139 | 1/1994 |
| WO | WO 94/01557 | 1/1994 |
| WO | WO 94/03600 | 2/1994 |
| WO | WO 94/04696 | 3/1994 |
| WO | WO 94/06399 | 3/1994 |
| WO | WO 94/06447 | 3/1994 |
| WO | WO 94/06449 | 3/1994 |
| WO | WO 94/10202 | 5/1994 |
| WO | WO 94/10203 | 5/1994 |
| WO | WO 94/20615 | 9/1994 |
| WO | WO 94/21679 | 9/1994 |
| WO | WO 94/23738 | * 10/1994 |
| WO | WO 94/25608 | 11/1994 |
| WO | WO 95/03831 | 2/1995 |
| WO | WO 95/18856 | 7/1995 |
| WO | WO 95/22611 | 8/1995 |
| WO | WO 95/22618 | 8/1995 |
| WO | WO 95/24928 | 9/1995 |
| WO | WO 95/24929 | * 9/1995 |
| WO | WO 95/28494 | 10/1995 |
| WO | WO 95/30003 | 11/1995 |
| WO | WO 95/33502 | 12/1995 |
| WO | WO 96/06641 | 3/1996 |
| WO | WO 96/07924 | 3/1996 |
| WO | WO 96/08274 | 3/1996 |
| WO | WO 96/13599 | 5/1996 |
| WO | WO 96/16668 | 6/1996 |
| WO | WO 97/11095 | 3/1997 |
| WO | WO 97/38729 | 10/1997 |
| WO | WO 99/53961 | 10/1999 |

OTHER PUBLICATIONS

Abdallah et al., Human Gene Therapy, 7: 1947–1954, 1996.*

Deglon et al., Human Gene Therapy, 7:2135–2146, 1996.*

Reynolds et al., Current Opinion in Biotechnology, 4:734–738, 1993.*

Branch, TIBS, 23, pp. 45–50, 1998.*

O'Malley, Jr. and Ledley, "Somatic Gene Therapy in Otolaryngology—Head and Neck Surgery," *Arch. Otolaryngol. Head Neck Surg.* 119:1191–1197, 1993.

Özkaynak et al., "Op–1 cDNA Encodes an Osteogenic Protein in the TFG–β Family," *EMBO J.* 9(7):2085–2093, 1990.

Paralkar et al., "Identification and Characterization of Cellular Binding Proteins (Receptors) for Recombinant Human Bone Morphogenetic Protein 2B, an Initiator of Bone Differentiation Cascade," *Proc. Natl. Acad. Sci. USA* 88:3397–3401, 1991.

Pereira et al., "Genomic Organization of the Sequence Coding for Fibrillin, the Defective Gene Product in Marfan Syndrome," *Human Molecular Genetics* 2(7) :961–968, 1993.

Rifkin, "TGF–β Formation; Mechanisms and Consequences," *J. Cellular Biochem.* Suppl. 19B, 3, 1995.

Roessier et al., "Adenoviral–Mediated Gene Transfer to Rabbit Synovium in Vivo," *J. Clin. Invest.* 92:1085–1092, 1993.

Rosen and Thies, "The BMP Proteins in Bone Formation and Repair," *Trends in Genetics* 8(3) :97–102, 1992.

Rosen et al., "Purification and Molecular Cloning of a Novel Group of BMPs and Localization of BMP mRNA in Developing Bone," *Connect. Tissue Res.* 20:313–319, 1989.

Sampath and Reddi, "Dissociative Extraction and Reconstitution of Extracellular Matrix Components Involved in Local Bone Differentiation," *Proc. Natl. Acad. Sci. USA.* 78(12):7599–7603, 1981.

Sampath et al., "In Vitro Transformation of Mesenchymal Cells Derived From Embryonic Muscle into Cartilage in Response to Extracellular Matrix Components of Bone," *Proc. Natl. Acad. Sci. USA* 81:3419–3423, 1984.

Sandusky, Jr., et al., "Histologic Findings After In Vivo Placement of Small Intestine Submucosal Vascular Grafts and Saphenous Vein Grafts in the Carotid Artery in Dogs," *Am. J. Pathol.* 140(2):317–324, 1992.

Seitz et al., "Effect of Transforming Growth Factor β on Parathyroid Hormone Receptor Binding and cAMP Formation in Rat Osteosarcoma Cells," *Journal of Bone and Mineral Research* 7:541–546, 1992.

Selander–Sunnerhagen et al., "How an Epidermal Growth Factor (EGF)–like Domain Binds Calcium," *The Journal of Biological Chemistry* 267(27):19642–19649, 1992.

Shimell et al., "The Drosophila Dorsal–Ventral Patterning Gene tolloid is Related to Human Bone Morphogenetic Protein 1," *Cell* 67:469–481, 1991.

Simons et al., "Antisense c–myb oligonucleotides inhibit intimal arterial smooth muscle cell accumulation in vivo," *Nature* 359:67–70, 1992.

Srivastava et al., "Construction of a Recombinant Human Parvovirus B19: Adenoassociated Virus 2 (AAV) DNA Inverted Terminal Repeats are Functional in an AAV–B19 Hybrid Virus," *Proc. Natl. Sci. USA* 86:8078–8082, 1989.

Steiner et al., "The New Enzymology of Precursor Processing Endoproteases," *The Journal of Biological Chemistry* 267(33):23435–23438, 1992.

Stratford–Perricaudet et al., "Widespread Long–term Gene Transfer to Mouse Skeletal Muscles and Heart," *J. Clin. Invest.* 90:626–630, 1992.

Sumner et al., "Enhancement of Bone Ingrowth by Transforming Growth Factor–β," *The Journal of Bone and Joint Surgery* 77-A(8):1135–1147, 1995.

Tamaki et al., "TGF–β1 in Glomerulosclerosis and Interstitial Fibrosis of Adriamycin Nephropathy," *Kidney International* 45:525–36, 1994.

Toriumi et al., "Mandibular Reconstruction With a Recombinant Bone–Inducing Factor," *Arch. Otolaryngol Head Neck Surg.* 117:1101–1112, 1991.

Ulmer et al., "Heterologous Protection Against Influenza by Injection of DNA Encoding a Viral Protein," *Science* 259:1745–1749, 1993.

Urist et al., "Bone Cell Differentiation and Growth Factors," *Science* 220:680–686, 1983.

Urist, "Bone: Formation by Autoinduction," *Science* 150:893–899, 1965.

Van Laethem et al., "Localization of Transforming Growth Factor β1 and Its Latent Binding Protein in Human Chronic Pancreatitis," *Gastroenterology* 108:1873–81, 1995.

Vilafranca et al., "Muscle Fibre Expression of Transforming Growth Factor–β1 and Latent Transforming Growth Factor–β Binding Protein in Canine Masticatory Muscle Myositis," *J. Comp. Pathol.* 112(3):299–306, 1995.

Waltenberger et al., "Induction of Transforming Growth Factor–β during Cardiac Allograft Rejection," *The Journal of Immunology* 151(2):1147–1157, 1993.

Waltenberger et al., "Involvement of Transforming Growth Factor–.beta. in the Formation of Fibrotic Lesions in Carcinoid Heart Disease," *American Journal of Pathology* 142(1):71–8, 1993.

Wang et al., "Recombinant Human Bone Morphogenetic Protein Induces Bone Formation," *Proc. Natl. Acad. Sci. USA* 87:2220–2224, 1990.

Wilson et al., "Somatic Gene Transfer in the Development of an Animal Model for Primary Hyperparathyroidism," *Endocrinology* 130(5):2947–2954, 1992.

Wolfe et al., "Conditions Affecting Direct Gene Transfer into Rodent Muscle In Vivo," *BioTechniques* 11(4):474–485, 1991.

Wolff et al., "Expression of Naked Plasmids by Cultured Myotubes and Entry of Plasmids into T Tubules and Caveolae of Mammalian Skeletal Muscle," *Journal of Cell Science* 103:1249–1259, 1992.

Wolff et al., "Direct Gene Transfer into Mouse Muscle in Vivo," *Science* 247:1465–1468, 1990.

Wozney et al., "Novel Regulators of Bone Formation: Molecular Clones and Activities," *Science*, 242:1528–1534, 1988.

Wu and Wu, "Receptor–Mediated Gene Delivery and Expression in Vivo," *The Journal of Biological Chemistry* 263(29):14621–14624, 1988.

Yasko et al., "The Healing of Segmental Bone Defects, Induced by Recombinant Human Bone Morphogenetic Protein (rhBMP–2)," *The Journal of Bone and Joint Surgery* 74-A(5):659–670, 1992.

Yin et al., "Molecular Cloning of a Novel Fibrillin–Like cDNA: Expression in Callus Tissue as Alternatively Spliced Transcripts," 40th Annual Meeting, Orthopaedic Research Society, Conference Abstract, Feb. 21–24, 1994.

Zhu et al., "Direct Gene Transfer into Regenerating Achilles' Tendon," 40th Annual Meeting, Orthopaedic Research Society, Conference Abstract, Feb. 21–24, 1994.

Abraham et al., "Heparin–Binding EGF–Like Growth Factor: Characterization of Rat and Mouse cDNA Clones, Protein Domain Conservation Across Species, and Transcript Expression in Tissues," *Biochemical and Biophysical Research Communications*, vol. 190 (Jan. 15, 1993).

Abraham et al., "Human Basic Fibroblast Growth Factor: Nucleotide Sequence, Genomic Organization, and Expression in Mammalian Cells," *Quant. Biol.* 51:657–668 (Sep. 1, 1986).

Abraham et. al., "Human basic fibroblast growth factor: nucleotide sequence and genomic organization," *EMBO J.* 5:2523–2528 (1986).

Agrawal et al., "Oligodeoxynucleoside Methylphosphonates: Synthesis and Enzymic Degradation," *Tetrehedron Lett.* 28(31):3539–3542 (1987).

American Academy of Ophthalmology, Basic and Clinical Science Course, Cornea Section 4, Retina and Vitreous, 1987–1988 Edition, pp. 72–73.

Azuma & Shearer, "Induction of Elongation in Cultured Rat Lens Epithelial Cells by FGF and Inhibition by Selenite," *Invest. Ophthal. & Vis. Sci.* 33(8):2528–2531 (1992).

Baird et al, *Recent Progress in Hormone Res.* 42:143–205 (1986).

Baird et al., "Angiogenic Factor in Human Ocular Fluid," *The Lancet*, Sep. 7, 1985, p. 563.

Baird et al., "Biological and chemical characterization of basis FGF–saporin mitoxin," *J. Cell Biol. Abstracts*, 11(5):173a, abstract #745, Thirtieth Annual Meeting, Dec. 9–13, 1990.

Baird et al., "Fibroblast growth factors," *British Med. Bull.* 45(2):438–452 (1989).

Baird et al., "Receptor– and heparin–binding domains of basic fibroblast growth factor," *P.N.A.S.* 85:2324–2328 (1988).

Baird et al., *The Lancet*, Sep. 7, 1985, p. 563.

Barbieri and Stirpe, "Ribosome–inactivating proteins from plants: Properties and possible uses," *Cancer Surveys* 1(3):490–520 (1982).

Barbieri et al., "Blood clearance and organ distribution and tissue concertration of native, homopolymerized and Ig–G–conjugated ribosome–inactivating proteins," *Xenobiotica* 20(12):1331–1341 (1990).

Barr et al., "Expression and processing of biologically active fibroblast growth factors in the yeast *Saccharomyces cerevisiae*," *J. Biol. Chem.* 263(31):16471–16478 (1988).

Barra et al., "Assessment of sequence features in internal regions of proteins," *Biotech. and Applied Biochem.* 13:48–53 (1991).

Batra et al., "Insertion of Constant Region of Domains of Human $IgG_1$ into CD4–PE40 Increases its Plasma Half–life," *Molecular Immunol.* 30(4):379–386 (1993).

Batra et al., "Single–Chain Immunotoxins Directed at the Human Transferrin Receptor Containing Psudomonas Exotoxin A or Diphtheria Toxin: Anti–TFR(Fv)–PE40 and DT388–Anti–TFR(Fv)," *Mol. Cell. Biol.* 11(4):2200–2205 (1991).

Baudouin et al., "Acidic Fibroblast Growth Factor Distribution in Normal Human Eye and Possible Implications in Ocular Pathogenesis," *Ophthalmic Res.* 22:73–81 (1990).

Bäumert et al., "RNA–Protein Neighbourhoods of the Ribosome Obtained by Crosslinking," *Eur. J. Biochem.* 89:353–359 (1978).

Beattie et al., "Functional Impact of Attachment and Purification in the Short Term Culture of Human Pancreatic Islets," *J. Clin. Endocrin. & Metabolism*, 73(1):93–98 (1991).

Beattie et al., "Selective elimination of fibroblasts from pancreatic islet monolayers by basic fibroblast growth factor–saporin mitoxin," *Diabetes* 39(8):1002–1005 (1990).

Beitz et al., "Antitumor activity of basic fibroblast growth factor–saporin mitoxin in vitro and in vivo," *Cancer Research* 52:227–230 (1992).

Benatti et al., "Nucleotide sequence of cDNA coding for saporin–6, a type–1 ribosome–inactivating protein from *Saponaria officinalis*," *Eur. J. Biochem.* 183:465–470 (1989).

Bernardi & Bernardi, "Completed sequence of pKG1800, a vector for determination of transcription terminators," *DNA Sequence* 1:147–150 (1990).

Better et al., "Expression of engineering antibodies and antibody fragments in microorganisms," *Methods in Enzymology* 178:476–496 (1989).

Bianchi & Viotti, "DNA methylation and tissue–specific transcription of the storage protein genes of maize," *Plant Mol. Biol* 11:203–214 (1988).

Bicknell, R., "Vascular targeting and the inhibition of angiogenesis," *Annals of Oncology* 5(suppl. 4):S45–S50 (1994).

Blanquet et al., "Identification and Isolation From Bovine Epithelial Lens Cells of Two Basic Fibroblast Growth Factor Receptors tht Possess bFGF–Enhanced Phosphorylation Activities," 160(3):1124–1131 (1989).

Brinkmann et al., "Independent domain folding of Pseudomas exotoxin and single–chain immunotoxins: Influence of interdomain connections," *Proc. Natl. Acad. Sci. USA* 89:3075–3079 (1992).

Brosius & Holy, "Regulation of ribosomal RNA promoters with a synthetic lac operator," *Proc. Natl. Acad. Sci.* 81:6929 (1984).

Buchner et al., "A Method of Increasing the Yield of Properly folded Recombinant fusion Proteins: Single–Chain Immunotoxins from Renaturation of Bacterial Inclusions bodies," *Anal. Biochem.* 205:263–270 (1992).

Carlsson et al., "N–Succinimidyl 3–(2–Pyridyldithio)propionate, a New Heterobifunctional Reagent," *Biochem. J.* 173:732–737 (1978).

Casscells et al., "Elimination of smooth muscle cells in experimental restenosis: Targeting of fibroblast growth factor receptors," *P.N.A.S.* 89:7159–7163 (1992).

Chandler et al., "Characterization of mitotoxins containing heparin–binding epidermal growth factor–like growth factor fused to saporin," *Biosis Database Abastract*: Abstract No. 95:186714 (1995).

Chaudhary et al., "Activity of recombinant fusion protein between transforming growth factor type and Pseudomonas toxin," *Proc. Natl. Acad. Sci. USA*, 84:4538–4542 (1987).

Chen et al., "A novel gene delivery system using EGF receptor–mediated endocytosis," *FEBS Letters* 338:167–169 (1994).

Chen et al., "Design of a genetic immunotoxin to eliminate toxin immunogenicity," *Gene Therapy* 2:116–123 (1995).

Cheng et al., "A versatile method of the coupling of protein to DNA: synthesis of $\alpha_2$–macroglobulin–DNA conjugates," *Nucleic Acids Res.* 11(3):659–669 (1983).

Chu et al., "Derivatization of unprotected polynucleotides," *Nucleic Acids Res.* 11(18)6513–6529 (1983).

Chu et al., "Synthesis of amplifiable report RNA for bioassays," *Nucleic Acids Res.* 14(14):559–603 (1986). (DIALOG™ Abstract provided).

Claffey et al., "Structural requirements for dimerization, glycosylation, secretion, and biological function of VPF/VEGF," *Medline Database*: Abstract #95110840 (1995).

Clusel et al., "Ex vivo regulation of specific gene expression by nanomolar concentration of double–stranded dumbbell oligonucleotides," *Nucl. Acids Res.* 21:3405–3411 (1993).

Coghlan, A., "Gene dream fades away," *New Scientist* Nov.: 14–15 (1995).

Conn et al., "Amino acid and cDNA sequences of a vascular endothelial cell mitogen that is homologous to platelet–derived growth factor," *Proc. Natl. Acad. Sci.* 87:2628–2632 (1990).

Courty et al., "Evidence for FGF–Like Growth Factor in Adult Bovine Retina: Analogies With EDGF I," 136(1):102–108 (1986).

Crystal, Science, vol. 270, 404–410 (1995).

Cumber et al., "Structural Features of the Antibody–A Chain Linkage that Influence the Activity and Stability of Ricin A Chain Immunotoxins," *Bioconjugate Chem.* 3:397–401 (1992).

Dabin & Courtois, "In vitro Kinetics of Basic Fibroblast Growth Factor Diffusion Across a Reconstituted Corneal Endothelium," *J. Cell. Physiology* 147:396–402 (1991).

Dang et al., "Identification of the Human c–myc Protein Nuclear Translocation Signal," *Mol. Cell. Biol.* 8:4049–4058 (1988).

Dang et al., "Nuclear and Nucleolar Targeting Sequences of c–erb–A, c–myb, N–myc, p53, HSP70, and HIV tat Proteins," *J. Biol. Chem.* 264:18019–18023 (1989).

Dauchel et al., "Modulation of Mitogenic Activity and Cellular Binding of Basic Fibroblast Growth Factor by Basic Proteins," *J. Cell. Biochem.* 39(4):411–420 (1989).

David et al., "Biphasic Effect of the Mitotoxin bFGF–Saporin on Bovine Lens Epithelial Cell Growth: Effect of Cell Density and Extracellular Matrix," *J. Cell. Physiology* 153:483–490 (1992).

Deonarain et al., *British J. Cancer 70* (5):786–94, 1994.

Dionne et al., *EMBO J.* 9:2658–2692 (1990).

Dranoff et al., *Advances in Immunology*, vol. 58:417–454 (1995).

Duester et al., "Fusion of the *Escherichia coli* $tRNA_1^{Leu}$ Promoter to the galK Gene: Analysis of Sequences Necessary for Growth–Rate–Dependent Regulation," *Cell* 30:855–864 (1982).

Duffaud et al., "Expression and secretion of foreign proteins in *Escherichia coli*," *Methods in Enzymology* 153:492–507 (1987).

Ebbecke et al., "Antiproliferatie effects of a c–myc antisense oligonucleotide on human arterial smooth muscle cells," *Basic Res. Cardiol.* 87:585–591 (1992).

Eckstein & Gish, "Phosphorothioates in molecular biology," *Trends Biol. Sci.* 14:97–100 (1989).

Eckstein, "Nucleoside Phosphorothioates," *Annu. Rev. Biochem.* 54:367–402 (1985).

Eriksson et al., "Three–dimensional structure of human basic fibroblast growth factor." *P.N.A.S.* 88:3441–3445 (1991).

Esch et al., "Primary structure of bovine brain acidic fibroblast growth factor (FGF)," *Biochem., and Biophys. Res. Comm.* 133(2):554–562 (1985).

Esch et al., "Primary structure of bovine pituitary basic fibroblast growth factor (FGF) and comparison with the amino–terminal sequence of bovine brain acidic FGF," *P.N.A.S.* 82:6507–6511 (1985).

Fattom et al., "Comparative Immunogenicity of Conjugates Composed of the *Staphylococcus aureus* Type 8 Capsular Polysaccharide Bound to Carreir Proteins by Adipic Acid Dihydrazide or N–Succinimidyl–3–(2–Pyridyldithio)propionate," *Invection & Immun.* 60(2):584–589 (1992).

Fattom et al., "Comparative Immunogenicity of Conjugates Composed of the *Staphyloccoccus aureus* Type 8 Caspular Polysaccharide Bound to Carrier Proteins by Adipic Acid Dihydrazide or N–Succinimidyl–3–(2–Pyridyldithio) propionate," *Infection and Immunity* 60(2):584–589 (1992).

Fen et al., "Structural Organization and Chromosomal Assignment of the Gene Encoding the Human Heparin–Binding Epidermal Growth Factor–like Growth Factor/Diphtheria Toxin Receptor," *Biochemistry* 32:7932–7938 (1993).

FitzGerald and Pastan, "Pseudomonas exotoxin: recombinant conjugates as therapeutic agents," *Endocytosis, Toxins, Immunotoxins and Viruses*, 20:731–734 (1992).

Folkman & Klagsburn, *Science* 235:442–447 (1987).

Fordham–Skelton et al., "Characterization of saporin genes: in vitro expression and ribosome inactivation," *Mol. Gen. Genet.* 229:460–466 (1991).

Fordham–Skelton et al., "Synthesis of saporin gene probes from partial protein sequence data: Use of inosine–oligonucleotides, genomic DNA and the polymerase chain reaction," *Mol. Gen. Genet.* 221:134–138 (1990).

Forsberg et al., "Thrombin and H64A Subtilisin Cleavage of Fusion Proteins for Preparation of Human Recombinant Parathyroid Hormone," *J. Protein Chem.* 10(5):517–526 (1991).

Fox et al., "Production, biological activity, and structure of recombinant basic fibroblast growth factor and an analog with cysteine replaced by serine," *J. Biol. Chem.* 263(34):18452–18458 (1988).

Fryling et al., "Chracterization of a Cellular Protease That Cleaves Pseudomonas Exotoxin," *Infection and Immunity* 60(2):497–502 (1992).

Gawlak et al., *Bioconj. Chem.* 4:483–489 (1993).

Gelfi et al., "Isoelectric focusing in immobilized pH gradients in the pH 10–11 range," *J. Biochem. and Biophys. Methods* 15:41–48 (1987).

Gilboa, *Seminars in Oncology*, vol. 23, 1:101–107 (1996).

Goldmacher et al., "Photoactivation of Toxin Conjugates," *Bioconj. Chem.* 3:104–107 (1992).

Goodchild, "Conjugates of Oligonucleotides and Modified Oligonucleotides: A Review of Their Synthesis and Properties," *Bioconjugate Chemistry* 1(3):166–186 (1990).

Gordon et al., "Topographical localization of the C–terminal region of the voltage–dependent sodium channel from *Electrophorus electricus* using antibodies raised against a synthetic peptide," *Proc. Natl. Acad. Sci. USA* 84:308–312 (1987).

Gospodarowicz et al., "Clonal growth of bovine vascular endothelial cells: Fibroblast growth factor as a survival agent," *Proc. Natl. Acad. Sci USA* 73:4120–4124 (1976).

Gospodarowicz et al., "Isolation of brain fibroblast growth factor by heparin–Sepharose affinity chromatography: Identity with pituitary fibroblast growth factor," *P.N.A.S.* 81:6963–6967 (1984).

Gospodarowicz et al., "Purification in High Yield of Brain Fibroblast Growth Factor by Preparative Isoelectric Focusing at pH 9.6," *J. Biol. Chem.* 257(20):12266–12276 (1982).

Gospodarowicz et al., "The Role of Fibroblast Grwoth Factor and Epidermal Growth Factor in the Proliferative Response of the Corneal and Lens Epithelium," *Exp. Eye Res.* 25:631–649 (1977).

Gottesman et al., "Transcription Antitermination by Bacteriophage Lambda N Gene Product," *J. Mol. Biol.* 140:57–75 (1980).

Goureau et al., "Differential regulation of inducible nitric oxide synthase by fibroblast growth factors and transforming growth factor in bovine retinal pigmented epithelial cells: Inverse correlation with cellular proliferation," *Proc. Natl. Acad. Sci. USA* 90:1–5 (1993).

Günzburg and Salmons, "Virus vector design in gene therapy," *Molecular Medicine Today* 4:410–417 (1995).

Habuka et al., "Expression and Secretion of Mirabilis Antiviral Protein in *E. coli* and its inhibition of in vitro Eukaryotic and Prokaryotic protein synthesis," *J. Biol. Chem.* 265(19):10988–10992 (1989).

Hartley et al., "Single–chain ribosome inactivating proteins from plants depurinate *Escherichia coli* 23S ribosomal RNA," *FEBS* 290(1,2):65–68 (1991).

Heistad et al., *Stroke*, 9:1688–93, Sep. 27, 1996.

Hertier and Frankel, "Immunotoxins: A clinical review of their use in the treatment of malignancies," *J. Clinical Oncology* 7(12):1932–1942 (1989).

Hoganson et al., "Comparison of the Effects of Three Different Toxin Genes and Their Levels of Expression on Cell Growth and Bystander Effect in Lung Adenocarcinoma," *Cancer Research* 56:1315–1323 (1996).

Huang et al., "Association of Bovine Brain–derived Growth Factor Receptor with Protein Tyrosine Kinase Activity," *J. Biol. Chem.* 261:9568–9571 (1986).

Imamura et al. *Biochem. Biophys. Res. Comm.* 155(2):583–590 (1988).

Jäger et al., "Oligonucleotide N–Alkylphosphoramidates: Synthesis and Binding to Polynucleotides," *Biochemistry* 27:7237–7246 (1988).

Javitt et al., "Increased Risk of Retinal Complications Associated with Nd:YAG Laser Capsulotomy," *Ophthalmology* 99(10):1487–1498 (1992).

Jaye et al., "Human Endothelial Cell Growth Factor: Cloning, Nucleotide Sequence, and Chromosome Localization," *Science* 233:541–545 (1986).

Johnson et al., *Advances in Cancer Res.* 60:1–41 (1993).

Johnson et al., *Mol. Cell. Biol.* 10:4728–4736 (1990).

Kataoka, "DNA sequence of Mirabilis Antiviral Protein (MAP), a ribosome–inactivating protein with an antiviral property, from Mirabilis jalapa L. and its expression in *Escherichia coli*," *J. Biol. Chem.* 266(13):8426–8430 (1991).

Kneib–Cordonier et al., "Orthogonal Solid–Phase Synthesis of Human Gastrin–I Under Mild Conditions," *Int. J. Pept. Protein Res.* 35(6)527–538 (1990) (Abstract only provided).

Kredich et al., p. 1157, in "The Metabolic Basis of Inherited Disease" (5th ed.), eds. Standbury et al., McGraw–Hill, New York (1983).

Kreitman et al., "Rational Design of a Chimeric Toxin: An Intramolecular Location for the Insertion of Transforming Growth Factor α withing Pseudomonas Exotoxin as a Targeting Ligand," *Bioconjugate Chem.* 3:58–62 (1992).

Kurokawa et al., "Nucleotide sequence of rat basic fibroblast growth factor cDNA," *Nucleic Acids Res.* 16(11):5201 (1998).

Lambert et al., "Immunotoxins containing single chain ribosome–inactivating proteins," *Cancer Treatment* 37:175–209 (1988).

Lambert et al., "Purified immunotoxins that are reactive with human lymphoid cells," *J. Biol. Chem.* 260(22):12035–12041 (1985).

Lappi and Baird, "Mitotoxins: Growth factor–targeted cytotoxic molecules," *Progress in Growth Factor Res.* 2:223–236 (1990).

Lappi et al., "Basic fibroblast growth factor in cells derived from Dupuytren's contracture: Synthesis, presence, and implications for treatment of the disease," *J. Hand Surgery* 17A(2):324–332 (1992).

Lappi et al., "Basic fibroblast growth factor–saporin mitotoxin: An endothelial cell growth inhibitor," 1990 UCLA Symposia Abstract, 19th Annual UCLA Symposia on Molecular and Cellular Biology, Keystone, Colorado, Apr. 6–12, 1990.

Lappi et al., "Characterization of a Saponaria officinalis seed rebosome–inactivating protein: Immunoreactivity and sequence homogies," *Biochem. and Biophys. Res. Comm.* 160(2):917–923 (1989).

Lappi et al., "Characterization of a Saponaria officinalis seed ribosome–inactivating protein: Immunoreactivity and sequence homologies," *Biochem. Biophys. Res. Commun.* 129(3):934–942 (1985).

Lappi et al., "The basic fibroblast growth factor–saporin mitotoxin acts through the basic fibroblast growth factor receptor," *J. Cell. Physio.* 147:17–26 (1991).

Lappi et al., "The disulfide bond connecting the chains of ricin," *P.N.A.S.* 75(3):1096–110 (1978).

Lappi, Douglas, *Anal. Biochem.* 212:446–451 (1993).

Leclerc et al., "Assessment [sic] of Restenosis vs. Primary Lesions in Patients With Peripheral Vascular Disease Using in Situ Hybridization and Gene Expression of Two Non-muscle Myosin Isoforms," *JACC* 17(2):105A (1991).

Ledley, F., "Nonviral Gene Therapy: The Promise of Genes as Pharmaceutical Products," *Human Gene Therapy* 6:1129–1144 (1995).

Lei et al., "Characterization of the *Erwinia carotovora* pelB Gene and Its Product Pectate Lyase," *J. Bacteriol.* 169(9):4379–4383 (1987).

Lindner et al., "Role of basic fibroblast growth factor in vascular lesion formation," *Circulation Research* 68(1):106–113 (1991).

Luckow et al., "Trends in the Development of Baculovirus Expression Vectors," *Bio/technology* 6:47–55 (1988).

Mahan et al., "Phase Change Enzyme Immunoassay," *Anal. Biochem.* 162:163–170 (1987).

Maras et al., "The amino acid sequence of a ribosome–inactivating protein from Saponaria officinalis seeds," *Biochem. Internatl.* 21(5):831–838 (1990).

Marshall et al., "Photo–ablative reprofiling of the cornea using an excimer laser: Photorefractive keratectomy," Cit. vol. I, *Lasers in Ophthalmology*, pp. 22–48, (1986).

Marucci et al., "In vivo effects in mice of an anti–t cell immunotoxin," *J. Immunology* 142:2955–2960 (1989).

Mascarelli et al., "Fibroblast growth factor phosphorylation and receptors in rod outer segments," *EMBO J.* 8(8):2265–2273 (1989).

Mastrangelo et al., "Gene Therapy for Human Cancer: An Essay for Clinicians," *Seminars in Oncology* 23(1):4–21 (1996).

McAvoy et al., "The Role of Fibroblast Growth Factor in Eye Lens Development," *Annals N.Y. Acad. Sci.,* pp. 256–274 (1991).

McKenney et al., pp. 383–415, in *Gene Amplification and Analysis 2: Analysis of Nucleic Acids by Enzymatic Methods*, Chirikjian et al. (Eds.), North Holland Publishing Co., Amsterdam (1981).

Melton et al., *J. Natl. Cancer Inst.* 88 (3/4):153–165, 1996.

Mesri et al., "Heparin–binding Transforming Growth Factor –Pseudomonas Exotoxin A. A Heparin Sulfate–Modulated Recombinant Toxin Cytotoxin to Cancer Cells and Proliferating Smooth Muscle Cells," *Journal of Biological Chemistry* 268(7):4853–4862 (1993).

Mesri et al., "The heparin–binding domain of heparin–binding EGF–like growth factor can target Pseudomonas exotoxin to kill cells exclusively through heparan sulfate proteoglycans," *Chemical Abstracts*: Abstract No. 121:271455 (1994).

Miller et al., "Syntheses and Properties of Adenine and Thymine Nucleoside Alkyl Phosphotriesters, the Neutral Analogs of Dinucleoside Monophosphates$^{1a-dn}$," *J. Am. Chem. Soc.* 93:6657–6665 (1971).

Millon et al., "Synthesis of a New Reagent, Ehtyl 4–azidobenzoylaminoacetimidate, and Its Use for RNA–Protein Cross–linking within *Escherichia coli* Ribosomal 30–S Subunits," *Eur. J. Biochem.* 110:485–492 (1980).

Mirate et al., "A simple technique for extracapsular lens extraction in the rabbit," *Current Eye Res.* 1(8):491–493 (1981).

Miyamoto et. al., "Molecular Cloning of a Novel Cytokine cDNA Encoding the Ninth Member of the Fibroblast Growth Factor Family, Which Has a Unique Secretion Property," *Mol. Cel. Biol.* 13:4251–4259 (1993).

Montecucchi et al., "N–terminal sequence of some ribosome–inactivating proteins," *Int. J. Peptide Protein Res.* 33:263–267 (1989).

Moody et al., "Regiospecific inhibition of DNA duplication by antisense phosphate–methylated oligodeoxynucleotides," *Nucl. Acids. Res.* 17(12):4769–4782 (1989).

Morton et al., "Colocalization of fibroblast growth factor binding sites with extracellular matrix components in normal and keratoconus corneas," *Current Eye Res.* 8(10):975–987 (1989).

Moscatelli, "High and low affinity binding sites for basic fibroblast growth factor on cultured cells: Absence of a role for low affinity binding in the stimulation of plasminogen activator production by bovine capillary endothelial cells," *J. Cell. Physiol.* 131:123–130 (1987).

Nakamura et al., "DNA Sequence of the Gene for the Outer Membrane Lipoprotein of *E. Coli*: an Exttremely AT–Rich Promoter," *Cel* 18:1109–1117 (1979).

Neufield et al., *J. Biol. Chem.* 261:5631–5637 (1986).

Neville et al., "Enhancement of Immunotoxin Efficacy by Acid–Cleavable Cross–Linking Agents Utilizing Diptheria Toxin and Toxin Mutants," *J. Biol. Chem.* 264(25):14653–14661 (1989).

Neville et al., "Enhancement of Immunotoxin Efficacy by Acid–Cleavable Cross–Linking Agents Utilizing Diphtheria Toxin and Toxin Mutants," *Journal of Biological Chemistry* 264(25):14653–14661 (1989) (Abstract only provided).

Ngo et al., "Computational Complexity, Protein Structure Prediction, and the Levinthal Paradox," in *The Protein Folding Problem and Tertiary Structure Prediction*, Merz and Le Grand (eds.), Birkhäuser Boston, 1994, pp. 491–495.

Ngo et al., "The protein folding problem and tertiary structure function," Birkhauser Boston Inc., 14, 491–495 (1994).

Nuefeld and Gospodarowicz, "The identification and partial characterization of the fibroblast growth factor receptor of baby hamster kidney cells," *J. Biol. Chem.* 260(25):13860–13868 (1985).

O'Hare et al., "Cytotoxicity of a recombinant ricin–A–chain fusion protein containing a proteolytically–cleavable spacer sequence," *FEBS* 273(1,2):200–204 (1990).

Oeltmann and Frankel, "Advances in immunotoxins," *FASEB J.* 5:2334–2337 (1991).

Oste & Brimacombe, "The Use of sym–Triazine Trichloride in RNA–Protein Cross–linking Studies with *Escherichia coli* Ribosomal Subunits," *Molec. Gen. Genet.* 168:81–86 (1979).

Partanen et al., "FGFR–4, a novel acidic fibroblast growth factor receptor with a distinct expression pattern," *EMBO J.* 10:1347–1354 (1991).

Petroutsos et al., "Comparison of the effects of EGF, pFGF and EDGF on corneal epithelium wound healing," *Current Eye Res.* 3(4):593–598 (1984).

Pettmann et al., "Biologically Active Basic Fibroblast Growth Factor Migrates at 27kD in 'Non–Denaturing' SDS–Polyacrylamide Gel Electrophoresis," *Growth Factors* 5:209–220 (1991).

Pötgens et al., "Covalent Dimerization of Vascular Permeability Factor/Vascular Endothelial Growth Factor Is Essential for Its Biological Activity. Evidence from CYS to SER Mutations," *Journal of Biological Chemistry* 269(52):32879–32885 (1994).

Prieto et al., "Expression and characterization of a basic fibroblast growth factor–saporin fusion protein in *Escherichia coli*," *Annals N.Y. Acad. Sci.* 538:434–437 (1991).

Prieto et al., "Expression and characterization of basic FGF–Saporin in *E. coli*," Abstract presented at the meetings, "The Fibroblast Growth Factor Family," La Jolla, California, Jan. 16–18 and the 20th UCLA Symposia on Molecular and Cellular Biology, Keystone, Colorado, Apr. 1–7, 1991.

Puri et al., "In Vitro and in vivo Suppression of Interleukin–2–Activated Kiler Cell Activity by Chimeric Proteins between Interleukin–2 and Pseudomonas Exotoxin," *Cell. Immunol.* 143:3240334 (1992).

Rieck et al., "Recombinant Human Basic Fibroblast Growth Factor (Rh–bFGF) in Three Different Wound Models in Rabbits: Corneal Wound Healing Effect and Pharmacology," *Exp. Eye Res.* 54:987–998 (1992).

Rinke et al., "The Use of Azidoarylimidoesters in RNA–Protein Cross–linking Studies With *Escherichia coli* Ribosomes," *J. Mol. Biol.* 137:301–314 (1980).

Riordan et al., "Identification of the Cystic Fibrosis Gene: Cloning and Characterization of Complementary DNA," *Science* 245:1066–1073 (1989).

Rosenberg et al., "Vectors for selective expression of cloned DNAs by T7 RNA polymerase," *Gene* 56:125:135 (1987).

Schwarz et al., "Nucleotide sequence of cro, cll and part of the O gene in page DNA," *Nature* 272:410–413 (1978).

Seetharam et al., "Increased Cytotoxic Activity of Pseudomonas Exotoxin and Two Chimeric Toxins Ending in DKEL," *J. Biol. Chem.* 266:17376–17381 (1991).

Seno et al., "Stabilizing basic fibroblast growth factor using protein engineering," *Biochem. and Biophys. Res. Comm.* 151(2):701–708 (1933).

Shimasaki et al., "Complementary DNA cloning and sequencing of rat ovarian basic fibroblast growth factor and tissue distribution study of its mRNA," *Bioch. Bioph. Res. Comm.* 157(1):256–263 (1988). (DIALOG™ Abstract provided).

Siegall et al., "Cytotoxic activity of chimeric proteins composed of acidic fibroblast growth factor and Pseudomonas exotoxin on a variety of cell types," *FASEB* 5:2843–2849 (1991).

Siegall et al., *Bioconj. Chem.* 5:77–83 (1994).

Siena et al., "Synthesis and characterization of an antihuman T–lymphocyte saporin immunotoxin (OKT1–SAP) with in vivo stability into nonhuman primates," *Blood* 72(2):756–765 (1988).

Simons et al., "Antisense Nonmuscle Myosin heavy Chain and c–myb Oligonucleotides Suppress Smooth Muscle Cell Proliferation In Vitro," *Circ. Res.* 70(4):835–843 (1992).

Sivalingam et al., "Basic Fibroblast Growth Factor Levels in the Vitreous of Patients with Proliferative Diabetic Retinopathy," *Arch Ophthalamol* 108:869 (1990).

Soria, M., "Immunotoxins, ligand–toxin conjugates and molecular targeting," *Pharm. Res.* 21(Supp. 2):35–46 (1989).

Sosnowski et al., "Receptor Mediated Gene Delivery Through the FGF Receptor: Applications in the Eye," *Investigative Ophthalmology & Visual Science* 37(3):S187, Abstract No. 885, 1996.

Sosnowski et al., "Targeting DNA through fibroblast growth factor receptors," *Proceedings of the American Association for Cancer Research* 37:426, Abstract No. 2991, 1996.

Sperling & Sperling, "Photochemical cross–linking of histones to DNA in nucleosomes," *Nucl. Acids. Res.* 5:2755–2773 (1978).

Stec et al., "Synthesis and Absolute Configuration of P–Chiral O–Isopropyl Oligonucleotide Triesters," *Tetrehedron Lett.* 26:2191–2194 (1985).

Stirpe et al. "Ribosome–inactivating proteins from the seeds of *Saponaria officinalis* L. (soapwort), of *Agrostemma githago* L. (corn cockle) and of *Asparagus officinalis* L. (asparagus), and from the latex of *Hura crepitans* L. (sandbox tree)," *Biochem. J.* 216:617–625 (1983).

Studer et al., "Influence of a Peptide Linker on Biodistribution and Metabolism of Antibody–Conjugated Benzyl–EDTA. Comparison of Enzymatic Digestion in Vitro and in Vivo," *Bioconjugate Chem.* 3(5):424–429 (1992).

Studier & Moffatt, "Use of Bacteriophage T7 RNA Polymerase to Direct Selective High–level Expression of Cloned Genes," *J. Mol. Biol.* 189:113–130 (1986).

Studier et al., "Use of T7 RNA Polymerase to Direct Expression of Cloned Genes," *Meth. Enzymol.* 185:60–89 (1990).

Sullenger et al., "Tethering Ribozymes to a Retroviral Packaging Signal for Destruction of Viral RNA," *Science* 262:1566–1569 (1993).

Takahashi et al., *Biochem. Biophys. Res. Commun.* 177:1–7 (1991).

Tanaka et al., "Cloning and characterization of an androgen–induced growth factor essential for the androgen–dependent growth of mouse mammary carcinoma cells," *Proc. Natl. Acad. Sci USA* 89(19):8928–32 (1992). (DIALOG™ Abstract provided).

Tazzari et al., "Ber–H2 (anti–CD30)–saporin immunotoxin: a new tool for the [sic] treatment of Hodgkin's disease and CD30+ lymphoma: in vitro evaluation," *Brit. J. Haematology* 81:203–211 (1992).

Theuer et al., "A Recombinant Form of Pseudomonas Exotoxin directed at the Epidermal Growth Factor Receptor That is Cytotoxic without Requiring Proteolytic Processing," *J. Biol. Chem.* 267(24):16872–16877 (1992).

Thevenin et al., "A novel photoactivatable cross–linker for the functionally–directed region–specific fluorescent labeling of proteins," *Eur. J. Biochem.* 207:471–477 (1992).

Thierry et al., "In vitro and in vivo inhibition of tumorigenicity of neoplastic Kaposi's sarcoma cell line (KS Y–1) by lipsomal IL–6, IL–8 and VEGF antisense oligodeoxynucleotides," *Biosis Database:* Abstract #95:186644 (1995).

Thompson and Fiddes, "Chemical characterization of the cysteines of basic fibroblast growth factor," *Annal N.Y. Acad. Sci* 638:78–88 (1991).

Thompson et al., "Characterization of Sequences within Heparin–binding EFG–like Growth Factor That Mediate Interaction with Heparin," *Journal of Biological Chemistry* 269(4):2541–2549 (1994).

Thorpe et al., *Cancer Res.* 47, 592–5931, (1987).

Thorpe et al., "Citotoxicity acquired by conjugation of an anti–Thy$_{1.1}$ monoclonal antibody and the ribosome–inactivating protein, gelonin," *Eur. J. Biochem.* 116:447–454 (1981).

Thorpe et al., "New Coupling Agents for the Synthesis of Immunotoxins Containing a Hindered Disulfide Bond with Improved Stability in Vivo," *Cancer Res.* 47:5924–5931 (1987).

Tripathi et al., "Fibroblast growth factor in the eye and prospects for its therapeutic use,"—excerpts, pp. 230–237, *Drug Dev. Res.* 19:225–237 (1990a).

Tripathi et al., "Growth Factors in the Aqueous Humor and Their Therapeutic Implications in Glaucoma and Anterior Segment Disorders of the Human Eye," *Drug Dev. Res.* 22:1–23 (1991).

Trokel et al., "Excimer Laser Surgery of the Cornea," *Amer. J. Ophthalmology* 96:710–715 (1983).

Trouet et al., "A covalent linkage between daunorubicin and proteins that is stable in serum and reversible by lysosomal hydrolases, as required for a lysosomotropic drug–carrier conjugate: In vitro and in vivo studies," *Proc. Natl. Acad. Sci. USA* 79:626–629 (1982).

Vanin et al., "p–Azodophenylglyoxal: A Heterobifunctional Photosensitive Reagent," *FEBS Lett.* 124(1):89–92 (1981).

Victor et al., "Characterization of human vascular endothelial growth factor mitotoxins," *Biosis Database*: Abstract #95:186713 (1995).

Vieira & Messing, "Production of Single–Stranded Plasmid DNA," *Meth. Enzymol.* 15:3–11 (1987).

Vieira & Messing, "The pUC plasmids, and M13mp7–derived system for insertion mutagenesis and sequencing with synthetic universal primers," *Gene* 19:259–268 (1982).

Vile et al., *Molecular Medicine Today*, vol. 4, 2:B4–82 (1992).

von Heijne, "Signal sequences: the limits of variation," *J. Mol. Biol.* 184:99–105 (1985).

Wagner et al., "Transferrin–polycation conjugates as carriers for DNA uptake into cells," *Proc. Natl. Acad. Sci. USA* 87:3410–3414 (1990).

Walden et al., "Major Histocompatiblity Complex–Restricted and Unrestricted Activation of Helper T Cell Lines by Liposome–Bound Antigens," *J. Mol. Cell Immunol.* 2:191–197 (1986).

Wawryznczak et al., "Molecular and biological properties of an abrin A chain immunotoxin designed for therapy of human small cell lung cancer," *Br. J. Cancer* 66:361–366 (1992).

Wellhöner et al., "Uptake and Concentration of Bioactive Macromolecules by K562 Cells vial the Transferrin Cycle Utilizing and Acid–labile Transferrin Conjugate," *J. Biol. Chem.* 266:4309–4314 (1991).

Westby et al., "Preparation and Characterization of Recombinant Proricin Containing an Alternative Protease–Sensitive Linker Sequence," *Bioconjugate Chem.* 3:3745–381 (1992).

Yang et al., "Cloning of cDNA for human VEGF and its high–efficiency expression in *E. coli.*," *Chemical Abstracts:* Abstract #120:316874 (1993).

Yanisch–Perron et al., "Improved M13 phase cloning vectors and host strains: Nucleotide sequences of the M13mp18 and UC19 vectors," *Gene* 33:103–119 (1985).

Yen et al., "Synthesis of water–soluble copolymers containing photocleavable bonds," *Makromol. Chem.* 190:69–82 (1989).

Zenke et al., "Receptor–mediated endocytosis of transferrin–polycation conjugates: An efficient way to introduce DNA into hematopoietic cells," *Proc. Natl. Acad. Sci. USA* 87:3655–3659 (1990).

Zhang et al., "Three–dimensional structure of human basic fibroblast growth factor, a structural homolog of interleukin 1," *P.N.A.S.* 88:3446–3450 (1991).

Berry et al., "Targeted Neurotrophin Gene Transfer to Retinal Ganglion Cells In Vivo Using Gene Activated Matrices," *Society for Neuroscience Abstracts* 24(1–2), p. 1309, 1989.

Logan et al., "Neuroprotection and Neuroregeneration in the Central Nervous System (CNS) by Targeted Neurotrophin Gene Transfer," *Journal of Endocrinology* 156(Supp.), p. OC17, 1998.

Abstract of DE 42 19 626 A1, Dec. 23, 1993.

Agarwala and Gay, "Specific Binding of Parathyroid Hormone to Living Osteoclasts," *J. Bone Miner. Res.* 7:531–539, 1992.

Alper, "Boning Up: Newly Isolated Proteins Heal Bad Breaks," *Science* 263:324–325, 1994.

Ando et al., "Localization of Transforming Growth Factor–$\beta$ and Latent Transforming Growth Factor–$\beta$ Binding Protein in Rat Kidney," *Kidney International* 47:733–739, 1995.

Badylak et al., "Directed Connective Tissue Remodeling Upon a Biologic Collagen Substrate," *J. Cell Biochem.* Supplement 16F, p. 124, Apr. 3–16, 1992.

Bandara et al., "Gene Transfer to Synoviocytes: Prospects for Gene Treatment of Arthritis," *DNA and Cell Biology* 11(3):277–231, 1992.

Beck et al., "Rapid Publication TGF–$\beta_1$ Induces Bone Closure of Skull Defects," *J. Bone Miner. Res.* 6(11):1257–1265, 1991.

Benevisty and Reshef, "Direct Introduction of Genes into Rats and Expression of the Genes," *Proc. Natl. Acad. Sci. USA.* 83:9551–9555, 1986.

Boden et al., "Estrogen Receptor mRNA Expression in Callus During Fracture Healing in the Rat," *Calcif Tissue Int.* 45:324–325, 1989.

Bonadio et al., "Transgenic Mouse Model of the Mild Dominant form of Osteogenesis Imperfecta," *Proc. Natl. Acad. Sci. USA.* 87:7145–7149, 1990.

Culver and Blaese, "Gene Therapy for Cancer," *TIG* 10(5):174–178, 1994.

Carrington et al., "Accumulation, Localization and Compartmentation of Transforming Growth Factor $\beta$ During Endochondral Bone Development", *J. Cell. Biol.* 107:1969–1975, 1988.

Centrella et al., "Skeletal Tissue and Transforming Growth Factor $\beta$," *FASEB J.* 2:3066–3073, 1988.

Chaudhry et al., "Expression of Transforming Growth Factors $\beta_1$, $\beta_2$, $\beta_3$ in Neuroendocrine Tumors of the Digestive System," *Anticancer Research* 14:2085–2091, 1994.

Chen et al., "Bone Morphogenetic Protein–2b Stimulation of Growth and Osteogenic Phenotypes in Rat Osteoblast–like Cells: Comparison with TGF–$\beta_1$," *J. Bone Miner. Res.* 6(12):1387–1393, 1991.

Colosetti et al., "Axotomy of Rat Facial Nerve Induces TGF–$\beta$ and Latent TGF–$\beta$ Binding Protein," *Brain Research Bulletin* 37(6):561–567, 1995.

Cunningham et al., "Osteogenin and Recombinant Bone Morphogenetic Protein 2B are Chemotactic for Human Monocytes and Stimulate Transforming Growth Factor $\beta_1$ mRNA Expression," *Proc. Nat. Acad. Sci. USA* 89:11740–11744, 1992.

Dallas et al., "Characterization and Autoregulation of Latent Transforming Growth Factor $\beta$ (TGF$\beta$) Complexes in Osteoblast–like Cell Lines," *The Journal of Biological Chemistry*, 269(9):6815–22, 1994.

Davidson et al., "A Model System for in vivo Gene Transfer into the Central Nervous System Using an Adenoviral Vector," *Nature Genetics* 3:219–223, 1993.

Edelman et al., "c–myc in Vasculoproliferative Disease," *Circulation Research* 76(2):176–182, 1995.

Eklöv et al., "Lack of the Latent Transforming Growth Factor $\beta$ Binding Protein in Malignant, but not Benign Prostatic Tissue," *Cancer Research* 53:3193–3197, 1993.

Evans and Robbins, "Possible Orthopaedic Applications of Gene Therapy," *The Journal of Bone of Joint Surgery* 77–A(7):1103–1114, 1995.

Falcone et al., "Macrophage and Foam Cell Release of Matrix–bound Growth Factors," *The Journal of Biological Chemistry* 268(15):11951–11958, 1993.

Flaumenhaft, "Extracellular Regulation of Basic Fibroblast Growth Factor and Transforming Growth Factor–Beta Activity," *Dissertation Abstracts International* 53(3):1340–B, 1992.

Geber Garmet Technology v. Lectra Systems, 16 USPQ 2d 1436, Oct. 10, 1990.

Horowitz, et al., "Functional and Molecular Changes in Colony Stimulating Factor Secretion by Osteoblasts," *Connective Tissue Res.* 20:159–168, 1989.

Huggins et al., "Experiments on the Theory of Osteogenesis," *Arch. Surg.* 32(6):915–931, 1936.

Indolfi et al., "Inhibition of Cellular ras Prevents Smooth Muscle Cell Proliferation After Vascular Injury in vivo," *Nature Medicine* 1(16):541–545, 1995.

International Search Report dated Sep. 12, 1997 (PCT/US97/10079).

International Search Report dated Dec. 29, 1995 (PCT/US95/02251).

Izumi et al., "Transforming Growth Factor $\beta_1$ Stimulates Type II Collagen Expression in Cultured Periosteum–Derived Cells," *J. Bone Miner. Res.* 7(1):115–121, 1992.

Jingushi et al., "Acidic Fibroblast Growth Factor (aFGF) Injection Stimulates Cartilage Enlargement and Inhibits Cartilage Gene Expression in Rat Fracture Healing," *J. Orthop. Res.* 8:364–371, 1990.

Jingushi et al., "Genetic Expression of Extracellular Matrix Proteins Correlates with Histologic Changes During Fracture Repair," *J. Bone Miner. Res.* 7(9):1045–1055, 1992.

Joyce et al., "Transforming Growth Factor–$\beta$ and the Initiation of Chondrogenesis and Osteogenesis in the Rat Femur," *J. Cell Biol.* 110:2195–2207, 1990.

Joyce et al., 1991, "Role of Growth Factors in Fracture Healing", Clinical and Experimental Approaches to Dermal and Epidermal Repair: Normal and Chronic Wounds, Proceedings of the Third International Symposium on Tissue Repair, Miami, FL, Jan. 10–14, 1990, Wiley–Liss, Inc., NY, NY pp. 391–416.

Kaneda et al., "Increased Expression of DNA Cointroduced with Nuclear Protein in Adult Rat Liver," *Science* 243:375–378, 1989.

Kogawa et al., "TGF–β and Platelet," *Jpn. J. Clin. Hematol.* 35(4):370–375, 1994 (see abstract on p. 375).

Koli, "Growth–Inhibitory Effects of Transforming Growth Factor–β and 1,25–dihydroxyvitamin $D_3$ on Cultured Epithelial Cells: Relationships to Plasminogen Activation," *Diss. Abstr. Int.* 56(3):629–C, 1995.

Ledley, "Somatic Gene Therapy for Human Disease: Background and Prospects. Part I." *J. Pediatrics* 110(1):1–8, 1987.

Li et al., "Mapping of Human and Murine Genes for Latent TGF–β Binding Protein–2 (LTBP2)," *Mammalian Genome* 6:42–45, 1995.

Luyten et al., "Purification and Partial Amino Acid Sequence of Osteogenin, a Protein Initiating Bone Differentiation," *J. Biol. Chem.* 264(23):13377–13380, 1989.

Maeda et al., "Local Production and Localization of Transforming Growth Factor–beta in Tuberculous Pleurisy," *Clin. Exp. Immunol.* 92:32–38, 1993.

Majmudar et al., "Bone Cell Culture in a Three–Dimensional Polymer Bead Stabilizes the Differentiated Phenotype and Provides Evidence That Osteoblastic Cells Synthesize Type III Collagen and Fibronectin," *Journal of Bone and Mineral Research* 6(8):869–881, 1991.

Mannino and Gould–Fogerite, "Liposome Mediated Gene Transfer," *BioTechniques* 6(7):682–690, 1988.

Marshall, "Gene Therapy's Growing Pains," *Science* 269:1050–1055, 1995.

Matthews et al, "Bead Transfection: Rapid and Efficient Gene Transfer Into Marrow Stromal and Other Adherent Mammalian Cells," *Experimental Hematology* 21:697–702, 1993.

Miller and Vile, "Targeted Vectors for Gene Therapy," *FASEB J.* 9:190–199, 1995.

Miyazono et al., "Retention of the Transforming Growth Factor–β1 Precursor in the Golgi Complex in a Latent Endoglycosidase H–sensitive Form," *The Journal of Biological Chemistry,* 267(8):5668–5675, 1992.

Mizoi et al., "Immunoelectron Microscopic Localization of Transforming Growth Factor $β_1$ and Latent Transforming Growth Factor $β_1$ Binding Protein in Human Gastrointestinal Carcinomas: Qualitative Difference Between Cancer Cells and Stromal Cells," *Cancer Research* 53:183–190, 1993.

Mumper et al., "Interactive Polymeric Gene Delivery Systems for Enhanced Muscle Expression," Abstract, American Assoc. of Pharmaceutical Science, Miami Beach, FL, Nov. 6–9, 1995.

Nicolau et al., "In vivo Expression of Rat Insulin After Intravenous Administration of the Liposome–Entrapped Gene for Rat Insulin I," *Proc. Natl. Acad. Sci. USA.* 80:1068–1072, 1983.

* cited by examiner

SEQUENCE LISTING

```
<160> NUMBER OF SEQ ID NOS: 21

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide - Example Nuclear
      Translocation Signal

<400> SEQUENCE: 1

Pro Lys Lys Arg Lys Val Glu
 1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 2

Pro Pro Lys Lys Ala Arg Glu Val
 1               5

<210> SEQ ID NO 3
<211> LENGTH: 9
<212> TYPE: PRT
<213> ORGANISM: Artificial Sequence
<220> FEATURE:
```

```
<223> OTHER INFORMATION: Synthetic Peptide - Example nuclear
      Translocation Signal

<400> SEQUENCE: 3

Pro Ala Ala Lys Arg Val Lys Leu Asp
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 4

Lys Arg Pro Arg Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 5

Lys Ile Pro Ile Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 6

Gly Lys Arg Lys Arg Lys Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 7

Ser Lys Arg Val Ala Lys Arg Lys Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 8

Ser His Trp Lys Gln Lys Arg Lys Phe
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 9

Pro Leu Leu Lys Lys Ile Lys Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 10

Pro Gln Pro Lys Lys Lys Pro
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 11

Pro Gly Lys Arg Lys Lys Glu Met Thr Lys Gln Lys Glu Val Pro
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 12

Gly Arg Lys Lys Arg Arg Gln Arg Arg Arg Ala Pro
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 13

Asn Tyr Lys Lys Pro Lys Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 14
```

```
His Phe Lys Asp Pro Lys Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 15

Ala Pro Arg Arg Arg Lys Leu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 16

Ile Lys Arg Leu Arg Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 17

Ile Lys Arg Gln Arg Arg
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide - Example nuclear
      Translocation Signal

<400> SEQUENCE: 18

Ile Arg Val Arg Arg
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide - example
      cytoplasm-translocation signal sequence

<400> SEQUENCE: 19

Lys Asp Glu Leu
1

<210> SEQ ID NO 20
<211> LENGTH: 4
<212> TYPE: PRT
<213> ORGANISM: Artificial Sequence
```

-continued

```
<220> FEATURE:
<223> OTHER INFORMATION: Synthetic Peptide - example
      cytoplasm-translocation signal sequence

<400> SEQUENCE: 20

Arg Asp Glu Leu
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Peptide - example
      cytoplasm-translocation signal sequence

<400> SEQUENCE: 21

Lys Glu Glu Leu
1
```

COMPOSITIONS AND METHODS FOR DELIVERY OF AGENTS FOR NEURONAL REGENERATION AND SURVIVAL

CROSS-REFERENCE TO RELATED APPLICATIONS

This application is a continuation-in-part of U.S. application Ser. No. 09/088,419, filed Jun. 1, 1998, now abandoned, which is a continuation-in-part of U.S. application Ser. Nos. 08/805,381, filed Feb. 24, 1997, now abandoned; Ser. No. 08/805,382 filed Feb. 24, 1997, now abandoned; Ser. No. 08/805,383, filed Feb. 24, 1997 now abandoned; Ser. No. 08/718,904, filed Sep. 24, 1996, now issued as U.S. Pat. No. 6,037,329; which is a continuation-in-part of U.S. application Ser. No. 08/441,979, filed May 16, 1995, now abandoned; which is a continuation-in-part of U.S. application Ser. Nos. 08/213,446, filed Mar. 15, 1994, now abandoned; Ser. No. 08/213,447, filed Mar. 15, 1994, now abandoned; Ser. No. 08/297,961, filed Aug. 29, 1994, now abandoned, and Ser. No. 08/305,771, filed Sep. 13, 1994, now abandoned; all of which are incorporated by reference, as is PCT/US95/03448, filed Mar. 15, 1995.

TECHNICAL FIELD

The present invention relates generally to the treatment of neurons following NS injury that may result from surgery, trauma, compression, contusion, transection or other physical injury, from vascular pharmacologic or other insults including hemorrhagic or ischemic damage or from neurodegenerative or other neurological diseases. More specifically, the invention relates to the preparation and use of devices for transferring neuronal therapeutic agents and/or DNA encoding neuronal therapeutic agents into the NS, including devices that are gene activated matrices, to alter the function, gene expression or viability of neuronal cells therapeutically. The invention further relates to administration of such devices, including administration of matrices containing useful genes.

BACKGROUND OF THE INVENTION

Neuronal regeneration and restoration of neural connectivity within denervated tissues may be desirable events following acute or chronic nervous system (NS) injury resulting from physical transection/trauma, contusion/compression or surgical lesion, vascular pharmacologic insults including hemorrhagic or ischernic damage, or from neurodegenerative or other neurological diseases. Promotion of NS neuronal protection, neuronal survival and axon generation are well controlled processes that mainly originate during embryonic development and may persist through adulthood.

The stability of neuronal networks depends in part on the availability of a variety of specific architectural and biochemical cues in the neuronal environment that maintain neuronal projections, including axons. In the adult NS, the viability of neurons is maintained by the continuous retrograde flow of neurotrophic factors from the distal neuronal target to the neuronal cell body (perikaryon). Interruption of neural connections by physical severance of axons disconnects neuron from target and threatens neuronal survival.

Because of the spatiotemporal regulation of cues, including neurotrophic factors, essential for the maintenance of neural networks, axonal regrowth following NS injury is impaired by the absence of one or more appropriate stimuli in the vicinity of the damaged neuron. For example, neurotrophins (NT, discussed below) may be primary determinants of neuronal regeneration, and neurotrophin availability can be a primary limiting factor for axonal regrowth. Damaged neurons may initially start to regenerate axons, as a response to transient and regulated increases in the expression of neurotrophic factors, but regrowth is usually aborted within 14 days as intracellular stores of neurotrophin in the perikaryon are exhausted. Regrowth may also be inhibited in part by the deposition of fibrotic scar tissue during the course of wound healing. The synthesis and release of growth factors by mesenchymal and glial cells within the fibrotic scar may create localized microenvironments, or "sinks", having high growth factor concentrations. Because neurotrophin dependent axonal regeneration obligatory proceeds up a concentration gradient of the neurotropic factor, axonal entrapment within a growth factor sink may result. Following axonal injury, a neuron may be deprived of essential maintenance signals (e.g., neurotrophic factors that ordinarily would be supplied from distal target regions through an intact axon), and may die. Consequently, reconnection of neural pathways is prevented and functional recovery may be compromised.

Efforts to induce axonal regrowth following NS injury have included direct or indirect administration of neurotrophic compounds at or near lesion sites. According to such approaches, a neurotrophic compound may be directly applied at or near a lesion, or may be indirectly introduced to the damaged tissue by a transplanted cell secreting the neurotrophin(s). These methods often produce localized sinks of high neurotrophin concentration at the lesion site in which axons may become entrapped. Thus, axonal extension beyond the lesion and along the damaged projection tracts may be impossible. Failure to re-establish neural connections and the ensuring neuronal atrophy may result in complete loss of function.

Another approach designed to promote axonal regrowth after NS injury utilizes recombinant viral vectors to deliver therapeutic genes encoding neurotrophic factors. Depending on the viral vector construct and delivery vehicle used, such approaches may under certain circumstances, (i) elicit inappropriate antiviral immune responses, (ii) promote undesirable viral toxic effects, (iii) have limited efficacy due, for example, to inefficiency of genetically altered viral gene promoter sequences, (iv) be tumorigenic and/or (v) lack specificity regarding the cell type to which therapeutic genes are delivered. Poor targeting of such recombinant viral vectors to specific cell types, for example, may limit the value of such an approach and may establish localized accumulations of therapeutic gene products at the site of vector delivery, giving rise to the problems associated with localized growth factor sinks and axonal entrapment.

In view of these and other problems associated with neuroregenerative therapy, there is a compelling need for improved and more effective treatments that are free of the above disadvantages.

The present invention exploits the use of gene activated matrices that, when administered into a NS lesion site or along the axonal projection tract proximal to a lesion, deliver high amounts of nucleic acids encoding a desired neuronal therapeutic product by retrograde axonal transport to distant, targeted neuronal cell perikaryons without inducing localized sinks of active product that may lead to axonal entrapment, while providing other related advantages.

SUMMARY OF THE INVENTION

The compositions and methods of the present invention may be useful wherever neuronal regeneration and restoration of connectivity within neural networks is sought, for example following any acute or chronic NS injury resulting from physical transection/trauma, contusion/compression or surgical lesion, vascular pharmacologic insults including hemorrhagic or ischemic damage, or from neurodegenerative or other neurological diseases.

NS injury resulting from physical transection/trauma, vascular pharmacologic insults and/or neurological diseases may further include mechanical insult and may also include NS injury resulting from burns or other chemical exposure. Such exposure may include but need not be limited to exposure to toxic compounds such as carbon monoxide or other metabolic poisons, or exposure to free radicals, as may also accompany aging or contribute to the pathogenesis of neurodegenerative disease. For example, increased levels of reactive oxygen species may be present, and may correlate with sites of neurodegeneration, in diseases such as Alzheimer's disease, Parkinson's disease or Huntington's disease.

Interruption of neural connections may be a consequence of acute or chronic NS injury leading to physical severance of axons that threatens neuronal survival, as described above. Accordingly, the compositions and methods of the present invention may delay cell degeneration and cell death by restoring the continuous retrograde flow of neurotrophic factors, from distal neuronal targets to neuronal perikarya, that is essential for maintenance of neural networks.

A considerable amount of work has been directed to the development of biocompatible matrices for use in medical implants, including those specifically for connective tissue implantation such as in bone or wound healing. In context of the present invention, a matrix may be employed in association with the gene or DNA coding region encoding a neuronal therapeutic agent in order to easily deliver the gene to the site of NS injury. The matrix is thus a "biofiller" that provides a structure for the regulated regeneration of neuronal axons. Such matrices may be formed from a variety of materials presently in use for implanted medical applications.

According to the present invention, compositions and methods are provided for matrix mediated delivery of agents, and in preferred embodiments neuronal therapeutic encoding agents, that promote neuronal regeneration and survival.

In one aspect the invention provides a device for promoting neuronal regeneration, comprising a gene activated matrix comprising a biocompatible matrix and at least one neuronal therapeutic encoding agent having an operably linked promoter. In another aspect the invention provides a device for promoting neuronal survival, comprising a gene activated matrix comprising a biocompatible matrix and at least one neuronal therapeutic encoding agent having an operably linked promoter. In certain embodiments of these aspects, the promoter is an inducible promoter and in certain embodiments the promoter is a tissue specific promoter. In certain embodiments the promoter is GAP43 promoter, GFAP promoter, neuron specific enolase promoter, FGF-receptor promoter, elastase I gene control region, immunoglobulin gene control region, alpha-1-antitrypsin gene control region, beta-globin gene control region, myelin basic protein gene control region, myosin light chain 2 gene control region, RSV promoter, vaccinia virus 7.5K promoter, SV40 promoter, HSV promoter, MLP adenovirus promoter, MMTV LTR promoter, CMV promoter, metallothionein promoter, a promoter having at least one cAMP response element, tie promoter, VCAM-1 promoter, alpha V-beta 3 integrin promoters, ICAM-3 promoter, CD44 promoter, CD40 promoter, notch 4 promoter, or an event type-specific promoter. In other embodiments the promoter is a neuronal cell specific promoter, which in certain further embodiments may be GAP43 promoter, FGF receptor promoter or neuron specific enolase promoter.

In certain embodiments, the neuronal therapeutic encoding agent encodes a neurotrophic factor, which in certain further embodiments may be a member of the neurotrophin family and in certain other further embodiments may be a member of the FGF family. In certain of these embodiments the neurotrophic factor may be nerve growth factor (NGF), brain-derived neurotrophic factor (BDNF), cardiotrophin-1 (CT-1), choline acetyltransferase development factor (CDF), ciliary neurotrophic factor (CNTF), oncostatin M (OSM); fibroblast growth factor-1 (FGF-1), FGF-2, FGF-5, glial cell-line-derived neurotrophic factor (GDNF), insulin, insulin-like growth factor-1 (IGF-1), IGF-2, interleukin-6 (IL-6), leukemia inhibitor factor (LIF), neurite promoting factor (NPF), neurotrophin-3 (NT-3), NT4, platelet-derived growth factor (PDGF), protease nexin-1 (PN-1), S-100, transforming growth factor-β (TGF-β), or vasoactive intestinal peptide (VIP).

In some embodiments, the neuronal therapeutic encoding agent encodes an inhibitor of an antagonist of axonal generation or regeneration, and in certain further embodiments the inhibitor of an antagonist of axonal generation or regeneration is an inhibitor of TGF-beta. In certain embodiments, the inhibitor of TGF-beta is decorin, a TGF-beta inhibitory chemokine, an anti-TGF-beta antibody, an antisense TGF-beta oligonucleotide, a TGF-beta gene specific ribozyme or a mutated TGF-beta. In certain embodiments, the TGF-beta inhibitory chemokine is an ELR containing member of the CXC chemokine family. In certain embodiments, the ELR containing member of the CXC chemokine family is selected from the group consisting of interleukin-8, ENA-78, GROα, GROβ and GROγ. In certain embodiments, the inhibitor of TGF-beta is decorin. In certain embodiments, the inhibitor of TGF-beta is an anti-TGF-beta antibody. In certain embodiments, the inhibitor of TGF-beta is a mutated TGF-beta.

In some embodiments, the neuronal therapeutic encoding agent is non-covalently associated with the gene activated matrix. In certain embodiments, the neuronal therapeutic encoding agent is adsorbed to the gene activated matrix, and in certain other embodiments the neuronal therapeutic encoding agent is absorbed in the gene activated matrix. In certain embodiments, the neuronal therapeutic encoding agent is capable of inducing neuronal axonal generation or regeneration.

It is another aspect of the invention to provide a device for promoting neuronal regeneration, comprising a gene activated matrix, at least one support cell, and at least one neuronal therapeutic encoding agent having an operably linked promoter. It is yet another aspect of the invention to provide a device for promoting neuronal survival, comprising a gene activated matrix, at least one support cell, and at least one neuronal therapeutic encoding agent having an operably linked promoter. In certain embodiments of either of these aspects the support cell is a Schwann cell, and in certain other embodiments the support cell is an oligodendrocyte. In certain embodiments the support cell is an astrocyte and in certain embodiments the support cell is a microglial cell. In certain embodiments the support cell is a fibroblast. In certain embodiments the support cell is a macrophage. In certain embodiments the support cell is an inflammatory cell which may be a macrophage, a neutrophil, a monocyte, a granulocyte or a lymphocyte.

In certain embodiments of the invention, the neuronal therapeutic encoding agent is capable of maintaining axonal generation or regeneration. In certain embodiments the gene activated matrix is an implant for a neuronal injury site. In certain embodiments the gene activated matrix is formed upon administration. In certain embodiments the gene activated matrix is administered to a neuronal injury site. In certain embodiments the gene activated matrix is a composition selected that is a solution, a paste, a suspension, a powder, a semisolid, an emulsion or a gel. In certain preferred embodiments, the gene activated matrix is a paste. In certain embodiments the neuronal therapeutic encoding agent is a nucleic acid molecule, a vector, an antisense nucleic acid molecule or a ribozyme.

In some embodiments of the invention, the device further comprises a targeting agent, which is complexed with the neuronal therapeutic encoding agent and is capable of binding a neuronal cell surface receptor. In certain other embodiments, the targeting agent is conjugated to the neuronal therapeutic encoding agent and is capable of binding a neuronal cell surface receptor. In certain other embodiments, the targeting agent is complexed with the neuronal therapeutic encoding agent and is capable of binding a repair cell surface receptor. In certain other embodiments, the targeting agent is conjugated to the neuronal therapeutic encoding agent and is capable of binding a repair cell surface receptor. In certain other embodiments, the targeting agent is complexed with the neuronal therapeutic encoding agent and is capable of binding extracellular matrix. In certain other embodiments, the targeting agent is conjugated to the neuronal therapeutic encoding agent and is capable of binding extracellular matrix. In certain other embodiments, the device further comprises a nucleic acid binding domain, wherein the nucleic acid binding domain binds to a nucleic acid sequence that forms a portion of the neuronal therapeutic encoding agent. In certain other embodiments, the device further comprises at least one linker that may be a cleavable linker, a linker that provides an intracellular protein sorting peptide sequence, a linker that reduces steric hindrance, a linker that provides a nuclear translocation signal or a linker that possesses a nucleic acid condensing ability. In certain other embodiments, the device contains sub-physiologic amounts of a neuronal therapeutic agent. In certain other embodiments, the device contains physiologic amounts of a neuronal therapeutic agent.

In certain other embodiments of the above described aspects of the invention, the device further comprises a conduit having a lumen. In certain embodiments, the conduit comprises the gene activated matrix and in certain other embodiments, the lumen contains the gene activated matrix. In certain embodiments, the conduit comprises a bioabsorbable material, which in certain further embodiments may be a material comprising gene activated matrix, type I collagen, laminin, polyglycolic acid, glycolide trimethylene carbonate (GTMC), poly (L-lactide-co-6-caprolactone), glycoproteins, proteoglycans, heparan sulfate proteoglycan, nidogen, glycosaminoglycans, fibronectin, epidermal growth factor, fibroblast growth factor, nerve growth factor, cytokines, or DNA encoding growth factors and cytokines.

In certain other embodiments, the conduit comprises a non-bioabsorbable material, which in certain further embodiments is be polyamide, polyimide, polyurethane, segmented polyurethane, polycarbonate or silicone. In certain other embodiments, the non-bioabsorbable material comprises an etched microporous synthetic polymer surface. In certain embodiments the conduit is tubular.

Turning to another aspect of the invention, a method is provided for transferring a neuronal therapeutic encoding agent into a neuronal cell, comprising contacting a neuronal cell with any one of the devices just described to effectively transfer the neuronal therapeutic encoding agent into the neuronal cell. In one embodiment, transfer of the neuronal therapeutic encoding agent comprises retrograde axonal transport of the neuronal therapeutic encoding agent. In another embodiment the method further comprises expression of the neuronal therapeutic encoding agent at a neuronal cellular site distinct from a site of contact between the device and the neuronal cell. In another embodiment, the device is contacted with a neuronal cell at a neuronal injury site. In another embodiment, the device is contacted with a neuronal cell in a manner such that axonal generation or regeneration occurs. In a further embodiment, axonal regeneration occurs without axonal entrapment. In another embodiment, the device is contacted with a neuronal cell in a manner that promotes neuronal survival. In a further embodiment, neuronal survival is promoted without axonal entrapment. In certain further embodiments a neural connection is established or reestablished.

It is yet another aspect of the invention to provide a method for transferring a neuronal therapeutic encoding agent into a repair cell, comprising contacting a repair cell with any one of the devices described above to effectively transfer the neuronal therapeutic encoding agent into the repair cell. In one embodiment, the device is contacted with a repair cell at a neuronal injury site, and in another embodiment the device is contacted with a repair cell in a manner such that axonal generation or regeneration occurs. In certain further embodiments axonal generation or regeneration occurs without axonal entrapment. In another embodiment, the device is contacted with a repair cell in a manner that promotes neuronal survival. In a further embodiment, neuronal survival is promoted without axonal entrapment. In certain other embodiments a neural connection is established or reestablished.

In certain embodiments of the method the device contains sub-physiologic amounts of a neuronal therapeutic agent, and in certain other embodiments the device contains physiologic amounts of a neuronal therapeutic agent.

In still another aspect, the invention provides a method of preparing a gene activated matrix for promoting neuronal regeneration and survival, comprising contacting a neuronal therapeutic encoding agent with a biocompatible matrix such that the neuronal therapeutic encoding agent associates non-covalently with the matrix. In one embodiment, the neuronal therapeutic encoding agent is adsorbed to the gene activated matrix, and in another embodiment the neuronal therapeutic encoding agent is absorbed in the gene activated matrix. In certain embodiments the neuronal therapeutic encoding agent is a nucleic acid molecule, a vector, an antisense molecule or a ribozyme.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entireties.

DETAILED DESCRIPTION OF THE INVENTION

Figure 1:
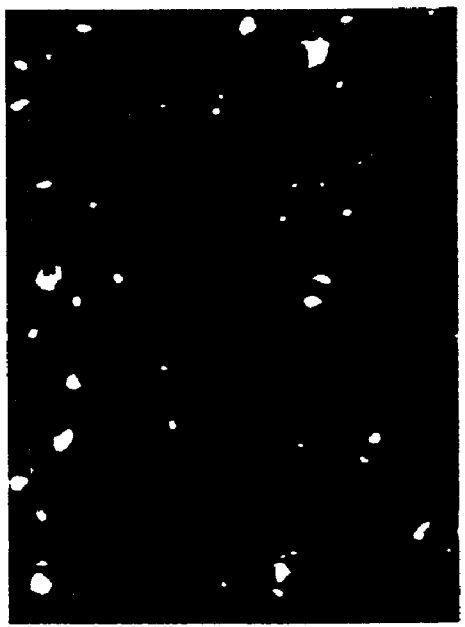
FIG. 1 depicts expression of axonally delivered marker protein in an optic nerve model of CNS injury.
Figure 1:

The present invention relates to an in vivo method for presentation and transfer of DNA into mammalian repair cells for the purpose of expressing therapeutic agents. The method of the invention involves implanting or placing gene activated matrices into a nervous system (NS) injury site. An NS site may be any location in which a neuronal cell is present, including but not limited to central nervous system (CNS) and peripheral nervous system (PNS) and any other situs at which neuronal cells or processes thereof may reside, including neuronal axonal projection tracts.

Direct plasmid DNA transfer from a matrix to a mammalian repair cell, through stimulation of the wound healing process, offers a number of advantages. First, the ease of producing and purifying DNA constructs compares favorably with traditional protein production method cost. Second, matrices can act as structural scaffolds that, in and of themselves, promote cell in growth and proliferation. Thus, they facilitate the targeting of repair cells for gene transfer. Third, direct gene transfer may be an advantageous method of drug delivery for molecules that normally undergo complex biosynthetic processing or for receptors which must be properly positioned in the cellular membrane. These types of molecules would fail to work if exogenously delivered to cells.

As used herein, a "repair cell" is defined as any cell which may be stimulated to migrate, proliferate or alter its structural and/or functional activity in response to tissue injury including injury to any NS neuron. Repair cells are a component of the wound healing response. Such cells may include neurons, astrocytes, oligodendrocytes, and other neuroglial cells; choroid plexus cells; ependymal cells; meningeal cells; Schwann cells; fibroblasts, capillary endothelial cells, capillary pericytes, and other mesenchymal cells; microglial cells and inflammatory cells including macrophages, neutrophils, moncytes, granulocytes, lymphocytes, other mononuclear inflammatory cells, segmented inflammatory cells and granulation tissue cells.

The present invention also relates to pharmaceutical compositions comprising matrices containing DNA for use in wound healing. The compositions of the invention are generally comprised of a biocompatible matrix material containing DNA encoding a therapeutic protein of interest.

The invention overcomes shortcomings specifically associated with current recombinant protein therapies for wound healing applications. First, direct gene transfer is a rational strategy that allows transfected cells to (a) make physiological amounts of therapeutic protein, modified in a tissue- and context-specific manner, and (b) deliver this protein to the appropriate cell surface signaling receptor under the appropriate circumstances. For reasons described above, exogenous delivery of such molecules is expected to be associated with significant dosing and delivery problems. Second, repeated administration, while possible, is not required with gene activated matrix technology: cell uptake of DNA can be controlled precisely with well-established sustained release delivery technologies, or, alternatively, integration of transfected DNA can be associated with long term recombinant protein expression.

1. DNA DEVICES

The present methods and compositions may employ a variety of different types of DNA molecules. The DNA molecules may include genomic, cDNAs, single stranded DNA, double stranded DNA, triple stranded DNA, oligonucleotides and Z-DNA. DNA molecules to be used according to the compositions and methods of the present invention include neuronal therapeutic encoding agents. Neuronal therapeutic encoding agents include any nucleic acid molecules that encode proteins to promote neuronal growth (which includes neuronal axon generation and regeneration) and/or neuronal survival (which refers to maintenance of neuronal viability). Neuronal therapeutic encoding agents may encode proteins that provide neuronal growth and/or neuronal survival when expressed in neurons, but certain proteins that are encoded by neuronal therapeutic encoding agents may also promote neuronal growth and/or survival when expressed in non-neuronal cell types. For example, various cell types in an affected tissue may participate in fibrotic scar deposition that may, inter alia, lead to undesirable growth factor sinks and may further present impediments to NS regeneration and reestablishment of neural networks. As another example, in neurodegenerative disease CNS injury wherein CNS microglia contribute to the pathogenesis, neuronal therapeutic agents that are targeted to and capable of regulating the biological activity of such microglia may be useful. For instance, neuronal therapeutic agents that are targeted to regulate the viability, biosynthetic potential or proliferative capacity of, e.g., microglia, or neuronal therapeutic encoding agents that deliver genes able to regulate one or more pathogenetic gene products of, e.g., microglia, are non-limiting illustrations of additional agents according to the invention that may be useful.

The DNA molecules may code for a variety of factors that promote wound healing including extracellular, cell surface, and intracellular RNAs and proteins. Examples of such proteins include growth factors, cytokines, therapeutic proteins, hormones and peptide fragments of hormones, inhibitors of cytokines, peptide growth and differentiation factors, interleukins, chemokines, interferons, colony stimulating factors and neurotrophic factors.

The DNA molecules may also encode blocking factors, including proteins or non-proteins that block pathological processes, thereby allowing the natural wound healing process to occur unimpeded. Examples of such blocking factors include antisense molecules or ribozymes that interfere with or destroy RNA function, and DNAs that, for example, encode tissue inhibitors of enzymes that destroy tissue integrity, e.g,. inhibitors of metalloproteinase associated with arthritis. In one such embodiment, matrix metalloproteinase (MMP) expression may be helpful to nerve regeneration, e.g., by removing extracellular matrix components of the scar that block the path of axons. MMP-2 and MMP-9 are both expressed by regenerating axons (Yong et al., (1998) *Trends In Neurol. Sci.* 21:75–78). In a preferred embodiment, DNA encoding antagonists of cytokines or growth factors, for example, antagonists of transforming growth factor-β (TGF-β) or connective tissue growth factor (CTGF), may act to block matrix deposition of the scar and thus promote nerve regeneration.

One may obtain the DNA segment encoding the protein or non-protein of interest using a variety of molecular biological techniques, generally known to those skilled in the art. For example, cDNA or genomic libraries may be screened using primers or probes with sequences based on the known nucleotide sequences. Polymerase chain reaction (PCR) may also be used to generate the DNA fragment encoding the protein of interest. Alternatively, the DNA fragment may be obtained from a commercial source.

Nucleic acid sequences that vary from those described in the literature are also encompassed by the invention, so long as the altered or modified nucleic acid still encodes a protein or non-protein that functions to stimulate neuronal axon regeneration in any direct or indirect manner, including but not limited to effects on axonal regrowth, on neuronal survival, on the activities of other cell types in the vicinity of a NS lesion or on wound healing generally. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art. Such modifications include the deletion, insertion or substitution of bases which result in changes in the amino acid sequence. Changes may be made to increase the activity of an encoded protein, to increase its biological stability or half-life, to change its glycosylation pattern, confer temperature sensitivity or to alter the expression pattern of the protein and the like. All such modifications to the nucleotide sequences are encompassed by this invention.

Modification of DNA may be performed by a variety of methods, including site-specific or site-directed mutagenesis of DNA encoding the protein and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (e.g., a member of the FGF family or a neurotrophin). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Conservative substitutions of amino acids are well-known and may be made generally without altering the biological activity of the resulting molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to and internalize upon binding to the appropriate receptors. Those that retain this ability are suitable for use in the constructs and methods herein.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of neuronal therapeutic genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982); these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (±0.3); asparagine (+0.2); glutamine (+0.2glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The DNA encoding the translational or transcriptional products of interest, for example a neuronal therapeutic encoding agent, may be recombinantly engineered into a variety of vector systems that provide for replication of the DNA in large scale for the preparation of gene activated matrices. These vectors can be designed to contain the necessary elements for directing the transcription and/or translation of the DNA sequence taken up by neurons or by repair cells at a wound site in vivo, such as injured neurons at an NS lesion site.

Vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18–23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Vectors that allow for the in vitro transcription of RNA, such as SP6 vectors, may also be used to produce large quantities of RNA that may be incorporated into matrices. Alternatively, recombinant virus vectors may be engineered, including but not limited to those derived from viruses such as herpes virus, retroviruses, vaccinia virus, poxviruses, adenoviruses, adeno-associated viruses or bovine papilloma virus. While integrating vectors may be used, non-integrating systems, which do not transmit the gene product to daughter cells for many generations are preferred for wound healing, such as neuronal axon regeneration. In this way, the gene product is expressed during the wound healing/neuronal repair/axonal regeneration process, and as the gene is diluted out in progeny generations, the amount of expressed gene product is diminished. As described above, restoration of neural networks reestablishes retrograde flow of neurotrophic factors, thus obviating in certain situations the need for constitutive expression of a GAM delivered neuronal therapeutic encoding agent.

Methods which are well known to those skilled in the art can be used to construct expression vectors containing the protein coding sequence operatively associated with appropriate transcriptional/translational control signals. These methods include in vitro recombinant DNA techniques, and synthetic techniques. See, for example, the techniques described in Sambrook, et al., 1992, *Molecular Cloning, A Laboratory Manual*, Cold Spring Harbor Laboratory, N.Y. and Ausubel et al., 1989, *Current Protocols in Molecular Biology*, Greene Publishing Associates & Wiley Interscience, New York.

The genes encoding the proteins of interest may be operatively associated with a variety of different promoter/enhance elements, which may include but need not be limited to promoter, enhancer, transcription factor binding site and other gene expression regulatory sequences. The expression elements of these vectors may vary in their strength and specifities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. In any event, the promoter is included as an "operably linked" promoter, which refers to the situation of a promoter in any embodiment of a neuronal therapeutic encoding agent according to the present invention in such a manner as to influence the expression of the neuronal therapeutic agent encoded by the neuronal therapeutic encoding agent. For example, tissue specific promoter/enhancer elements, including distinct promoter and enhancer sequences that are derived from different sources and engineered to produce a recombinant promoter/enhancer element, may be used to regulate the expression of the transferred DNA in specific cell types. Examples of described transcriptional control regions exhibiting tissue specificity that may be used include but are not limited to glial fibrillary acid protein (GFAP) gene control region, which is active in astrocytes (Brenner and Messing, 1996, *Methods: A Companion to Methods in Enzymology* 10:351–364); GAP43 gene control region (de Groen et al., 1995, *J. Mol. Neurosci.* 6:109–119); elastase I gene control region (Swift et al., 1984. *Cell* 38:639–646; Ornitz et al., 1986, *Cold Spring Harbor Symp. Quant. Biol.* 50:399–409; MacDonald, 1987, *Hepatology* 7:42S-51S); immunoglobulin gene control region, which is active in lymphoid cells (Grosechedl et al., 1984, *Cell* 38:647–658; Adama et al., 1985, *Nature* 318:533–538; Alexander et al., 1987, *Mol. Cell. Biol.* 7:1436–1444); FGF-receptor promoter; alpha-1-antitrypsin gene control region, which is active in liver (Kelsey et al., 1987, *Genes and Devel.* 1:161–171); beta-globin gene control region, which is active in myeloid cells (Magram et al., 1985, *Nature* 315:338–340; Kollias et al., 1986, *Cell* 46:89–94); myelin basic protein gene control region, which is active in oligodendrocyte cells in the brain (Readhead et al., 1987, *Cell* 48:703–712); and myosin light chain 2 gene control region, which is active in skeletal muscle (Shani, 1985, *Nature* 314:283–286). Promoters isolated from the genome of viruses that grow in mammalian cells, (e.g., RSV, vaccinia virus 7.5K, SV40, HSV, adenoviruses MLP, MMTV LTR and CMV promoters) may be used, as well as promoters produced by recombinant DNA or synthetic techniques.

In some instances, the promoter elements may be constitutive or inducible promoters and can be used under the appropriate conditions to direct high level or regulated expression of the gene of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhance elements, etc.

In addition to DNA sequences encoding therapeutic proteins of interest, the scope of the present invention includes the use of ribozymes or antisense DNA molecules that may be transferred into the mammalian repair cells. Such ribozymes and antisense molecules may be used to inhibit the translation of RNA encoding proteins of genes that inhibit a disease process or the wound healing process thereby allowing tissue repair to take place.

The expression of antisense RNA molecules will act to directly block the translation of mRNA by binding to targeted mRNA and preventing protein translation. The expression of ribozymes, which are enzymatic RNA molecules capable of catalyzing the specific cleavage of RNA may also be used to block protein translation. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences. RNA molecules may be generated by transcription of DNA sequences encoding the RNA molecule.

It is also within the scope of the invention that multiple genes, combined on a single genetic construct under control of one or more promoters, or prepared as separate constructs of the same or different types may be used. Thus, an almost endless combination of different genes and genetic constructs may be employed. Certain gene combinations may be designed to, or their use may otherwise result in, achieving synergistic effects on cell stimulation and regeneration, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations. For example, in one embodiment, expression of genes encoding neuronal therapeutic agents combined with expression of genes encoding anti-fibrotic or anti-inflammatory cytokines provide synergistic stimulation of neuron growth.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, a therapeutic and in particular a neuronal therapeutic gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

This invention provides novel ways in which to utilize various known neuronal therapeutic DNA segments and recombinant vectors. As described above, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a neuronal therapeutic protein and does not include any coding or regulatory sequences that would have a significant adverse effect on neurons. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

After identifying an appropriate neuronal therapeutic encoding agent, such as a suitable gene or nucleic acid molecule, it may be inserted into any one of the many vectors currently known in the art, so that it will direct the expression and production of the neuronal therapeutic protein when incorporated into a neuron. In a recombinant expression vector, the coding portion of the DNA segment is positioned under the control of a promoter. The promoter may be in the form of the promoter which is naturally associated with a neuronal therapeutic agent encoding gene, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a neuronal therapeutic agent encoding gene in its natural environment. Such promoters may include those normally associated with other neuronal therapeutic genes, and/or promoters isolated from any other bacterial, viral, eukaryotic, or mammalian cell. Naturally, it will be important to employ a promoter that effectively directs the expression of the DNA segment in target cells, in neurons, for example, a GAP43, FGF-receptor or neuron specific enolase promoter and control region.

The use of recombinant promoters and/or enhancers to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. The currently preferred promoters are those such as GFAP promoter, GAP43 promoter, CMV, RSV LTR, the SV40 promoter alone, and the SV40 promoter in combination with various enhancer elements. For example, neuronal therapeutic agents may be targeted to neurons with the GAP43 promoter or the neuron specific enolase promoter, and anti-fibrotic agents may be targeted to astrocytes with the GFAP promoter.

Neuronal therapeutic agent encoding genes and DNA segments may also be in the form of a DNA insert which is located within the genome of a recombinant virus, for example, a recombinant adenovirus, adeno-associated virus (AAV), herpes virus, pox virus or retrovirus. In such embodiments, to place the gene in contact with a neuron, one would prepare the recombinant viral particles, the genome of which includes the neuronal therapeutic encoding gene insert, and simply contact the NS region containing injured neuronal cells with the a delivery device containing the virus, whereby the virus infects the cells and transfers the genetic material.

In certain preferred embodiments, one would impregnate a matrix or implant material with virus by soaking the material in recombinant virus stock solution, e.g., for 1–2 hours, and then contact the damaged NS cells or tissues with the resultant, impregnated matrix. Cells then penetrate, or grow into, the matrix, thereby contacting the virus and allowing viral infection which leads to the cells taking up the desired gene or cDNA and expressing the encoded protein.

In other preferred embodiments, one would form a matrix-nucleic acid admixture, whether using naked DNA, a plasmid or a viral vector, by mixing the nucleic acid or construct with matrix or implant material that is in solution, suspension, paste, colloid or other liquid form as described herein, permitting the admixture to undergo polymerization, gelation, semisolidification or the like as may be a property of the particular material selected, and contacting the injured NS neuronal cells or tissues with the resultant admixed matrix. The matrix may then deliver the nucleic acid into the cells following disassociation at the cell surface, or in the immediate cellular environment. Equally, the matrix admixture itself, especially a particle- or fiber-DNA admixture, may be taken up by cells to provide subsequent intracellular release of the genetic material. The matrix may then be extruded from the cell, catabolized by the cell, or even stored within the cell. The molecular mechanism by which a neuron-compatible matrix achieves transfer of DNA to a cell is immaterial to the practice of the present invention.

a. Gene Activated Matrix (GAM) Delivery Systems

As noted above, the complexes and the constructs of the present invention may be formulated into a gene activated matrix (GAM) for administration at a NS lesion site. This embodiment of the present invention relates to an in vivo method for presentation and transfer of DNA into host neurons and/or repair cells for the purpose of expressing therapeutic agents. Gene activated matrices are disclosed in U.S. Pat. No. 5,763,416 and in published PCT App. No. WO 97/38729, the disclosures of which are hereby incorporated by reference in their entirety.

As also noted above, neurons in the NS may react to physical injury by transiently sprouting regenerating axons that may respond to neuronal therapeutic factors and/or other trophic spatiotemporal signals, provided such signals are delivered before the onset of neuronal atrophy and necrosis. Successful neuronal regeneration and functional restoration of NS neural networks after traumatic injury may be compromised by tissue repair mechanisms of non-neural cell types. For example, as discussed above, inappropriate scar tissue deposition may obstruct projection tracts for neuronal regeneration by creating sinks of neurotrophic factors that lead to axonal development, and glial scar matrix may physicochemically inhibit axonal regeneration. In most tissues wound healing is usually a coordinated, stereotyped sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages) (e) formation of granulation tissue (fibroplasia and angiogenesis). This sequence of cellular events has been observed in wounds from all tissues and organs generated in a large number of mammalian species (See Berry et al., 1998 In: *CNS Injuries: Responses and Pharmacological Strategies*, A. Logan and M. Berry, eds., CRC Press, Boca Raton, Fla.; Gailet et al., 1994, *Curr. Opin. Cell. Biol.* 6:717–725). Therefore, the cellular sequence described above is a universal aspect of the repair of all mammalian tissues.

The invention is based on the discovery that many types of repair cells involved in the wound healing process, including by way of illustration and not limitation astrocytes, glial cells, microglial cells and fibroblasts, will naturally proliferate and migrate to the site of tissue injury and infiltrate the gene activated matrix (GAM). In the case of (generally non-proliferating) neuronal cells attempting axonal regeneration following injury, the axonal sprouts may similarly contact and/or invade the GAM. Surprisingly, these repair cells, which are normally difficult to efficiently transfect either in vitro or in vivo, are extremely efficient at taking up and expressing DNA when activated by the wound healing process. Regenerating neuronal axons may also contact and/or invade the GAM, providing an opportunity for DNA uptake and delivery to perikarya by retrograde transport. Thus, the methods of the present invention are designed to efficiently transfer DNA molecules encoding therapeutic agents to regenerating neurons and/or repair cells. The devices and methods involve the administration, within a host at the site of NS injury, of GAM containing constructs, complexes or conjugates including a biocompatible matrix and a neuronal therapeutic encoding agent and, optionally, one or more of a ligand, a promoter, a nucleic acid binding domain, a linker, translational products (i.e., therapeutic proteins), transcriptional products (i.e., antisense nucleic acids or ribozymes) or any other agent that may be a neuronal therapeutic agent.

For example, as the regenerating axon may grow into and contact the CGAM, it may take up DNA encoding a therapeutic agent, which DNA is delivered to the perikaryon by retrograde axonal transport. The transfected neurons may thereby serve as distal bioreactors producing therapeutic agents that influence the local repair environment through expression of the delivered DNA. As described above, expression of neuronal therapeutic agents may in certain embodiments of the invention further comprise regulated transcription of a neuronal therapeutic agent, for example through a neuron specific promoter and/or a nucleic acid binding domain. For example, neurotrophic factors, growth factors, cytokines or other neuronal therapeutic agents produced by the transfected neurons may stimulate and amplify the cascade of physiological events normally associated with the neuronal regeneration process. Because the GAM may include DNA encoding a neuronal therapeutic agent but not the therapeutic agent itself, elaboration of a therapeutic agent sink within the GAM loaded lesion and resulting axonal entrapment may be avoided, particularly if the therapeutic agent is engineered to be retained intracellularly and to exert its neuronal therapeutic effect intracellularly, or where the therapeutic agent is biosynthetically produced and released extracellularly at sufficiently low levels to avoid a sink effect.

Alternatively, the regenerating axons of neurons, or other involved cell types, may take up and express DNA encoding proteins that inhibit the activity of antagonists of the neuronal survival/axonal generation/regeneration process. Such antagonists may operate on any cell type in the vicinity of an NS lesion and by any mechanism, direct or indirect, to interfere with NS wound healing. Accordingly, in certain embodiments of the invention a neuronal therapeutic encoding agent may encode an inhibitor of such an antagonist of axonal generation or regeneration. As a non-limiting example, for instance, anti-scaring activity of the cell surface proteoglycan decorin is related to retention by decorin of TGF-β, thereby preventing binding of TGF-β to its receptor. (Border et al., *Nature* 360:361, 1992; Hausser et al., *FEBS Lett.* 353:243–245, 1994.) Accordingly, delivery and expression of decorin-encoding genes at NS injury sites, as provided by the present invention, may similarly discourage local scarring while favoring axonal regeneration. The DNA may also encode antisense or ribozyme RNA molecules that may be used to inhibit translation in neural or non-neural cells of mRNAs encoding inflammatory proteins, scar tissue components or other factors that inhibit neural regeneration. As another non-limiting example, extracellular matrix deposition accompanying scar formation and that is promoted by TGF-beta may be impaired by a neuronal therapeutic encoding agent encoding a TGF-beta inhibitory chemokine, for example the ELR containing members of the CXC family of chemokines described by Moore et al. (1998 *J. Invest. Med.* 46:113). As another non-limiting example, anti-TGF-beta antibodies may be useful neuronal therapeutic agents because of their ability to interfere with TGF-beta mediated scar tissue generation. (See, e.g., Gharaee-Kermnani et al., 1996 *J. Biol. Chem.* 271:17779.)

The gene activated matrices of the invention can be transferred to the patient using a variety of techniques. For example, when stimulating neural regeneration, the matrices are transferred directly to the site of the NS lesion, e.g., the axotomized neuron. Since the method of the invention is based on natural axonal sprouting in response to axonotomy leading to axonal entry into the gene activated matrix located at the lesion site, and the consequential uptake of e.g., DNA, it is understood that the matrices must be transferred into a site in the body where NS lesions and axonal sprouting have been induced.

One particularly important feature of the present invention is that the repair process may be engineered to result in either neural regeneration and/or the formation of scar tissue. Around a suture, for example, it may be desirable to form scar tissue to hold inherently weak tissue together. At the site of the actual NS injury (e.g., the neuronal lesion), however, the expression of neuronal therapeutic agents may result in regeneration of neurons without the formation of scar tissue. In many instances, such neuronal regeneration is desirable. As described above, overexpression of neuronal therapeutic agents at NS lesion sites may lead to therapeutic agent sinks and resulting axonal entrapment. It is therefore within the scope of this aspect of the invention to provide nucleic acid constructs, for use as neuronal therapeutic agent encoding molecules in GAMs, that may qualitatively or quantitatively regulate the biosynthesis and localization of neuronal therapeutic agents in a manner that avoids formation of such sinks. For example, by way of illustration and not limitation, pharmacologically inactive genetic constructs encoding polypeptide domains that direct a neuronal therapeutic agent to a particular subcellular localization, or constructs having promoters that permit only restricted expression levels of such agents, may circumvent the generation of therapeutic agent sinks. Accordingly, when the delivered agent is a neuronal therapeutic encoding agent that is pharmacologically inactive at the lesion site where it is administered, the problem of axonal entrapment in lesion associated therapeutic agent sinks is overcome by axonal transport of the therapeutic encoding agent away from the lesion prior to biosynthesis of the encoded therapeutic agent at a location distinct from the lesion site. These and other means for regulating neuronal therapeutic agent encoding gene expression are within the scope of the present invention. Therefore, the methods of invention may be used to stimulate NS tissue repair and/or wound healing, either with or without the formation of scar tissue, depending on the type and amount of therapeutic agent expressed.

b. The Gene Activated Matrix

Any biocompatible matrix material containing DNA encoding a therapeutic agent of interest, e.g., therapeutic proteins, or transcriptional product, e.g., antisense or ribozymes, can be formulated and used in accordance with the invention. Further information regarding useful GAM materials may be found in the disclosure of U.S. Pat. No. 5,763,416, for example, which is incorporated by reference herein.

The gene activated matrices of the invention may be derived from any biocompatible material. Such materials may include, but are not limited to, biodegradable or non-biodegradable materials formulated into scaffolds that support cell attachment and growth, powders or gels. Matrices may be derived from synthetic polymers or naturally occurring proteins such as collagen, fibrin or other extracellular matrix proteins, or other structural macromolecules.

The DNA incorporated into the matrix may encode any of a variety of therapeutic proteins depending on the envisioned therapeutic use. Such proteins may include neuronal therapeutic agents such as neurotrophins, growth factors, cytokines, enzymes, hormones, proto-oncogenes or any other proteins capable of regulating the growth, differentiation or physiological function of neurons and/or other cells at or near NS lesions. The DNA may also encode antisense or ribozyme molecules that block the translation of proteins that promote scar formation, that inhibit wound repair and/or that induce inflammation. As described above, the DNA may also encode antagonists of cytokines or growth factors, which cytokines or growth factors promote extracellular matrix deposition and scar formation. Thus, for example, antagonists of TGF-β or CTGF may promote nerve regeneration.

The transferred DNA need not be integrated into the genome of the target cell; indeed, the use of non-integrating DNA in the gene activated matrix is a preferred embodiment of the present invention. In this way, when the neural network pathway is restored and the gene product is no longer needed, the gene product may no longer be expressed.

Therapeutic kits containing a biocompatible matrix and DNA form another aspect of the invention. In some instances the kits will contain preformed gene activated matrices thereby allowing the physician to directly administer the matrix within the body. Alternatively, the kits may contain the components necessary for formation of a gene activated matrix. In such cases the physician may combine the components to form the gene activated matrices which may then be used therapeutically by placement within the body. In one embodiment of the invention the matrices may be used to coat surgical devices such as suture materials or implants. In yet another embodiment of the invention, gene activated matrices may include ready to use sponges, tubes, band-aids, lyophilized components, gels, patches or powders and telfa pads, to name a few examples.

c. The Matrix Materials

In one aspect of the invention, compositions are prepared in which the DNA encoding the therapeutic agent of interest (e.g., a neuronal therapeutic agent) is associated with or impregnated within a matrix to form a gene activated matrix.

The matrix compositions function (i) to facilitate in growth of regenerating axons (targeting); and (ii) to harbor DNA (delivery). Once the gene activated matrix is prepared it is stored for future use or placed immediately at or near the site of the wound.

The type of matrix that may be used in the compositions, devices and methods of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from either natural or synthetic materials, or both. The matrices may be non-biodegradable in instances where it is desirable to leave permanent structures in the body; or biodegradable where the expression of the therapeutic protein is required only for a short duration of time. For example, the matrices may take the form of sponges, implants, tubes, telfa pads, band-aids, bandages, pads, lyophilized components, gels, patches, powders or nanoparticles. In addition, matrices can be designed to allow for sustained release of the DNA over prolonged periods of time. Such sustained release of a therapeutic DNA construct, and corresponding sustained expression of neuronal therapeutic agents encoded thereby, may be preferred in situations where long neural tract regrowth is sought, for example, in spinal cord or optic system repair.

The choice of matrix material will differ according to the particular circumstance and the site of the lesion that is to be treated. Matrices such as those described in U.S. Pat. Nos. 5,270,300 or 5,763,416, incorporated herein by reference, may be employed. Physical and chemical characteristics, such as, e.g., biocompatibility, biodegradability, strength, rigidity, interface properties and even cosmetic appearance may be considered in choosing a matrix, as is well known to those of skill in the art. Appropriate matrices will both deliver the DNA molecule and also act as an in situ scaffolding through which regenerating axons may migrate.

Where the matrices are to be maintained for extended periods of time, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. The bioceramics may be altered in composition, such as in calcium-aluminate-phosphate; and they may be processed to modify particular physical and chemical characteristics, such as pore size, particle size, particle shape, and biodegradability. Polymeric matrices may also be employed, including acrylic ester polymers and lactic acid polymers, as disclosed in U.S. Pat. Nos. 4,521,909, and 4,563,489, respectively, each incorporated herein by reference. Particular examples of useful polymers are those of orthoesters, anhydrides, propylene-cofumarates, or a polymer of one or more γ-hydroxy carboxylic acid monomers, e.g., γ-hydroxy auric acid (glycolic acid) and/or γ-hydroxy propionic acid (lactic acid).

The constructs and complexes may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponges (see, e.g., U.S. Pat. Nos. 3,956,044 and 4,045,238; available from Weck, Alcon, and Mentor), that has been soaked in the composition and that releases the composition upon contact with the host tissue. These are particularly useful for application to NS lesion sites during surgery in which only a single administration is possible. The compositions may also be applied in pellets (such as Elvax pellets, made of ethylene-vinyl acetate copolymer resin; about 0.5–100, preferably 1–20, and more preferably 1–5 μg of conjugate per 1 mg resin) that can be implanted in the vicinity of the lesion during surgery.

In preferred embodiments, it is contemplated that a biodegradable matrix will likely be most useful. A biodegradable matrix is generally defined as one that is capable of being reabsorbed into the body. Potential biodegradable matrices for use in connection with the compositions, devices and methods of this invention include, for example, biodegradable and chemically defined calcium sulfate, tricalciumphosphate, hydroxyapatite, polyactic acid, polyanhydrides, matrices of purified proteins, and semipurified extracellular matrix compositions.

Other biocompatible biodegradable polymers that may be used are well known in the art and include, by way of example and not limitation, polyesters such as polyglycolides, polylactides and polylactic polyglycolic acid copolymers ("PLGA") (Langer and Folkman, 1976, *Nature* 263:797–800); polyethers such as polycaprolactone ("PCL"); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers.

It is to be understood that virtually any polymer that is now known or that will be later developed and that may be suitable for the sustained or controlled release of nucleic acids may be employed in the present invention.

In preferred embodiments, the biocompatible biodegradable polymer is a copolymer of glycolic acid and lactic acid ("PLGA") having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

The length of the period of continuous sustained or controlled release of nucleic acids from the matrix according to the invention will depend in large part on the MW of the polymer and the composition ratio of lactic acid/glycolic acid. Generally, a higher ratio of lactic acid/glycolic acid, such as for example 75/25, will provide for a longer period of controlled of sustained release of the nucleic acids, whereas a lower ratio of lactic acid/glycolic acid will provide for more rapid release of the nucleic acids. Preferably, the lactic acid/glycolic acid ratio is 50/50.

The length of period of sustained or controlled release is also dependent on the MW of the polymer. Generally, a higher MW polymer will provide for a longer period of controlled or sustained release. In the case of preparing, for example, matrices providing controlled or sustained release for about three months, when the composition ratio of lactic acid/glycolic acid is 100/0, the preferable average MW of polymer ranges from about 7,000 to 25,000; when 90/10, from about 6,000 to 30,000; and when 80/20, from about 12,000 to 30,000.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., i J. Surg. Res. 47:74–80, 1989. SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use.

Another particular example of a suitable material is fibrous collagen, which may be lyophilized following extraction and partial purification from tissue and then sterilized. Matrices may also be prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527, each incorporated herein by reference.

In addition, lattices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which repair cells may migrate. Collagen matrices, such as those disclosed in Bell, U.S. Pat. No. 4,485,097, may also be used as a matrix material.

The various collagenous materials may also be in the form of mineralized collagen. For example, the fibrous collagen implant material termed UltraFiber™, as may be obtained from Norian Corp. (1025 Terra Bella Ave., Mountain View, Calif., 94043), may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils. Such a formulation may be employed in the context of delivering a nucleic acid segment to a central nervous system site.

At least 20 different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from bovine tendon may be purchased from, e.g., Collagen Corporation. As another example, autologous extracellular matrix material, including but not limited to products of biopsy explants cultivated ex vivo, may also be prepared from patient tissue for production of GAM. (See, e.g., U.S. Pat. No. 5,332,802 and references cited therein; West et al., *Dermatol. Surg.* 24:510–512, 1998; Staskowski et al., *Otolaryngol Head Neck Surg.* 118(2):187–190, 1998; Rogalla, *Minim Invasive Surg. Nurs.* 11(2):67–69, 1997.) Any form of recombinant collagen may also be employed, as may be obtained from a collagen-expressing recombinant host cell, including bacterial yeast, mammalian, and insect cells. When using collagen an a matrix material it may be advantageous to remove what is referred to as the "telopeptide" which is located at the end of the collagen molecule and is known to induce an inflammatory response.

GAM may also be produced using fibrin matrices, the formation of which can be induced by contacting thrombin with a plasma protein fraction containing fibrinogen and factor XIff. The use of these plasma components to produce biocompatible matrices is well known, and may be provided, for example, by the TISEEL™ kit available from Immuno AG (Vienna, Austria). The person having ordinary skill in the art will be familiar with these and other matrix materials suitable for making GAMs within the scope and spirit of the present invention.

d. Preparation of the Gene Activated Matrices

In preferred embodiments, compositions of either or both biological and synthetic matrices and DNA may be lyophilized together to form a dry pharmaceutical powder. The gene activated matrix may be rehydrated prior to implantation in the body, or alternatively, the gene activated matrix may become naturally rehydrated when placed in the body. The amount of DNA, and the amount of contact time required for incorporation of the DNA into the matrix, will depend on the type of matrix used and can be readily determined by one of ordinary skill in the art without undue experimentation. Alternatively, the DNA may be encapsulated within a matrix of synthetic polymers, such as, for example, block copolymers of polylactic-polyglycolic acid (See Langer and Folkman, *Nature* 263:797–800, 1976, which is incorporated herein by reference). Again, these parameters can be readily determined by one of ordinary skill in the art without undue experimentation. For example, the amount of DNA construct that is applied to the matrix will be determined considering various biological and medical factors. One would take into consideration the particular gene, the matrix, the site of the wound, the mammalian host's age, sex and diet and any further clinical factors that may effect wound healing such as the serum levels of various factors and hormones.

In additional embodiments of the invention, matrix or implant material is contacted with the DNA encoding a therapeutic product of interest by soaking the matrix material in a recombinant DNA stock solution.

In some instances medical devices such as implants, sutures, wound dressings, etc. may be coated with the nucleic acid compositions of the invention using conventional coating techniques as are well known in the art. Such methods include, by way of example and not limitation, dipping the device in the nucleic acid composition, brushing the device with the nucleic acid composition and/or spraying the device with the aerosol nucleic acid compositions of the invention. The device is then dried, either at room temperature or with the aid of a drying oven, optionally at reduced pressure. A preferred method for coating sutures is provided in the examples.

For sutures coated with a polymeric matrix containing plasmid DNA, applicants have discovered that applying a coating composition containing a total of about 0.01 to 10 mg plasmid DNA and preferably about 1 to 5 mg plasmid DNA, to a 70 cm length of suture using about 5 to 100, preferably about 5 to 50, and more preferably about 15 to 30 coating applications yields a therapeutically effective and uniform coating.

In a particularly preferred embodiment, the invention provides coated sutures, especially sutures coated with a polymeric matrix containing nucleic acids encoding therapeutic proteins that stimulate wound healing in vivo.

In another particularly preferred embodiment, a viable cell is introduced or incorporated into the GAM as a support cell. Without wishing to be bound by theory, the presence of a support cell as a component of a GAM may in certain situations influence the ability of the GAM to promote neuronal regeneration and/or neuronal survival, such as may be desirable at an NS lesion site. Support cells that may be useful according to this embodiment of the invention include but need not be limited to Schwann cells, oligodendrocytes, astrocytes, microglial cells, fibroblasts, macrophages or inflammatory cells such as macrophages, neutorphils, monocytes, granulocytes and lymphocytes. Those familiar with the art will appreciate that in various wound healing contexts including those involving NS, these and other support cells may play a contributory role in the generation of a favorable environment for promoting neuronal survival and/or axonal generation and/or axonal regeneration. A GAM containing support cells may also be referred to herein as a mixed GAM.

Sutures which may be coated in accordance with the methods and compositions of the present invention include any suture of natural or synthetic origin. Typical suture materials include, by way of example and not limitation, silk; cotton; linen; polyolefins such as polyethylene and polypropylene; polyesters such as polyethylene terephthalate; homopolymers and copolymers of hydroxycarboxylic acid esters; collagen (plain or chromicized); catgut (plain or chromicized); and suture-substitutes such as cyanoacrylates. The sutures may take any convenient form such as braids or twists, and may have a wide range of sizes as are commonly employed in the art.

The advantages of coated sutures, especially sutures coated with a polymeric matrix containing nucleic acids encoding therapeutic proteins that stimulate wound healing or inhibit fibrosis cover virtually every field of surgical use in humans and animals.

e. Uses of the Gene Activated Matrix

The GAM is applicable to a wide variety of tissue repair and wound healing situations in human medicine. These include, but are not limited to, regeneration of NS neural connections at lesion sites and may also include bone repair, tendon repair, ligament repair, blood vessel repair, skeletal muscle repair, and skin repair. For example, using the gene activated matrix technology, neuronal therapeutic factors may be synthesized in axotomized neurons that have been transfected by retrograde axonal delivery of neuronal therapeutic agent encoding genes recovered from a GAM. The therapeutic agents may direct ordered neurite extension along axonal projection tracts, leading to reestablishment of neural connections to distal targets. Such connections may in turn restore the retrograde flow of neurotrophic factors to the perikaryon upon which neuronal networks depend. The end result is the augmentation of tissue repair and regeneration.

The GAM also may be useful when the clinical goal is to block a disease process, thereby allowing natural tissue healing to take place. Alternatively, the GAM may be used to replace a genetically defective protein function, or to promote neuronal axon regeneration instead of scar matrix deposition that might otherwise occur in the course of natural tissue remodeling without clinical intervention.

NS lesions may arise from traumatic/contusion-compression, transection or other physical injury, or alternatively, from tissue damage either induced by, or resulting from, a surgical procedure, from vascular pharmacologic or other insults including hemorrhagic or ischemic damage, or from neurodegenerative or other neurological diseases. The gene activated matrix of the invention can be transferred to the patient using various techniques. For example, matrices can be transferred directly to the site of the wound by the hand of the physician, either as a therapeutic implant or as a coated device (e.g., suture, coated implant, etc.).

The process of wound healing is a coordinated sequence of events which includes, hemorrhage, clot formation, dissolution of the clot with concurrent removal of damaged tissue, and deposition of granulation tissue as initial repair material. The granulation tissue is a mixture of fibroblasts and capillary blood vessels. The wound healing process involves diverse cell populations including endothelial cells, stem cells, macrophages and fibroblasts. The regulatory factors involved in wound repair are known to include systemic hormones, cytokines, enzymes, growth factors, extracellular matrix proteins and other proteins that regulate growth and differentiation.

One important feature of the present invention is that the formation of scar tissue at the site of the wound may be regulated by the selective use of gene activated matrices. The formation of scar tissue may be regulated by controlling the levels of therapeutic protein expressed, for example, by using GAMs containing DNA constructs encoding negative regulators of granulation tissue (scar) deposition. In cases of traumatic NS damage it is especially desirable to inhibit the formation of scar tissue to permit axonal regrowth along projection tracts and to discourage localized accumulations of neurotrophic factors.

The methods of the present invention include the grafting or transplantation of the matrices containing the DNA of interest into the host. Procedures for transplanting the matrices may include surgical placement, or injection, of the matrices into the host. In instances where the matrices are to be injected, the matrices are drawn up into a syringe and injected into a patient at the site of the lesion. Multiple injections may be made at such sites. Alternatively, the matrices may be surgically placed at the site of the lesion. The amount of matrices needed to achieve the purpose of the present invention i.e., stimulation of NS axonal regeneration, is variable depending on the size, age and weight of the host.

According to the present invention, when a gene activated matrix is transferred to a host, for example, by injection, implantation or surgery, axonal regenerative activity is preferably sufficient enough to facilitate neuron-GAM interaction. This is a preferred condition for induction of the delivery of agents for neuronal regeneration and survival by retrograde axonal transport. In the absence of such ongoing axonal regenerative activity, it is within the scope of the invention to provide agents that stimulate neurons to encourage neuron-GAM interaction and promote axonal uptake of therapeutic constructs and/or complexes. Such stimulatory agents are known in the art and may include agents that specifically stimulate neurons (e.g., neurotrophins) and agents that non-specifically promote any cellular uptake of complexes, including but not limited to inducers of membrane permeability; inducers of endocytic, plasma membrane biogenesis and recycling activities; ionophores, channel blockers and membrane depolarizing agents; signal transduction molecules, gene activators, metalloproteases or any other agent that may transiently rescue an injured neuron that is not actively engaged in axonal regeneration. Physical or mechanical intervention may also effect neuron-GAM interaction, induction of axonal regenerative activity and/or axonal uptake of therapeutic constructs or complexes, including, for example, resection of the nerve tract proximal to the original lesion site to restimulate regeneration. In any case, axonal regenerative activity that leads to GAM invasion by the growing axon may be a preferred embodiment of the present invention.

Conduits

A conduit or nerve regeneration channel may be formulated using any biocompatible matrix material containing DNA encoding a therapeutic agent of interest as described herein, for example therapeutic proteins, transcriptional products, antisense nucleic acids or ribozymes, and used in accordance with the invention. The device may be formed so as to receive one or more ends of a severed or damaged nerve, for example, from either side of a lesion point. The conduit, for example a tubular semipermeable device, a hollow cylinder or a device having some other configuration that those skilled in the art will appreciate as suitable for a particular use of the conduit, defines a lumen through which axons may regenerate, including regeneration that leads to reestablishment of neural networks and restoration of motor and/or sensory function, as described herein. The conduit allows the diffusion or dispersion, inter alia, of nutrients, metabolites and/or the gene-activated matrix itself to the regenerating nerve site while excluding fibroblasts and other cells that may result in the formation of scar tissue. The conduit, comprising a gene activated matrix as described herein, guides neuron outgrowth from a proximal damaged site to a distal damaged site, thus providing effective enervation of the distal site.

In certain embodiments, the conduit may be multilayered and may comprise, wholly or in part, gene activated matrix material. In one embodiment, the conduit comprising gene activated matrices of the invention may be derived from any biocompatible material. Such materials may include, but are not limited to, bioabsorbable or non-bioabsorbable materials. The conduit may be derived from bioabsorbable polymers or naturally occurring protein, for example, type I collagen, laminin, polyglycolic acid, glycolide trimethylene carbonate (GTMC), poly (L-lactide-co-6-caprolactone), glycoproteins, proteoglycans, heparan sulfate proteoglycan, nidogen, glycosaminoglycans, fibronectin, epidermal growth factor, fibroblast growth factor, nerve growth factor, cytokines, DNA encoding growth factors or cytokines, or combinations thereof.

In a further embodiment, the conduit comprising gene activated matrices of the invention may be derived from non-bioabsorbable synthetic polymers, for example polyamide, polyimide, polyurethane, segmented polyurethane, polycarbonate, or silicone. Furthermore, the conduit of the present invention may be comprised of polyamide (nylon) filaments inside silicone tubes. The conduit of the present invention may be further comprised of a microporous synthetic polymer surface etched by a laser. In other further embodiments, the conduit comprising gene activated matrices of the invention may be derived from interposed nerve segments and silicone tube conduit.

In certain other embodiments, the conduit comprising gene activated matrices of the invention may be derived from autogenous or autologous veins that are modified to serve as nerve conduits. According to certain of these embodiments, adventitial wall of the vein combined with gene activated matrix promotes nerve regeneration by providing, inter alia, collagen, laminin, and/or Schwann cells, and promotes increased vascularization of the new nerve. Alternatively, a conduit comprising gene activated matrices of the invention may be derived from collagen, laminin, and Schwann cells.

The conduit may be formulated essentially as described for the gene activated matrix of the present invention, including composition and pore size of the walls. The conduit may be of any shape, dimension, size or configuration, regular or irregular, according to the particular use and/or anatomical location intended. Preferably, the conduit will comprise a lumen having an inner diameter of from about 1 mm to about 1 cm. a wall diameter of from about 0.05 mm to about 1.0 mm, and a length ranging from several millimeters to several centimeters, depending on the extent of the nerve injury.

In a further embodiment, the conduit may be multilayered. A multilayered conduit comprises (1) an inner layer comprising a gene activated matrix with a pore size in the range of from about 0.006 μm to about 5.0 μm that selectively allows the diffusion of DNA encoding neuronal therapeutic factors, while preventing infiltration, invasion or diffusion of fibroblasts and/or other scar-forming cells; and (2) a substantially porous outer layer.

Further descriptions of conduits are contained in U.S. Pat. Nos. 4,877,029, 4,962,146, 5,019,087, and 5,026,381, each of which is herein incorporated by reference in its entirety.

2. NUCLEIC ACID-CONTAINING CONSTRUCTS AND COMPOSITIONS a. Therapeutic DNA

The present invention provides compositions and methods for NS neuronal protection, survival and regeneration via axonal delivery of therapeutic DNAs, as described above. DNA molecules that encode therapeutic products, which are also referred to herein as neuronal therapeutic encoding agents, may in certain embodiments be axonally delivered and retrogradely transported to the cell body of the neuron, as also described above. According to the present invention, neuronal therapeutic encoding agents are delivered to the neuronal axon, or to non-neuronal cell types that can contribute to NS repair, via a gene activated matrix. The neuronal therapeutic encoding agent thus comprises an inactive prodrug that is transcribed and translated within a neuronal cell, to produce an active neuronal therapeutic agent, for example a neurotrophic protein factor. The active neuronal therapeutic agent (e.g., neurotrophic factor) stimulates axonal outgrowth into the gene activated matrix, which may then deliver more neuronal therapeutic encoding agent (e.g., therapeutic DNA prodrug) that is expressed to provide additional active agent. Upon activation of the growth response, neurons may secrete matrix degrading enzymes to facilitate axonal regrowth through the wound. By using a GAM to deliver to the lesion site a neuronal therapeutic encoding agent instead of a neuronal therapeutic agent (such as a neurotrophic factor), the present invention thus overcomes problems in the prior art relating to axonal entrapment, by reducing or eliminating the formation of neurotrophic factor sinks.

Molecules that encode therapeutic products, which are also referred to herein as neuronal therapeutic agent encoding nucleic acids, are molecules that effect a treatment upon or within a neuronal cell, generally by modifying gene transcription of translation. Therapeutic nucleic acids of the present invention may be used in the context of "positive" or "negative" gene therapy, depending on the effect one seeks to achieve.

For example, a therapeutic nucleotide sequence may encode all or a portion of a gene. If it encodes all (or the most critical functional portions) of a gene, it may effect genetic therapy by serving as a replacement for a defective gene. Such a sequence may also function by recombining with DNA already present in a cell, thereby replacing a defective portion of a gene.

A variety of positive gene therapy applications and therapeutic gene products are described herein and include such diverse applications as the promotion of wound healing, the stimulation of neuronal survival and axonal generation/ regeneration, and the like. The replacement of a defective or nonfunctional gene with one that produces the desired gene product is also considered "positive" gene therapy, whether one is replacing a dysfunctional or nonfunctional regulatory sequence or a sequence that encodes a structural protein.

Similarly, "negative" gene therapy is encompassed by the present invention as well. Thus, therapeutic nucleic acids of the present invention may encode products that, for example, inhibit fibrosis, extracellular matrix deposition and/or scar tissue formation. Therapeutic nucleic acids, including neuronal therapeutic encoding agents of the present invention, may also encode decorin, a proteoglycan known to inhibit TGF-β1. In a rat model of glomerulonephritis, fibrosis is mediated by TGF-β1. In a gene therapy application, delivering decorin cDNA to the muscle results in a marked therapeutic effect on fibrosis induced by glomerulonephritis (Isaka et al., 1996, *Nature Medicine* 2:418–423).

Further details regarding both positive and negative gene therapy applications are set forth below in subsequent sections of the specification. The following illustrations are thus intended to be exemplary and not limiting.

i. DNA Encoding Neurotrophic Agents (a) Neuronal Therapeutic Encoding Agents

Nucleic acids for delivery include nucleic acid molecules that encode neuronal therapeutic agents, which may further include proteins to promote neuronal growth and/or survival. For example, in NS injury neuronal cells may fail to regenerate axons over a sufficient distance to re-establish neural connections and restore the retrograde delivery of neurotrophic factors from distal neuronal targets to the perikarya. A construct that directs neuronal expression of one or more neurotrophins, alone or in combination with neurotrophin or FGF protein to promote short-term neuronal survival, can be used to combat the effects of axotomy.

Examples of neuronal therapeutic encoding agents include growth factors and neurotrophic agents that promote neuronal growth and/or survival. Such examples include, but are not limited to, nerve growth factor (NGF), brain-derived neurotrophic factor (BDNF), cardiotrophin-1 (CT-1), choline acetyltransferase development factor (CDF), ciliary neurotrophic factor (CNTF) fibroblast growth factor-1 (FGF-1), FGF-2, FGF-5, glial cell-line-derived neurotrophic factor (GDNF), insulin, insulin-like growth factor-1 (IGF-1), IGF-2, interleukin-6 (IL-6), leukemia inhibitor factor (LIF), neurite promoting factor (NPF), neurotrophin-3 (NT-3), NT-4, platelet-derived growth factor (PDGF), protease nexin-1 (PN-1), S-100, transforming growth factorβ (TGF-β), decorin, anti-TGF-beta antibodies, mutated TGF-beta, and vasoactive intestinal peptide (VIP). (Oppenheim, 1996, *Neuron* 17:195–197.)

The neuronal therapeutic-encoding genes of the present invention may include genes that encode neuronal therapeutic agents that are secreted, or that are not secreted, or that are targeted for localization to specific subcellular compartments within the cell. Nucleic acid sequences encoding peptides that direct intracellular sorting of newly synthesized polypeptides to secretory pathways or to residence in particular intracellular compartments are known and are within the scope of the present invention.

Thus, for example, nucleic acid constructs that are neuronal therapeutic-encoding agents may contain sequences encoding peptides that direct an encoded neuronal therapeutic agent to be retained in the cytosol, to reside in the lumen of the endoplasmic reticulum (ER), to be secreted from a cell via the classical ER-Golgi secretory pathway, to be incorporated into the plasma membrane, to associate with a specific cytoplasmic component including the cytoplasmic domain of a transmembrane cell surface receptor or to be directed to a particular subcellular location by a known intracellular protein sorting mechanism with which those skilled in the art will be familiar. Such intracellular protein sorting peptide sequences may also be present in ligands or nucleic acid binding domains that are provided by the present invention.

In one embodiment of this aspect of the invention, neuronal therapeutic encoding agents may be nucleic acid molecules that encode neuronal therapeutic agents that are ordinarily secretory proteins, but from which sequences encoding secretory "signal" peptides have been deleted to prevent such neuronal therapeutic agents from being secreted via the classical ER-Golgi protein secretory pathway.

Without wishing to be bound by theory, such neuronal therapeutic encoding agents are believed to encode neuronal therapeutic agents that may be useful in the present invention because they may not be secreted by cells expressing the delivered nucleic acids. Such agents may be particularly useful to overcome the problem of extracellular neurotrophic factor sinks that give rise to entrapment of regenerating axons, as described above. Such agents may also be useful where they may exert their neurotrophic effects via intracellular interactions with neuronal components. In this scheme, the agents provided by the present invention may reflect a departure from currently accepted models of neurotrophic factor activity, which require binding interaction between an extracellular neurotrophic factor and an exteriorly disposed neuronal cell surface receptor.

Neuronal therapeutic agents lacking secretory signal sequences and that are the expressed products of neuronal therapeutic-encoding agents delivered to cells according to the present invention may further be useful where the ligand may be bound and internalized by both neuronal and non-neuronal cell types, neither of which is capable of secreting the expressed neuronal therapeutic agent, but where the neuronal therapeutic agent as an intracellular component may exert only neurotrophic/neuronal therapeutic effects that promote axonal regeneration. According to this non-limiting model, cell surface receptors for ligands of the invention need not be absolutely restricted in their expression to neuronal cell surfaces, because non-neuronal cells at or near a NS lesion site would not be able to secrete the encoded neuronal therapeutic agents and therefore cannot generate neurotrophic factor sinks that can lead to undesirable axonal entrapment, as described above. These and other advantages of neuronal therapeutic-encoding agents lacking nucleic acid sequences that encode secretory signal sequences will be appreciated by those skilled in the art.

(b) Other Neuronal Therapeutic Agents

In the context of treatment of neurons following NS injury that may result from physical injury, neurological diseases or neurodegenerative diseases including autoimmune and/or inflammatory diseases, or other trauma, it may be useful to specifically inhibit or interfere with certain biological responses to such injury. For example, as described above, various cell types in an affected tissue may participate in fibrotic scar deposition that may, inter alia, lead to undesirable growth factor sinks and may further present impediments to NS regeneration and reestablishment of neural networks.

As another example, in neurodegenerative disease central nervous system (CNS) injury wherein CNS microglia contribute to the pathogenesis, neuronal therapeutic agents that are targeted to and capable of regulating the biological activity of such microglia may be useful. For instance, neuronal therapeutic agents that are targeted to regulate the viability, biosynthetic potential or proliferative capacity of, e.g., microglia, or neuronal therapeutic encoding agents that deliver genes able to regulate one or more pathogenic gene products of, e.g., microglia, are non-limiting illustrations of additional agents according to the invention that may be useful. Examples of target microglia gene products that may impede reestablishment of neural connectivity following CNS and or NS injury include but need not be limited to TGF-β, connective tissue growth factor (CTGF), IL-1 receptor antagonist (IL-1RA) (see, e.g., Streit, *In CNS Injuries: Cellular Responses and Pharmacological Strategies*, M. Berry and A. Logan, eds., 1998, CRC Press, Boca Raton, Fla.), macrophage/microglial stimulatory factor (MSF), macrophage/microglial inhibitory factor (MWF) and microglia-derived proteases (e.g., metalloproteases, plasminogen activator).

It should expressly be understood, however, that simply because a cell or tissue is described herein as "targeted" does not necessarily imply that a targeting ligand is a required component of a therapeutic construct according to the present invention. Therapeutic nucleotide sequences/constructs are deliverable in a variety of forms, as disclosed herein, e.g., in the presence of—or absence of—a targeting ligand.

The constructs provided herein may also be used to deliver a ribozyme, antisense molecule, and the like to targeted cells, for example, to specifically inhibit activation of one or more genes following NS injury. These nucleic acids may be present in the complex of ligand and nucleic acid binding domain or encoded by a nucleic acid in the complex. Alternatively, the nucleic acid may be directly linked to the ligand. Such products include antisense RNA, antisense DNA, ribozymes, triplex-forming oligonucleotides, and oligonucleotides that bind proteins. The nucleic acids can also include RNA trafficking signals, such as viral packaging sequences (see, e.g., Sullenger et al. (1994) *Science* 262:1566–1569).

Nucleic acids and oligonucleotides for use as described herein can be synthesized by any method known to those of skill in this art (see, e.g., WO 93/01286, U.S. application Ser. No. 07/723,454; U.S. Pat. No. 5,218,088; U.S. Pat. No. 5,175,269; U.S. Pat. No. 5,109,124). Identification of oligonucleotides and ribozymes for use as antisense agents and DNA encoding genes for delivery for genetic therapy involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrehedron Lett.* 28:3539–3542 (1987); Miller et al., *J. Am. Chem. Soc.* 93:6657–6665 (1971); Stec et al., *Tetrehedron Lett.* 26:2191–2194 (1985); Moody et al., *Nucl. Acids Res.* 12:4769–4782 (1989); Uznanski et al., *Nucl. Acids Res.* (1989); Letsinger et al., *Tetrahedron* 40:137–143 (1984); Eckstein, *Annu. Rev. Biochem.* 54:367–402 (1985); Eckstein, *Trends Biol. Sci.* 14:97–100 (1989); Stein In: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as MRNA or DNA. When bound to mRNA that has complementary sequences, antisense prevents translation of the MRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary to or bind the sense strand of DNA or mRNA that encodes a protein involved in neuronal cell degeneration (e.g., proteins of apoptosis pathways) or a protein mediating any other unwanted process such that inhibition of translation of the protein is desirable.

A ribozyme is a molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave such transcript (see, e.g., U.S. Pat. No. 5,272,262; U.S. Pat. No. 5,144,019; and U.S. Pat. Nos. 5,168,053, 5,180,818, 5,116,742 and 5,093,246 to Cech etal.). Any such ribozyme or nucleic acid encoding the ribozyme may be delivered to a cell via the use of a construct as disclosed herein.

Ribozymes, deoxyribozymes and the like may be delivered to the treated or targeted cells by DNA encoding the ribozyme linked to a eukaryotic promoter, such as a eukaryotic viral promoter, such that upon introduction into the nucleus, the ribozyme will be directly transcribed. Ribozyme-containing constructs may further comprise a targeting ligand and/or a nuclear translocation sequence. The latter may be included as part of the ligand, as part of a linker between the ligand and nucleic acid binding domain, or it may be attached directly to the NABD.

ii. Methods of Preparing DNA for Use in Compositions

A therapeutic nucleotide composition, which may be a neuronal therapeutic encoding agent of the present invention, comprises a nucleotide sequence encoding a therapeutic molecule as described herein. As noted above, a therapeutic nucleotide composition or neuronal therapeutic encoding agent may further comprise an enhancer element or a promoter located 5' to and controlling the expression of said therapeutic nucleotide sequence or gene. The promoter is a DNA segment that contains a DNA sequence that controls the expression of a gene located 3' or downstream of the promoter. The promoter is the DNA sequence to which RNA polymerase specifically binds and initiates RNA synthesis (transcription) of that gene, typically located 3' of the promoter.

The subject therapeutic nucleotide composition comprises a nucleic acid molecule, which in certain aspects of the invention further comprises at least 2 different operatively linked DNA segments. The DNA can be manipulated and amplified by PCR and by using the standard techniques described in *Molecular Cloning: A Laboratory Manual*, 2nd Edition, Maniatis et al., eds., Cold Spring Harbor, N.Y. (1989). Typically, to produce a therapeutic nucleotide composition of the present invention, the sequence encoding the selected therapeutic composition and the promoter or enhancer are operatively linked to a vector DNA molecule capable of autonomous replication in a cell either in vivo or in vitro. By operatively linking the enhancer element or promoter and the nucleotide sequence encoding the therapeutic nucleotide composition to the vector, the attached segments are replicated along with the vector sequences. Thus, a recombinant DNA molecule (rDNA) of the present invention is a hybrid DNA molecule comprising at least 2 nucleotide sequences not normally found together in nature.

The therapeutic nucleotide composition of the present invention is from about 20 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Most preferred is a nucleic acid molecule from about 50 pairs to about 4,000 base pairs in length. The therapeutic nucleotide can be a gene or gene fragment that encodes a protein or peptide that provides the desired therapeutic effect. Alternatively, the therapeutic nucleotide can be a DNA or RNA oligonucleotide sequence that exhibits enzymatic therapeutic activity. Examples of the latter include antisense oligonucleotides that will inhibit the transcription of deleterious genes or ribozymes that act as site-specific ribonucleases for cleaving selected mutated gene sequences. In another variation, a therapeutic nucleotide sequence of the present invention may comprise a DNA construct capable of generating therapeutic nucleotide molecules, including ribozymes and antisense DNA, in high copy numbers in target cells, as described in published PCT application No. WO 92/06693 (the disclosure of which is incorporated herein by reference). Exemplary and preferred nucleotide sequences encode an expressible peptide, polypeptide or protein, and may further include an active constitutive or inducible promoter sequence.

A regulatable promoter is a promoter where the rate of RNA polymerase binding and initiation is modulated by external stimuli. Such stimuli include compositions light, heat, stress and the like. Inducible, suppressible and repressible promoters are regulatable promoters. Regulatable promoters may also include tissue specific promoters. Tissue specific promoters direct the expression of that gene to a specific cell type. Tissue specific promoters cause the gene located 3' of it to be expressed predominantly, if not exclusively in the specific cells where the promoter expressed its endogenous gene. Typically, it appears that if a tissue-specific promoter expresses the gene located 3' of it at all, then it is expressed appropriately in the correct cell types as has been reviewed by Palmiter et al., *Ann. Rev. Genet.* 20:465–499 (1986).

When a tissue specific promoter controls the expression of a gene, that gene will be expressed in a small number of tissues or cell types rather than in substantially all tissues and cell types. Examples of tissue specific promoters include the glial fibrillary acid protein (GFAP) gene promoter (Brenner and Messing, 1996, *Methods: A companion to Methods in Enzymology* 10:351–364); the GAP43 promoter (deGroen et al., 1995, *J. Mol. Neurosci*, 66:109–119); the immunoglobulin promoter described by Brinster et al., *Nature* 306:332–336 (1983) and Storb et al., *Nature* 310:238–231 (1984); the elastase-I promoter described by Swift et al., *Cell* 38:639–646 (1984); the globin promoter described by Townes et al., *Mol. Cell. Biol.* 5:1977–1983 (1985), and Magram et al., *Mol. Cell. Biol.* 9:4581–4584 (1989), the insulin promoter described by Bucchini et al., *PNAS USA* 83:2511–2515 (1986) and Edwards et al., *Cell* 58:161 (1989); the immunoglobulin promoter described by Ruscon et al., *Nature* 314:330–334 (1985) and Grosscheld et al., *Cell* 38:647–658 (1984); the alpha actin promoter described by Shani, *Mol. Cell. Biol.* 6:2624–2631 (1986); the alpha crystalline promoter described by Overbeek et al., *PNAS USA* 82:7815–7819 (1985); the prolactin promoter described by Crenshaw et al., *Genes and Development* 3:959–972 (1989); the proopiomelanocortin promoter described by Tremblay et al., *PNAS USA* 85:8890–8894 (1988); the beta-thyroid stimulating hormone (BTSH) promoter described by Tatsumi et al., *Nippon Rinsho* 47:2213–2220 (1989); the mouse mammary tumor virus (MMTV) promoter described by Muller et al., *Cell* 54:105 (1988); the albumin promoter described by Palmiter et al., *Ann. Rev. Genet.* 20:465–499 (1986); the keratin promoter described by Vassar et al., *PNAS USA* 86:8565–8569 (1989); the osteonectin promoter described by McVey et al., *J. Biol. Chem.* 263:11,111–11,116 (1988); the prostate-specific promoter described by Allison et al., *Mol. Cell. Biol.* 9:2254–2257 (1989); the opsin promoter described by Nathans et al., *PNAS USA* 81:4851–4855 (1984); the olfactory marker protein promoter described by Danciger et al., *PNAS USA* 86:8565–8569 (1989); the neuron-specific enolase (NSE) promoter described by Forss-Pelter et al., *J. Neurosci. Res.* 16:141–151 (1986); the L-7 promoter described by Sutcliffe, *Trends in Genetics* 3:73–76 (1987) and the protamine 1 promoter described Peschon et al., *Ann. New York Acad. Sci.* 564:186–197 (1989) and Braun et al., *Genes and Development* 3:793–802 (1989).

In various alternative embodiments of the present invention, therapeutic sequences and compositions useful for practicing the therapeutic methods described herein are contemplated. Therapeutic compositions of the present invention may contain a physiologically tolerable carrier together with one or more therapeutic nucleotide sequences of this invention, dissolved or dispersed therein as an active ingredient. In a preferred embodiment, the composition is not immunogenic or otherwise able to cause undesirable side effects when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, or as pastes, however, solid forms suitable for solution, or suspensions, in liquid prior to use can also be prepared. The preparation can also be emulsified, or formulated into pastes, suppositories, ointments, creams, dermal patches, or the like, depending on the desired route of administration.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof, including vegetable oils, propylene glycol, polyethylene glycol and benzyl alcohol (for injection or liquid preparations); and Vaseline, vegetable oil, animal fat and polyethylene glycol (for externally applicable preparations). In addition, if desired, the composition can contain wetting or emulsifying agents, isotonic agents, dissolution promoting agents, stabilizers, colorants, antiseptic agents, soothing agents and the like additives (as usual auxiliary additives to pharmaceutical preparations), pH buffering agents and the like which enhance the effectiveness of the active ingredient.

The therapeutic compositions of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Physiologically tolerable carriers may also include compositions that mimic relevant tissue fluids, e.g., artificial cerebral spinal fluid, or artificial blood.

Liquid compositions can also contain liquid phases in addition to and to the exclusion of water. Exemplary of such additional liquid phases are glycerin, vegetable oils such as cottonseed oil, and water-oil emulsions.

A therapeutic composition typically contains an amount of a therapeutic nucleotide sequence of the present invention sufficient to deliver a therapeutically effective amount to the target tissue, typically an amount of at least 0.1 weight percent to about 90 weight percent of therapeutic nucleotide sequence per weight of total therapeutic composition. A weight percent is a ratio by weight of therapeutic nucleotide sequence to total composition. Thus, for example, 0.1 weight percent is 0.1 grams of DNA segment per 100 grams of total composition.

The therapeutic nucleotide compositions comprising synthetic oligonucleotide sequences of the present invention can be prepared using any suitable method, such as, the phosphotriester or phosphodiester methods. See Narang et al., *Meth. Enzymol.* 68: 90, (1979); U.S. Pat. No. 4,356,270; and Brown et al., *Meth. Enzymol.* 68:109 (1979). For therapeutic oligonucleotides sequence compositions in which a family of variants is preferred, the synthesis of the family members can be conducted simultaneously in a single reaction vessel, or can be synthesized independently and later admixed in preselected molar ratios.

For simultaneous synthesis, the nucleotide residues that are conserved at preselected positions of the sequence of the family member can be introduced in a chemical synthesis protocol simultaneously to the variants by the addition of a single preselected nucleotide precursor to the solid phase oligonucleotide reaction admixture when that position number of the oligonucleotide is being chemically added to the growing oligonucleotide polymer. The addition of nucleotide residues to those positions in the sequence that vary can be introduced simultaneously by the addition of amounts, preferably equimolar amounts, of multiple preselected nucleotide precursors to the solid phase oligonucleotide reaction admixture during chemical synthesis. For example, where all four possible natural nucleotides (A,T,G and C) are to be added at a preselected position, their precursors are added to the oligonucleotide synthesis reaction at that step to simultaneously form four variants.

This manner of simultaneous synthesis of a family of related oligonucleotides has been previously described for the preparation of "degenerate oligonucleotides" by Ausubel et al, in *Current Protocols in Molecular Biology, Suppl.* 8:2.11.7, John Wiley & Sons, Inc., N.Y. (1991), and can readily be applied to the preparation of the therapeutic oligonucleotide compositions described herein.

Nucleotide bases other than the common four nucleotides (A,T,G or C), or the RNA equivalent nucleotide uracil (U), can be used in the present invention. For example, it is well known that inosine (I) is capable of hybridizing with A, T and G, but not C. Thus, where all four common nucleotides are to occupy a single position of a family of oligonucleotides, that is, where the preselected therapeutic nucleotide composition is designed to contain oligonucleotides that can hybridize to four sequences that vary at one position, several different oligonucleotide structures are contemplated. The composition can contain four members, where a preselected position contains A,T,G or C. Alternatively, the composition can contain two members, where a preselected position contains I or C, and has the capacity the hybridize at that position to all four possible common nucleotides. Finally, other nucleotides may be included at the preselected position that have the capacity to hybridize in a non-destabilizing manner with more than one of the common nucleotides in a manner similar to inosine.

3. TESTING OF CONSTRUCTS

The reprogrammed recombinant nucleic acid, synthetic DNA or viral delivery vehicles may be assessed in any number of in vitro model systems. In particular, target cells are grown in culture and incubated with the nucleic acid delivery vehicle. The nucleic acid can encode a reporter, in which case the reporter product is assayed, or a neuronal therapeutic agent, in which case neuronal outgrowth, neurite extension, or another parameter for routinely determining neuronal therapeutic encoding agent expression with which those skilled in the art will be familiar, is measured. Moreover, any assayable gene product can be used. For reporter genes, a wide variety of suitable genes are available. Such reporters include β-galactosidase, alkaline phosphatase, β-glucuronidase, green fluorescent protein, luciferase, large T antigenor any protein for which an antibody exists or can be developed. The choice of a reporter depends, in part, upon the cells being tested. Alternatively, the nucleic acid can encode a neuronal therapeutic agent. Such products include all those described herein.

The delivery vehicles may be assessed in in vitro or in vivo model systems. Generally, in vitro testing in relevant cultured neuronal cells may be used, e.g., retinal ganglion cells, dorsal root ganglion cells, neural progenitor cells or astrocytes. Furthermore, in vivo model systems may include, for example, optic nerve and spinal cord bioassays as described herein or any suitable in vivo model neuronal system with which those having skill in the art are familiar.

a. Targeting Agents

Although the various DNA devices and constructs disclosed herein do not absolutely require the inclusion of a targeting moiety, in various embodiments, inclusion of a targeting agent—e.g., a polypeptide ligand—may be advantageous. Examples of useful ligands are described below for the purpose of illustrating such embodiments, but such examples should not be perceived as limiting the invention to such embodiments alone.

i. Ligands

Ligands according to the present invention are molecules capable of binding interactions with receptors of desired target cells, and may take a variety of forms. Ligands that are most preferred for use in the invention are internalized by target cells subsequent to receptor binding, providing a cellular route of entry for targeted agents of the invention. Ligands may be natural or synthetic molecules and may be subunits, fragments or structurally modified forms of other ligands. Thus, ligands may include, but need not be limited to, proteins, peptides, polypeptides, muteins, fragments or chemical derivatives of proteins, peptides, or polypeptides, other natural or synthetic molecules such as carbohydrates, nucleic acids or their derivatives, lipids or their derivatives, or any other natural or artificial composition that binds to cellular receptors. In many aspects of the invention, preferred ligands bind to receptors on the surfaces of neuronal cells, but the invention need not be so limited.

(a) Ligands that Bind to and are Internalized by Neuronal Cells

As noted above, receptor-binding internalized ligands may be used to deliver nucleic acids, including a neuronal therapeutic-encoding agent, to a cell expressing an appropriate receptor on its cell surface. Numerous molecules that bind specific receptors have been identified and are suitable for use in the present invention. Such molecules include neurotrophic and other neuronal therapeutic factors, which may further include—but which are not limited to—growth factors, cytokines, and antibodies.

Many growth factors and families of growth factors share structural and functional features and may be used in the present invention. Families of growth factors include neurotrophins (NT) such as NT-1, NT-2, NT-3 and NT4/5, where NT-1 is nerve growth factor (NGF) and NT-2 is brain derived neurotrophic factor (BDNF). Additional growth factor families include ciliary neurotrophic factor (CNTF) and related neuropoietic cytokines including leukemia inhibitory factor (LwF) and oncostatin M (OSM); fibroblast growth factors including FGF-1 through FGF-15; pleiotrophins including midkine (Li, *Science* 250:1690, 1990) and heparin binding neurotrophic factor (HBNF, He et al., *J. Neurosci.* 18:3699–3707, 1998); cell surface proteoglycans (see, e.g., Quarto et al., *J. Cell Sci.* 107:3201–3212, 1994); and the epidermal growth factor (EGF) family. These and other soluble factors, such as TGF-α (transforming growth factor), TGF-β and related factors including glial cell line derived neurotrophic factor (GDNF), insulin and insulin-like growth factors (IGF), HB-EGF, cholera toxin B subunit (CTB), neurotensin, bombesin, substance P, neurokinin, tachykinin and other neuropeptides also bind to specific identified receptors on cell surfaces of the NS, including neuronal cell surfaces and may be used in the present invention.

Antibodies that are specific to cell surface molecules expressed by neuronal cells are readily generated as monoclonal antibodies or as polyclonal antisera, or may be produced as genetically engineered immunoglobulins that are designed using methods well known in the art to have desirable properties. For example, by way of illustration and not limitation, recombinant IgGs, chimeric fusion proteins having immunoglobulin derived sequences or "humanized" antibodies may all be used as ligands that bind to and are internalized by neuronal cells according to the invention. Many such antibodies are readily available from a variety of commercial and other sources (e.g., from American Type Culture Collection, Rockville, Md.). Cytokines, including but not limited to interleukins, chemokines, and interferons, may also have specific receptors on one or more cell type found in the NS and may be used as described herein. These and other ligands are discussed in more detail below.

Fragments of ligands described herein may be used within the present invention, so long as the fragment retains the ability to bind to the appropriate cell surface molecule. Likewise, ligands with substitutions or other alterations, but which retain binding ability, may also be used. In general, a particular ligand refers to a polypeptide(s) having an amino acid sequence of the native ligand, as well as modified sequences (e.g., having amino acid substitutions, deletions, insertions or additions compared to the native protein) as long as the ligand retains the ability to bind to its receptor on a neuronal cell and be internalized.

Ligands also encompass muteins that possess the ability to bind to receptor expressing cells and be internalized. The muteins may not be pharmacologically active. Such muteins include, but are not limited to, those produced by replacing one or more of the "native" amino acid residues in a ligand amino acid sequence with a different amino acid, as described herein. Typically, such muteins will have conservative amino acid changes. For example, if the ligand is a polypeptide sequence encoding FGF2, a useful mutein may include a cysteine residue in place of a serine residue. DNA encoding such muteins will, unless modified by replacement of degenerate codons, hybridize under conditions of at least low stringency to native DNA sequence encoding the wild-type ligand.

DNA encoding a ligand may be prepared synthetically based on known amino acid or DNA sequence, isolated using methods known to those of skill in the art (e.g., PCR amplification), or obtained from commercial or other sources. DNA encoding a ligand may differ from "known" or "native" sequences by substitution of degenerate codons or by encoding different amino acids. Differences in amino acid sequences, such as those occurring among the homologous ligand of different species as well as among individual organisms or species, are tolerated as long as the ligand binds to its receptor. Ligands may be isolated from natural sources or made synthetically, such as by recombinant means or chemical synthesis.

(1) Polypeptides Reactive with the FGF Receptor

One family of growth factors that may be used as ligands within the context of the present invention is the fibroblast growth factor (FGF) family. The members of the FGF family have a high degree of amino acid sequence similarities and common physical and biological properties, including the ability to bind to one or more FGF receptors.

This family of proteins includes FGFs designated FGF-1 (acidic FGF (aFGF)), FGF-2 (basic FGF (bFGF)), FGF-3 (int-2) (see, e.g., Moore et al., *EMBO J.* 5:919–924, 1986), FGF-4 (hst-1/K-FGF) (see, e.g., Sakamoto et al., *Proc. Natl. Acad. Sci. USA* 86:1836–1840, 1986; U.S. Pat. No. 5,126,323), FGF-5 (see, e.g., U.S. Pat. No. 5,155,217), FGF-6 (hst-2) (see, e.g., published European Application EP 0 488 196 A2; Uda et al., *Oncogene* 7:303–309, 1992), FGF-7 (keratinocyte growth factor) (KGF) (see, e.g., Finch et al., *Science* 245:752–755, 1985; Rubin et al., *Proc. Natl. Acad. Sci. USA* 86:802–806, 1989; and International Application WO 90/08771), FGF-8 (see, e.g., Tanaka et al., *Proc Natl. Acad. Sci. USA* 89:8528–8532, 1992); FGF-9 (see, Miyamoto et al., *Mol. Cell. Biol.* 13:4251–4259, 1993); FGF-11 (WO 96/39507); FGF-13 (WO 96/39508); FGF-14 (WO 96/39506); and FGF-15 (WO 96/39509).

DNA encoding FGF peptides and/or the amino acid sequences of FGFs are well known. For example, DNA encoding human FGF-1 (Jaye et al., *Science* 233:541–545, 1986; U.S. Pat. No. 5,223,483), bovine FGF-2 (Abraham et al., *Science* 233:545–548, 1986; Esch et al., *Proc. Natl. Acad. Sci. USA* 82:6507–6511, 1985; and U.S. Pat. No. 4,956,455), human FGF-2 (Abraham et al., *EMBO J.* 5:2523–2528, 1986; U.S. Pat. No. 4,994,559; U.S. Pat. No. 5,155,214; EP 470,183B; and Abraham et al., *Quant. Biol.* 51:657–668, 1986) rat FGF-2 (see, Shimasaki et al., *Biochem. Biophys. Res. Comm.*, 1988, and Kurokawa et al., *Nucleic Acids Res.* 16:5201, 1988), FGF-3, FGF-6, FGF-7 and FGF-9 are known (see also U.S. Pat. No. No. 5,155,214; U.S. Pat. No. 4,956,455; U.S. Pat. No. 5,026,839; U.S. Pat. No. 4,994,559, EP 0,488,196 A2, EMBL or GenBank databases, and references discussed herein).

The effects of FGFs are mediated by high affinity receptor tyrosine kinases present on the cell surface of FGF-responsive cells (see, e.g., PCT WO 91/00916, WO 90/05522, PCT WO 92/12948; Imamura et al., *Biochem. Biophys. Res. Comm.* 155:583–590,1988; Huang et al., *J. Biol. Chem.* 261:9568–9571,1986; Partanen et al., *EMBO J.* 10:1347, 1991; and Moscatelli, *J. Cell. Physiol.* 131:123, 1987). Low affinity receptors also appear to play a role in mediating FGF activities. Cell type specific expression of one or more of four FGF receptor genes that have been identified, plus additional receptor heterogeneity generated by alternative RNA splicing of the transcripts of such genes, may provide the basis for differential specificity of FGF family members among different tissues and cells.

For example, by way of illustration and not limitation, FGF-2 may be suitable for use in the present invention as a receptor binding ligand that can be internalized by neuronal cells having surface FGF-2 receptors. At physiologic concentrations FGF-2 may be trophic for injured neurons, while at significantly lower concentrations FGF-2 is not neurotrophic but may be readily internalized via neuronal FGF-2 receptors. Accordingly, the use of sub-neurotrophic FGF-2 concentrations in the present invention may provide a ligand that is not present in sufficient quantities to create an FGF-2 sink, thereby avoiding the problem of axonal entrapment associated with local administration of neurotrophic factors, as discussed above. Those having skill in the art are familiar with routine methods for evaluating the local concentration and bioavailability of FGF-2 provided as a ligand of the invention, for readily detecting FGF-2 internalization by neurons and for determining whether a local FGF-2 sink sufficient to induce axonal entrapment has accumulated. (See, e.g., Logan et al., *Prog. Growth Factor Res.* 5:379–405, 1994.)

(2) Neurotrophins

Neurotrophins (NT) comprise a multifunctional family of structurally related proteins that may be useful as ligands in the present invention. NT regulate the developmental fates of neuronal cells during the formation and differentiation of neural networks, and provide essential stimuli for the maintenance and survival of neural cells. NT may also regulate non-neuronal cells that express cell surface receptors specific for one or more members of the NT family. The neurotrophin family includes nerve growth factor (NGF or NT-1), brain derived neurotrophic factor (BDNF or NT-2), neurotrophin 3 (NT-3), neurotrophin 4 (NT-4/5), and neurotrophin 6 (NT-6). (See, e.g., Oshima et al., in *Growth Factors and Cytokines in Health and Disease*, LeRoith and Bondy, eds., 229–258, 1996 JAI Press, Greenwich, Conn.) Nerve growth factor (NGF/NT-1), the prototype for the neurotrophin family, is a 26 kDa protein homodimer of 121 amino acid polypeptide subunits, each derived from a 241 amino acid precursor. Mature NGF contains three cysteine pairs involved in intrachain disulfide bond formation that is required for biological activity. NGF sequences are highly conserved across species lines. Two distinct receptors for NGF are known. The high affinity NGF receptor trkA, encoded by the trk (tropomyosin receptor kinase) proto-oncogene, is a 140 kDa transmembrane glycoprotein that includes a cytoplasmic domain having tyrosine kinase activity. The trkA receptor is expressed on the surfaces of sensory cranial and dorsal root ganglia neurons, basal forebrain and caudate neurons, and on monocytes. The low affinity NGF receptor, which belongs to the distinct tumor necrosis factor receptor (TNF-R) superfamily, is a 75 kDa transmembrane glycoprotein expressed by Schwann cells, neurons, lymphocytes, bone marrow fibroblasts, keratinocytes and myoepithelium, as well as on various tumor cell surfaces.

NGF exhibits a variety of biological activities within the NS including the CNS, including promotion of neuronal survival following axotomy, inhibition of apoptotic pathways and developmental regulation of neuronal differentiation. (Hagg, in *CNS Injuries: Responses and Pharnacological Strategies* (A. Logan and M. Berry, eds.) 1998 CRC Press, Boca Raton, Fla.; see also Oshima et al., in *Growth Factors in Health and Disease*, LeRoith and Bondy, eds., 229–258, 1996 JAI Press, Greenwich, Conn.; Muller et al., *J. Neurosci. Res.* 38:41, 1994; Morimoto et al., *Neuroreport* 5:954, 1994, Tischler et al., *J. Neurosci.* 13:1533, 1993; Oppenheim, *Ann. Rev. Neurosci.* 14:453, 1991; Hefti, *J. Neruosci.* 6:2155, 1986; Oppenheim et al., *J. Comp. Neurol.* 210:174, 1982; Hamburger et al., *J. Neurosci.* 1:60, 1981.) NGF also appears to play significant roles in the regulation of hematopoiesis and inflammation, including reported modulation and/or stimulation of various lymphoid, myelomonocytic and granulocytic subpopulations.

Like NT-1, the other neurotrophins, brain derived neurotrophic factor (BDNF/NT-2), NT-3, NT4/5 and NT-6, are 26 kDa homodimers that exhibit 50–60% amino acid sequence homology with one another and that possess functional homology as well. (For a review of neurotrophic factors, see Hagg, in *CNS Injuries: Responses and Pharmacological Strategies*, A. Logan and M. Berry, eds., 1998 CRC Press, Boca Raton, Fla.) All neurotrophins bind to the low affinity NGF receptor, while only NT-1 can bind trkA with high affinity. Related to the trkA receptor are the additional neurotrophin receptors trkB, which binds NT-2 and NT-4/5, and trkC, which binds NT-3. (Barbacid, in *Growth Factors and Cytokines in Health and Disease*, LeRoith and Bondy, eds., 259–276, 1996 JAI Press, Greenwich, Conn.; Barbacid, *J. Neurobiol.* 25:1386, 1994; Squinto et al., *Cell* 65:885, 1991; Lamballe et al., *Cell* 66:967, 1991; Klein et al., *Cell* 61:647, 1990; Velenzuela et al., *Neuron* 10:963, 1990.) Glial cell line-derived neurotrophic factor (GDNF) is a neurotrophic factor that may be useful as a ligand in the present invention and that is structurally unrelated to the NT family members. GDNF is a member of the transforming growth factor-β (TGF-β) gene superfamily and may exhibit differential biological activity depending on the types of neurons to which it is exposed. (See, e.g., McPherron et al., in *Growth Factors and Cytokines in Health and Disease*, LeRoith and Bondy, eds., 357–393, 1996 JAI Press, Greenwich, Conn.)

(3) Antibodies and Other Ligands to Neuronal Cell Surface Molecules

As noted above, antibodies that specifically bind to neuronal cell surface molecules may be useful as ligands in the present invention, and may further include monoclonal or polyclonal antibodies, genetically engineered immunoglobulins or other natural, recombinant or synthetic proteins including chimeric fusion proteins that have antibody activity, or fragments of any of these immunoglobulins or immunoglobulin derivatives that specifically bind to neuronal cell surface molecules. Antibodies that are internalized by neuronal cells upon binding to cognate antigen on the neuronal cell surface as provided, as well as antibodies that may require an additional signal to be internalized, including but not limited to a signal that is the result of natural, genetically engineered or synthetic aggregation, crosslinking or induced multivalency, any of which may further include internalization that is induced by the presence of multiple antibody binding sites having specificity for more than one cell surface antigenic determinant, are within the contemplated uses of antibodies as ligands in the present invention.

Genetically engineered antibodies that specifically bind to neuronal cell surface molecules may be useful as ligands in the present invention. For example, bacteriophage display selection methods may be useful for producing single chain Fv immunoglobulins that demonstrate high affinity binding to neuronal cell surface molecules. (see, e.g., U.S. Pat. No. 5,223,409).

Neuronal cell surface molecules, to which antibodies that are to be used as ligands in the invention as described above may specifically bind, may include any cell surface structure present on neurons that can be internalized subsequent to ligand binding, including but not limited to proteins; glycoconjugates including glycoproteins, glycolipids, proteoglycans, glycosaminoglycans and the like; carbohydrates, lipids or other cell surface structures to which antibody may specifically bind. Markers for neuronal cell types, including neuronal cell surface markers, are known in the art and may be readily determined by well known methodologies and reference literature, for example by way of illustration and not limitation Lee et al. (Annu. Rev. Neurosci. 19:187–217, 1996), Martini et al. (Glia 19:298–310, 1997), Rieger-Christ et al. (Front. Biosci. 2:D348-D448, 1997) and Chao (Neuron 9:583–593, 1992). Neuronal cell surface molecules may include, for exarnple, neuronal cell adhesion molecule (NCAM), the polysialylated oligosaccharide moiety of which has been reported to function as an internalizable receptor for an antennapedia homeobox peptide. (Joliot et al., New Biol. (U.S.) 3:1121–1134, 1991) Neuronal cell surface molecules may also include, for example, the ganglioside $GM_1$, which has shown to function as receptor for cholera toxin B chain (see, e.g., Mulhein et al., *J. Membr. Biol.* 109:21, 1989); the proteoglycan syndecan, and various members of the integrin family of cell surface adhesion molecules.

Other receptor-binding ligands may be used in the present invention. Any protein, polypeptide, analogue, or fragment that binds to a neuronal cell-surface receptor and is internalized may be used. These ligands may be produced by recombinant or other means in preparation for conjugation to the nucleic acid binding domain. Ligands for use in the present invention may also be selected by a method such as phage display (see, e.g., U.S. Pat. No. 5,223,409) or variations of phage display with which those of ordinary skill in the art will be familiar, including methods that may be useful for selecting neuronal cell surface receptors having particularly low, particularly high or intermediate binding affinities for neuronal cell surface receptors as those terms are understood by persons of ordinary skill in the art with respect to certain known neuronal cell surface receptors.

The DNA sequences and methods to obtain the sequences of these receptor-binding internalized ligands are well known. For example, these ligands and ligand/receptor pairs include urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L23088), VCAM1/VLA-4 (GenBank Accession Nos. X53051/X16983); E9 antigen (Blann et al., *Atherosclerosis* 120:221, 1996)/TGFβ receptor; Fibronectin (GenBank Accession No. X02761); type I α1-collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); ELF-3, LERTK-2 ligands (GenBank Accession Nos. L37361, U09304) for elk-1(GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $\alpha_v\beta_3$ integrin (GenBank Accession Nos. U07375, L28832). DNA sequences of other suitable receptor-binding internalized ligands may be obtained from GenBank or EMBL DNA databases, reverse-synthesized from protein sequence obtained from PIR database or isolated by standard methods (Sambrook et al., supra) from cDNA or genomic libraries.

b) Modification of Ligands

The ligands for use herein may be customized for a particular application. Briefly, additions, substitutions and deletions of amino acids may be produced by any commonly employed recombinant DNA method.

Modification of the polypeptide may be effected by any means known to those of skill in this art. The preferred methods herein rely on modification of DNA encoding the polypeptide and expression of the modified DNA. DNA encoding one of the receptor-binding internalized ligands discussed above may be mutagenized using standard methodologies. For example, cysteine residues that may be useful to facilitate conjugation, such as formation of constructs or conjugates having a defined molar ratio of constituent polypeptides, can be added to a polypeptide. Conversely, cysteine residues that are responsible for aggregate formation may be deleted or replaced. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of these receptor-binding internalized ligands may be constructed and used. The binding regions of many of these ligands, for example that of FGF, have been delineated. The receptor binding region of FGF2 has been shown to reside between residues 33–77 and between 102–129 of the 155 amino acid form of FGF2, through the use of FGF peptide agonists/antagonists and by mutation analysis. (Baird et al., *PNAS* 85:2324; Erickson et al., *Biochem.* 88:3441). Fragments of ligands may also be shown to bind and internalize by any one of the tests described herein. Modification of DNA encoding ligands may be performed by a variety of methods, including site-specific or site-directed mutagenesis of DNA encoding the protein and the use of DNA amplification methods using primers, as described above.

As noted above, binding to a receptor and subsequent internalization are the only activities required for a ligand to be suitable for use herein. However, some of the ligands are growth factors and may have undesirable biological activities, for example those that are mitogens. Although mature neurons may be generally regarded as non-dividing cells, and neuronal axon regeneration typically does not involve neuronal cell mitosis, ligands lacking mitogenic activity toward non-neuronal cell types that may be present at sites of NS injury may be desirable in some situations to avoid impairment of axonal regrowth that may result from mitogenic stimulation of such non-neuronal cells in the vicinity of a neuronal lesion. When present, the structural region of a ligand responsible for inducing mitogenesis or any other such undesirable biological activity may be altered in a manner that removes the unwanted activity without ablating the ability to bind a receptor and be internalized. Examples of suitable structural alteration of a ligand may include, but need not be limited to, deletion of one or more nucleotides from the appropriate region of a ligand-encoding DNA construct, mutation of nucleotides encoding one or more key amino acid residues upon which the unwanted biological activity depends, or genetically removing an entire domain encoding nucleotide sequence to remove the undesirable activity and in its place substituting a functionally innocuous domain encoding sequence. For example, FGF muteins with reduced mitogenic activity have been constructed by site-directed mutagenesis.

If the ligand has been modified so as to lack particular biological activities, binding and internalization may still be readily assayed by any one of the following tests or other equivalent tests that are routine and well known in the art. Generally, these tests involve labeling the ligand, incubating it with target cells, and visualizing or measuring intracellular label. For example, briefly, the ligand may be fluorescently labeled with fluorescein isothiocyanate (FITC), incubated with cells and examined by fluorescence microscopy or confocal microscopy for internalization. Alternatively, the ligand can be conjugated to a nucleic acid binding domain according to any of the conjugation methods described herein, complexed with a plasmid encoding a cytotoxic molecule and assessed for cytotoxicity after uptake by receptor-bearing cells.

b. Other Elements That May be Included in a Construct i. NABDs

As previously noted, nucleic acid binding domains (NABD) interact with the DNA one is seeking to deliver in either a sequence-specific manner or a sequence-nonspecific manner. When the interaction is non-specific, the nucleic acid binding domain binds nucleic acid regardless of its sequence. For example, poly-L-lysine or poly-D-lysine is a basic polypeptide that binds to oppositely charged DNA. Other highly basic proteins or polycationic compounds, including, but not limited to, histones, protamines, polyethylimine, spermine and spermidine, also bind to nucleic acids in a nonspecific manner. In addition, $MnCl_2$ and cobalt hexamine also bind DNA and may serve to condense nucleic acid.

Many proteins have been identified that bind specific sequences of DNA. These proteins are responsible for genome replication, transcription and repair of damaged DNA. The transcription factors regulate gene expression and are a diverse group of proteins. These factors are especially well suited for purposes of the subject invention because of their sequence-specific recognition. Host transcription factors have been grouped into seven well-established classes based upon the structural motif used for recognition. The major families include helix-turn-helix (HTH) proteins, homeodomains, zinc finger proteins, steroid receptors, leucine zipper proteins, the helix-loop-helix (HLH) proteins, and β-sheets. Other classes or subclasses may eventually be delineated as more factors are discovered and defined. Proteins from those classes, or proteins that do not fit within one of these classes but bind nucleic acid in a sequence-specific manner, such as SV40 T antigen and p53, may also be used.

These families of transcription factors are generally well-known (see GenBank; Pabo and Sauer, *Ann. Rev. Biochem.* 61:1053–1095, 1992; and references below). Many of these factors are cloned and the precise DNA-binding region delineated in certain instances. When the sequence of the DNA-binding domain is known, a gene encoding it may be synthesized if the region is short. Alternatively, the genes may be cloned from the host genomic libraries or from cDNA libraries using oligonucleotides as probes or from genomic DNA or cDNA by polymerase chain reaction methods. Such methods may be found in Sambrook et al., supra.

Helix-turn-helix proteins include the well studied λ Cro protein, λcI, and *E. coli* CAP proteins (see Steitz et al., *Proc. Natl. Acad. Sci. USA* 79:3097–3100, 1982; Ohlendorf et al., *J. Mol. Biol.* 169:757–769, 1983). In addition, the lac repressor (Kaptein et al., *J. Mol. Biol.* 182:179–182, 1985) and Trp repressor (Scheritz et al., *Nature* 317:782–786, 1985) belong to this family. Members of the homeodomain family include the Drosophila protein Antennapaedia (Qian et al., *Cell.* 59:573–580, 1989) and yeast MATα2 (Wolberger et al., *Cell.* 67:517–528, 1991). Zinc finger proteins include TFIIRA (Miller et al., *EMBO J.* 4:1609–1614, 1985), Sp-1, zif 268, and many others (see generally Krizek et al., *J. Am. Chem. Soc.* 113:4518–4523, 1991). Steroid receptor proteins include receptors for steroid hormones, retinoids, vitamin D, thyroid hormones, as well as other compounds. Specific examples include retinoic acid, knirps, progesterone, androgen, glucocosteroid and estrogen receptor proteins. The leucine zipper family was defined by a heptad repeat of leucines over a region of 30 to 40 residues. Specific members of this family include C/EBP, c-fos, c-jun, GCN4, sis-A, and CREB (see generally O'Shea et al., *Science* 254:539–544, 1991). The helix-loop-helix (HLH) family of proteins appears to have some similarities to the leucine zipper family. Well-known members of this family include myoD (Weintraub et al., *Science* 251:761–766, 1991); c-myc; and AP-2 (Williams and Tijan, *Science* 251:1067–1071, 1991). The P-sheet family uses an antiparallel β-sheet for DNA binding, rather than the more common ac-helix. The family contains the MetJ (Phillips, *Curr. Opin. Struc. Biol.* 1:89–98, 1991), Arc (Breg et al., *Nature* 346:586–589, 1990) and Mnt repressors. In addition, other motifs are used for DNA binding, such as the cysteine-rich motif in yeast GAL4 repressor, and the GATA factor. Viruses also contain gene products that bind specific sequences. One of the most-studied such viral genes is the rev gene from HIV. The rev gene product binds a sequence called RRE (rev responsive element) found in the env gene. Other proteins or peptides that bind DNA may be discovered on the basis of sequence similarity to the known classes or functionally by selection.

Several techniques may be used to select other nucleic acid binding domains (see U.S. Pat. No. 5,270,170; PCT Application WO 93/14108; and U.S. Pat. No. 5,223,409). One of these techniques is phage display. (See, for example, U.S. Pat. No. 5,223,409.) In this method, DNA sequences are inserted into gene III or gene VIII gene of a filamentous phage, such as M13. Several vectors with multicloning sites have been developed (McLafferty et al., *Gene* 128:29–36, 1993; Scott and Smith, *Science* 249:386–390, 1990; Smith and Scott, *Methods Enzymol.* 217:228–257, 1993). The inserted DNA sequences may be randomly generated, or may be variants of a known DNA-binding domain. Generally, the inserts encode from 6 to 20 amino acids. The peptide encoded by the inserted sequence is displayed on the surface of the bacteriophage. Bacteriophage expressing a desired nucleic acid-binding domain are selected for by binding to a preferred nucleic acid molecule for delivery, for example, a neuronal therapeutic-encoding agent. This target molecule may be single stranded or double stranded DNA or RNA. When the nucleic acid to be delivered is single-stranded, such as RNA, the appropriate target is single-stranded. When the molecule to be delivered is double-stranded, the target molecule is preferably double-stranded. Preferably, the entire coding region of the nucleic acid molecule for delivery, such as a neuronal therapeutic agent, is used as the target. In addition, elements necessary for transcription that are included for in vivo or in vitro delivery may be present in the target DNA molecule. Bacteriophage that bind the target are recovered and propagated. Subsequent rounds of selection may be performed. The final selected bacteriophage are propagated and the DNA sequence of the insert is determined. Once the predicted amino acid sequence of the binding peptide is known, sufficient peptide for use herein as an nucleic acid binding domain may be made either by recombinant means or synthetically. Recombinant means are used when the receptor-binding internalized ligand/nucleic acid binding domain is produced as a fusion protein. In addition, the peptide may be generated as a tandem array of two or more peptides, in order to maximize affinity or binding of multiple DNA molecules to a single polypeptide.

ii. Promoters

In general, constructs will also contain elements necessary for transcription and translation. In certain embodiments of the present invention, cell type preferred or cell type specific expression of a neuronal therapeutic-encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters.

Tissue specific promoters are particularly useful for expression in neuronal cells. Promoters should be active in neuronal cells, and preferably will be inactive or will have only very low activity in other cell types likely to be present in the vicinity of the NS lesion sites where the compositions and methods of the invention are to be administered. By using one of this class of promoters, an extra margin of specificity can be attained.

Neuronal cell specific promoters are especially useful for targeting neuronal therapeutic agent-encoding genes. For treating traumatized neurons in which axonal regeneration, neuronal survival and re-establishment of neural connections between perikaryons and distal neuronal targets are desired outcomes, the following promoters are especially useful: GAP43 promoter (deGroen et al., 1995, *J. Mol. Neurosci*, 66:109–119), FGF receptor promoter; neuron specific enolase (NSE) promoter (Forss-Pelter et al., 1986 *J. Neurosci. Res.* 16:141–151; Sakimura et al., 1995 *Brain Res. Mol. Br. Res.* 28:19).

Other promoters that may not be regarded as neuronal cell specific promoters but that may be useful promoters in certain embodiments include tie promoter (WO 96/09381; Korhonen et al., *Blood* 86:1828, 1995; GenBank Accession No. X60954; GenBankAccession No. S89716); VCAM-1 promoter (Iademarco et al., *J. Biol. Chem.* 267:16323, 1992; GenBank Accession No. M92431); alpha V-beta3 integrin promoter (Villa-Garcia et al., Blood 3:668, 1994; Donahue et al., BBA 1219:228, 1994); ICAM-3 promoter, expressed in tumor endothelium (Patey et al., *Am. J. Pathol.* 148:465, 1996; Fox et al., *J. Path.* 177:369, 1995; GenBank Accession No. S50015); CD44 promoter (Hofmann et al., *Cancer Res.* 53:1516, 1993; Maltzman et al., *Mol. Cell. Biol.* 16:2283, 1996; GenBank Accession No. HUMCD44B); CD40 promoter (Pammer et al., Am. *J. Pathol.* 148:1387, 1996; GenBankAccession No. HACD40L; GenBank Accession No. HSCD405FR); and notch 4 promoter (Uyttendaele et al., *Development* 122:2251, 1996).

Inducible promoters may also be used. These promoters include MMTV LTR (PCT WO 91/13160), inducible by dexamethasone, metallothionein, inducible by heavy metals, and promoters with cAMP response elements, inducible by cAMP. By using an inducible promoter, the nucleic acid may be delivered to a cell and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed when a particular FGF receptor gene is expressed may be used. Then, the nucleic acid will be transcribed when the FGF receptor, such as FGFR1, is expressed, and not when FGFR2 is expressed.

If the nucleic acid binding domain binds in a sequence specific manner, the construct must contain the sequence that binds to the nucleic acid binding domain. As described below, the target nucleotide sequence may be contained within the coding region of the neuronal therapeutic encoding agent, in which case, no additional sequence need be incorporated. Additionally, it may be desirable to have multiple copies of target sequence. If the target sequence is coding sequence, the additional copies must be located in non-coding regions of the neuronal therapeutic-encoding agent. The target sequences of the nucleic acid binding domains are typically generally known. If unknown, the target sequence may be readily determined. Techniques are generally available for establishing the target sequence (e.g., see PCT Application WO 92/05285 and U.S. Ser. No. 586,769).

In addition to the promoter, repressor sequences, negative regulators, or tissue-specific silencers may be inserted to reduce non-specific expression of the neuronal therapeutic agent or prodrug. Multiple repressor elements may be inserted in the promoter region. Repression of transcription is independent on the orientation of repressor elements or distance from the promoter. For examples of useful regulatory sequences, see, e.g., Dunaway et al., *Mol Cell Biol* 17: 182–9, 1997; Gdula et al., *Proc. Natl. Acad. Sci. USA* 93:9378–83, 1996, Chan et al., *J. Virol.* 70:5312–28, 1996; Scott and Geyer, *EMBO. J.* 14:6258–67, 1995; Kalos and Fournier, *Mol. Cell Biol.* 15:198–207, 1995; Chung et al., *Cell* 74: 505–14, 1993; and Haecker et al., *Mol. Endocrinology* 9:1113–1126, 1995.

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well known techniques.

Other elements may be incorporated into the construct. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary or enhance propagation in bacteria are incorporated. Such elements include an origin of replication, selectable marker and the like (see discussion below).

An additional level of controlling the expression of nucleic acids delivered to cells using the complexes of the invention may be provided by simultaneously delivering two or more differentially regulated nucleic acid constructs. The use of such a multiple nucleic acid construct approach may permit greater specificity in obtaining expression of the delivered genes only in appropriate cells, for example, by delivering a first construct encoding a neuronal therapeutic agent under control of a first promoter and a second construct that encodes a gene product capable of regulating the first promoter.

Alternatively, a multiple nucleic acid construct approach may permit temporal regulation of the expression of delivered nucleic acid sequences. As a non-limiting example, a first nucleic acid construct may provide a first neuronal therapeutic-encoding agent under regulation by a first promoter, such as an FGF-encoding nucleic acid regulated by a CMV promoter; a second nucleic acid construct may provide a second neuronal therapeutic-encoding agent regulated by a second promoter, such as a BDNF-encoding nucleic acid regulated by a GAP43 promoter. Without wishing to be bound by theory, regulated gene expression of this construct pair delivered to neuronal cells following NS injury may provide constitutive FGF biosynthesis for the life of the first construct to promote neuronal survival, and transient BDNF biosynthesis to promote axonal sprouting during the GAP43 induction phase. Those familiar with the art will appreciate that multiple levels of regulated gene expression may be achieved in a similar manner by selection of suitable regulatory sequences, including but not limited to promoters, enhancers and other well known gene regulatory elements.

Typically, the constructs are plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; Invitrogen catalogue, San Diego, Calif.; Novagen, Madison, Wis.; Pharmacia catalogue, Uppsala, Sweden; and others).

iii. Nuclear Translocation Signal

As used herein, a "nuclear translocation or targeting sequence" (NTS) is a sequence of amino acids in a protein that assist or mediate translocation of the protein into a cell nucleus. Examples of NTSs are set forth in Table 1 below. Comparison with known NTSs, and if necessary testing of candidate sequences, should permit those of skill in the art to readily identify other amino acid sequences that function as NTSs. The NTS may be derived from another polypeptide, or it may be derived from another region in the same polypeptide. The NTS is typically synthesized as a DNA sequence encoding the NTS and inserted appropriately into either the ligand or NABD gene sequence.

TABLE 1

| Source | Sequence* | SEQ ID NO. |
|---|---|---|
| SV40 large T | Pro$^{126}$LysLysArgLysValGlu | 1 |
| Polyoma large T | Pro$^{279}$ProLysLysAlaArgGluVal | 2 |
| Human c-Myc | Pro$^{120}$AlaAlaLysArgValLysLeuAsp | 3 |
| Adenovirus E1A | Lys$^{281}$ArgProArgPro | 4 |
| Yeast mat $\alpha_2$ | Lys$^3$IleProIleLys | 5 |
| c-Erb-A | A. Gly$^{22}$LysArgLysArgLysSer | 6 |
|  | B. Ser$^{127}$LysArgValAlaLysArgLysLeu | 7 |
|  | C. Ser$^{181}$HisTrpLysGlnLysArgLysPhe | 8 |
| c-Myb | Pro$^{521}$LeuLeuLysLysIleLysGln | 9 |
| p53 | Pro$^{316}$GlnProLysLysLysPro | 10 |
| Nucleolin | Pro$^{277}$GlyLysArgLysLysGluMetThrLysGlnLysGluValPro | 11 |
| HIV Tat | Gly$^{48}$ArgLysLysArgArgGlnArgArgArgAlaPro | 12 |
| FGF-1 | AsnTyrLysLysProLysLeu | 13 |
| FGF-2 | HisPheLysAspProLysArg | 14 |
| FGF-3 | AlaProArgArgArgLysLeu | 15 |
| FGF-4 | IleLysArgLeuArgArg | 16 |

TABLE 1-continued

| Source | Sequence* | SEQ ID NO. |
|---|---|---|
| FGF-5 | GlyArgArg | — |
| FGF-6 | IleLysArgGlnArgArg | 17 |
| FGF-7 | IleArgValArgArg | 18 |

*Superscript indicates position in protein

In order to deliver a nucleic acid to the nucleus, a construct of the present invention may also include an NTS. If the construct is designed such that the receptor-binding internalized ligand and linked nucleic acid binding domain is cleaved or dissociated in the cytoplasm, then the NTS should be included in a portion of the complex that remains bound to the nucleic acid, so that, upon internalization, the construct will be trafficked to the nucleus. Thus, the NTS is preferably included in the nucleic acid binding domain, but may additionally be included in the ligand in targeted constructs. An NTS is preferred if the neuronal therapeutic-encoding agent is DNA. If the neuronal therapeutic-encoding agent is MRNA, an NTS may be omitted. The nuclear translocation sequence (NTS) may be a heterologous sequence or a may be derived from the selected ligand. All presently identified members of the FGF family of peptides contain an NTS (see, e.g., International Application WO 91/15229 and Table 2). A typical consensus NTS sequence contains an amino-terminal proline or glycine followed by at least three basic residues in a array of seven to nine amino acids (see, e.g., Dang et al., *J. Biol. Chem.* 264:18019–18023, 1989; Dang et al., *Mol. Cell. Biol.* 8:4049–4058, 1988, and Table 1).

iv. Cytoplasm Translocation Signal

A cytoplasm-translocation signal sequence is a sequence of amino acids in a protein that causes retention of proteins in the lumen of the endoplasmic reticulum and/or translocates proteins to the cytosol. A signal sequence in mammalian cells is KDEL (Lys-Asp-Glu-Leu) (SEQ ID NO. 19) (Munro and Pelham, *Cell* 48:899–907, 1987). Some modifications of this sequence have been made without loss of activity. For example, the sequences RDEL (Arg-Asp-Glu-Leu) (SEQ ID NO. 20) and KEEL (Lys-Glu-Glu-Leu) (SEQ ID NO. 21) confer efficient or partial retention, respectively, in plants (Denecke et al., *EMBO. J.* 11:2345–2355, 1992).

A cytoplasm-translocation signal sequence may be included in either the receptor-internalized binding ligand or the nucleic acid binding domain, or in both. If cleavable linkers are used to link the ligand with the nucleic acid binding domain, the cytoplasm-translocation signal is preferably included in the nucleic acid binding domain, which will stay bound to the neuronal therapeutic-encoding agent. Additionally, a cytoplasmic-translocation signal sequence may be included in the receptor-internalized binding ligand, as long as it does not interfere with receptor binding. Similarly, the signal sequence placed in the nucleic acid binding domain should not interfere with binding to the neuronal therapeutic-encoding agent.

c. Preparation of Constructs Including Therapeutic DNA and Other Elements

Within the context of this invention, specificity of delivery in a cell type specific manner may be achieved using a construct as disclosed herein. The choice of construct to use will depend upon the nature of the target cells.

The constructs may be tested in vitro and in vivo for the desired effect. Thus, for example, if the nucleic acid encodes a neurotrophin, neuronal cell survival, neurite extension or rescue from apoptosis may be measured. Neurite extension and other assays of neurotrophin activity are known in the art (Berry et al., *Neurocytology* 1996). Any of a number of well accepted assays for induction of apoptosis may be used. These include, but need not be limited to, detection of annexin binding to exteriorized phosphatidyl serine in the plasma membrane outer leaflet (e.g., Fadok et al., *J. Immunol.* 148:2207–2216, 1992), detection of proteolytic cleavage of specific peptide substrates by apoptosis associated proteases (e.g., Nagata, *Cell* 88:355, 1997), detection of DNA fragmentation (e.g., Kerr et al., *Br. J. Canc.* 26:239, 1972; Wyllie, *Nature* 284:555, 1980; Arends et al., *Am. J. Pathol.* 136:593, 1990),or other assays for induction of programmed cell death.

a) Preparation of Constructs Containing DNA

As noted above, nucleic acids and oligonucleotides for use as described herein can be synthesized by any method known to those skilled in the art (see, e.g., Sosnowski et al, 1996 J. Biol. Chem. 271:33647; WO 93/01286, U.S. application Ser. No. 07/723,454; U.S. Pat. No. 5,218,088; U.S. Pat. No. 5,175,269; U.S. Pat. No. 5,109,124; all of which are hereby incorporated by reference). Compositions and methods for the preparation of particular DNA constructs are well known in the art, such that those having ordinary skill in the art can readily select a nucleic acid sequence for use as a neuronal therapeutic encoding agent in a construct of the invention and incorporate such a sequence into an appropriate construct for propagation and/or expression of the neuronal therapeutic agent. See, e.g., Ausubel et al., *Current Protocols in Molecular Biology*, Greene Publishing, 1995; Sambrook et al., 1989. For example, DNA can be manipulated and amplified by PCR and by using the standard techniques described in *Molecular Cloning: A Laboratory Manual*, 2nd Edition, Maniatis et al., eds., Cold Spring Harbor, N.Y. (1989). Additional examples of methods for preparing DNA for use in compositions are provided above.

i. Complex and Toroid Formation in Constructs Which Include a Ligand

Where constructs are prepared that include a ligand as provided herein, the receptor-binding internalized ligand/nucleic acid binding domain is incubated with the neuronal therapeutic-encoding or prodrug-encoded agent, preferably a circular DNA molecule, to be delivered under conditions that allow binding of the nucleic acid binding domain to the agent. Conditions for preparing such complexes and for their condensation into a toroidal shape are described in detail, for example, in Sosnowski et al, 1996 *J. Biol. Chem.* 271:33647, and in PCT/US95/07164, which are hereby incorporated by reference in their entireties.

The ability of a construct to bind nucleic acid molecules, the amount of compaction achieved, binding of the construct to a receptor, and/or internalization into a cell, may all be conveniently assessed via methods available in the art. See, e.g., the assays described in published International Application No. WO 96/36362, for example.

d. Formulation and Administration of Pharmaceutical Compositions i. Definitions and Indications

The conjugates and complexes provided herein are useful in the treatment of various acute and chronic NS injury as may result following acute or chronic NS injury resulting from physical transection/trauma, contusion/compression or surgical lesion, vascular pharmacologic insults including hemorrhagic or ischemic damage, or from neurodegenerative or other neurological diseases including those having genetic and/or autoimmune components. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition.

As noted above, the compositions of the present invention are used to treat NS injury. In acute or chronic NS injury resulting from hemorrhagic, ischemic, hypoxic, or surgical lesion or other NS trauma, neural connections may be damaged or severed. Restoration or protection of neural pathways through induction of neuronal survival or directed axonal regrowth along projection tracts may be desirable, in order to maintain or re-establish continuous retrograde flow of neurotrophic and/or neuronal therapeutic factors from the distal neuronal target to the neuronal cell body (perikaryon). As such, the present invention provides nucleic acid delivery vehicles that may bind to cell surface molecules (receptors) via a ligand and internalize, thus delivering a nucleic acid molecule. The invention also encompasses nucleic acid delivery vehicles that are internalized by non-specific mechanisms, including but not limited to adsorptive endocytosis, fluid phase endocytosis/pinocytosis, altered membrane permeability or gene activated matrices, or other mechanisms for nucleic acid delivery to cells. The invention further encompasses nucleic acid delivery using recombinant adenovirus or bacteriophage vectors. Genetically modified adenoviruses and bacteriophage exhibiting specifically targeted altered host cell tropism have previously been disclosed in U.S. application Ser. No. 09/039,060, filed Mar. 13, 1998, and U.S. application Ser. No. 08/920,396, filed Aug. 29, 1997, respectively, which are inherently incorporated by reference in their entireties.

ii. Preparation of Pharmaceutical Agents

Pharmaceutical carriers or vehicles suitable for administration of the conjugates and complexes provided herein include any such carriers known to those skilled in the art to be suitable for the particular mode of administration. In addition, the conjugates and complexes may be formulated as the sole pharmaceutically active ingredient in the composition or may be combined with other active ingredients.

The conjugates and complexes can be administered by any appropriate route, for example, orally, parenterally, including intravenously, intradermally, subcutaneously, or topically, in liquid, semi-liquid or solid form and are formulated in a manner suitable for each route of administration. Preferred modes of administration depend upon the lesion site to be treated. The conjugates and complexes may be formulated into a gene activated matrix (GAM), which is described in greater detail below. The conjugates and complexes may be administered by implantation into the site of the body to be treated therapeutically.

The conjugates and complexes herein may be formulated into pharmaceutical compositions suitable for topical, local, intravenous and systemic application. For the various uses herein, local administration at or near a lesion site is preferred. Effective concentrations of one or more of the conjugates and complexes are mixed with a suitable pharmaceutical carrier or vehicle. As used herein an "effective amount" of a compound for treating a particular lesion is an amount that is sufficient to partially or fully maintain, restore, or in some manner re-establish the neural connections whose loss may be associated with the injury. Such amount may be administered as a single dosage or may be administered according to a regimen whereby it is effective. Repeated administration may be required to achieve the desired degree of neuronal regeneration.

The concentrations or amounts of the conjugates and complexes that are effective requires delivery of an amount, upon administration, that restores functional ability and/or prevents undesirable sequelae to NS injury. Typically, the compositions are formulated for single dosage administration. Therapeutically effective concentrations and amounts may be determined empirically by testing the conjugates and complexes in known in vitro and in vivo systems, such as those described here; dosages for humans or other animals may then be extrapolated therefrom.

The construct is included in the pharmaceutically acceptable carrier in an amount sufficient to exert a therapeutically useful effect in the absence of undesirable side effects on the patient treated. The constructs may be delivered as pharmaceutically acceptable salts, esters or other derivatives of the constructs include any salts, esters or derivatives that may be readily prepared by those of skill in this art using known methods for such derivatization and that produce compounds that may be administered to animals or humans without substantial toxic effects. It is understood that number and degree of side effects depends upon the condition for which the conjugates and complexes are administered. For example, certain toxic and undesirable side effects are tolerated when treating life-threatening illnesses, such as tumors, that would not be tolerated when treating disorders of lesser consequence. The concentration of construct in the composition will depend on absorption, inactivation and excretion rates thereof, the dosage schedule, and amount administered as well as other factors known to those of skill in the art.

Preferably, the conjugate and complex are substantially pure. As used herein, "substantially pure" means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Solutions, pastes or suspensions used for perineural, parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parenteral preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

Upon mixing or addition of the construct(s) with the vehicle, the resulting mixture may be a solution, suspension, gel, paste, semisolid, dispersion, emulsion or the like. The form of the resulting mixture depends upon a number of factors, including the intended mode of administration and the solubility of the construct in the selected carrier or vehicle. The effective concentration is sufficient for ameliorating the symptoms of the disease, disorder or condition treated and may be empirically determined based upon in vitro and/or in vivo data, such as the data from the rat ophthalmic or spinal cord model. If necessary, pharmaceutically acceptable salts or other derivatives of the conjugates and complexes may be prepared.

The active materials can also be mixed with other active materials, that do not impair the desired action, or with materials that supplement the desired action, including viscoelastic materials, such as hyaluronic acid, which is sold under the trademark HEALON (solution of a high molecular weight (MW of about 3 millions) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803), VISCOAT (fluorine-containing (meth) acrylates, such as, 1H,1H,2H,2H-hepta-decafluoro-decylmethacrylate; see, e.g., U.S. Pat. Nos. 5,278,126, 5,273,751 and 5,214,080; commercially available from Alcon Surgical, Inc.), ORCOLON (see, e.g., U.S. Pat. No. 5,273,056; commercially available from Optical Radiation Corporation), methylcellulose, methyl hyaluronate, poly-acrylamide and polymethacrylamide (see, e.g., U.S. Pat. No. 5,273,751). The viscoelastic materials are present generally in amounts ranging from about 0.5 to 5.0%, preferably 1 to 3% by weight of the construct material and serve to coat and protect the treated tissues. The compositions may also include a dye, such as methylene blue or other inert dye, so that the composition can be seen when injected into the eye or contacted with the surgical site during surgery.

The active materials can also be mixed with other active materials that do not impair the desired action, or with materials that supplement the desired action, such as gene activated matrices described below, which may impair undesirable scar tissue formation.

Finally, the compounds may be packaged as articles of manufacture containing packaging material, one or more conjugates and complexes or compositions as provided herein within the packaging material, and a label that indicates the indication for which the construct is provided.

iii. Administration

Typically a therapeutically effective dosage should result from local application at NS lesion sites and should provide about 1 ng up to 100 µg of active ingredient, preferably about 1 ng to about 10 µg per single dosage administration. It is understood that the amount to administer will be a function of the construct selected, the indication treated, and possibly the side effects that will be tolerated.

Therapeutically effective concentrations and amounts may be determined for each application herein empirically by testing the conjugates and complexes in known in vitro and in vivo systems (e.g., murine, rat, rabbit, or baboon models), such as those described herein; dosages for humans or other animals may then be extrapolated therefrom. The rat optic nerve lesion model is a recognized model for studying the effects of locally applied therapeutics and is described hereinbelow in the Examples.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

As provided, the present invention overcomes a problem associated with therapies in the prior art that are directed to therapeutic delivery to the CNS because the active ingredient does not have to traverse the blood brain barrier (BBB). It is well known in the art that the BBB acts as a selective molecular filter that may exclude compositions from the CNS. Accordingly, the compositions and methods provided herein for CNS delivery of neuronal therapeutic agents, including neuronal therapeutic encoding agents, permit specific therapeutic uptake by CNS cells while avoiding the limitations placed on delivered agents that must traverse the selective mechanisms of the BBB.

4. METHODS OF PROMOTING NEURONAL SURVIVAL AND REGENERATION

Gene activated matrix (GAM) comprising nucleic acid encoding a neuronal therapeutic agent may be administered to the vicinity of an injured or diseased neuron, for example via a semi-solid gel comprising the gene activated matrix that is inserted surgically at the injury site. Alternatively the GAM may be injected into the injury site as a liquid and then induced to form a gel, for example as a fibrin clot. As described above, a neuronal therapeutic encoding agent undergoes axonal delivery of therapeutic DNAs via uptake and retrograde transport to the cell body of the neuron. The therapeutic DNA is delivered to the axon via the gene activated matrix. The therapeutic DNA comprises an inactive prodrug that is transcribed and translated within a neuronal cell to express an active neuronal therapeutic protein factor. The active neurotropic protein factor stimulates axonal outgrowth into the gene activated matrix, which in turn delivers more therapeutic DNA (prodrug) that is expressed as active neurotrophin. Upon activation of the growth response, neurons secrete matrix-degrading enzymes to facilitate axonal regrowth through the wound.

The delivery and expression of neuronal therapeutic encoding genes within a gene activated matrix to promote neuronal survival and regeneration may be assessed in any number of in vivo model systems. In particular, a lesioned rat optic nerve repair model or a regenerating rat spinal cord model may be used. In each animal model, experimentally damaged nerves are treated with a gene activated matrix that provides targeted delivery of a gene encoding a neuronal therapeutic agent or a reporter gene. If the gene encodes a reporter, the reporter product is assayed post mortem. If the gene encodes a neuronal therapeutic agent, the neuronal therapeutic protein is assayed and regeneration of the damaged nerve is analyzed post mortem. Moreover, any assayable gene product may be used. For reporter genes a wide variety of suitable genes are available. As described above, such reporters include but need not be limited to β-galactosidase, alkaline phosphatase, β-glucuronidase, green fluorescent protein, large T antigen, and any protein for which an antibody exists or can be developed. Antibodies to the neuronal therapeutic agent may be developed for immunohistochemical analysis or Western blot analysis of regenerating neurons. Neuronal therapeutic agents are described herein.

The delivery and expression of neuronal therapeutic agent encoding genes within a gene activated matrix to promote neuronal survival and regeneration may be assessed in in vitro model systems. In particular, target cells are grown in culture and incubated with the gene activated matrix comprising a neuronal therapeutic agent-encoding gene or a reporter gene. Moreover, any assayable gene product may be used. The reporter gene product or the neuronal therapeutic encoding agent gene product may be assayed as described above.

The following examples are included for illustrative purposes only and are not intended to limit the scope of the invention.

EXAMPLES

Example 1

Preparation of Gene Activated Matrix Containing FGF2-Poly-L-Lysine Complexed with a Plasmid Encoding GFP Protein (GFP) Reporter Gene under Promoter Regulation Plasmid isolation, production of competent cells, transformation and manipulations using the M13 cloning vectors are performed as described (Sambrook et al., *Molecular Cloning, a Laboratory Manual*, Cold Spring Harbor Laboratory Press, Cold Spring Harbor, N.Y., 1989). DNA fragments are purified using the Geneclean II kit, purchased from Bio 101 (La Jolla, Calif.). Recombinant DNA constructs are sequenced using the Sequenase kit (version 2.0, United States Biochemical, Cleveland, Ohio) according to the manufacturer's instructions. Conjugation of FGF2 to poly-L-lysine $K_{84}$ homopolymer to produce FGF2-K is as described by Sosnowski et al. (1996 *J. Biol. Chem.* 271:33647–33653). Preparation of FGF2-poly-L-lysine complexed with a plasmid encoding green fluorescent protein (GFP) under CMV promoter regulation is also essentially as described above for FGF2-K complexed with a plasmid encoding β-galactosidase above, except that a plasmid encoding GFP under CMV promoter control (pEGFP, Clontech, Palo Alto, Calif.) was used instead of the galactosidase construct.

Fibrin matrices to be used for the assembly of GAM are produced using the TISSEEL™ Kit (ImmunoAG, Vienna, Austria) according to the manufacturer's instructions. Briefly, lyophilized TISSEEL™ material containing human fibrinogen, plasma fibronectin, factor XIII and plasminogen is reconstituted in a solution containing various concentrations of FGF2-K-GFP and bovine aprotinin following the TISSEEL™ manufacturer's recommendations to form a first component that is maintained at 37° C. for at least 10 min.

Lyophilized human thrombin provided in the kit is reconstituted with 40 mM $CaCl_2$ to form a second component, which is also held at 37° C. prior to use. Equal volumes of the first and second components are then mixed to initiate fibrin formation and drawn into capillary tubing (Accupette™, Dade Diagnostics, Inc., Aguada, Puerto Rico) to cure (usually 15–30 min at room temperature), after which the matrix is extruded sterilely and cut into sections for implantation at CNS lesion sites.

Collagen GAMs are prepared by lyophilizing FGF2-K or K condensates prepared as described above but using DNA encoding FGF2 or GFP, and then reconstituting theses lyophilized condensates with 2 mg sterile collagen paste (Collagen Corporation, Palo Alto, Calif.) in sterile petri dishes. Alternatively, GAM plugs are formed by adding 3 ml of Cell Prime™ collagen (1.5 mg/ml in DMEM, Collagen Corporation) to 1 ml of FGF2-K-DNA (50 µg DNA, 100 µg FGF2-K), pipetting 100 µl aliquots onto a dry ice-chilled foil freezing substrate (prepared using aluminum foil formed into dimples on an empty plastic 1000 µl pipette tip rack) and lyophilizing the plugs. Each plug (2.34 µg DNA, 4.68 µg FGF2-K, 46.8 µg collagen) is rehydrated with one microliter of sterile water prior to its implantation at a CNS lesion site.

The following GAMs containing FGF-targeted GFP encoding plasmids are prepared according to these methods:

| GAM | Matrix Component | Targeting Agent | Linker | Reporter Gene Encoding DNA |
| --- | --- | --- | --- | --- |
| K-GFP/collagen | collagen | none | poly-L-lysine | GFP |
| FGF2-K-GFP/collagen | collagen | FGF2 | poly-L-lysine | GFP |
| K-GFP/fibrin | fibrin | none | poly-L-lysine | GFP |
| FGF2-K-GFP/fibrin | fibrin | FGF2 | poly-L-lysine | GFP |

Example 2

Preparation of DNA Construct Containing the Neuronal GAP43 Promoter

Plasmid isolation, production of competent cells, transformation and manipulations using the M13 cloning vectors are performed as described (Sambrook et al., *Molecular Cloning, a Laboratory Manual*, Cold Spring Harbor Laboratory Press, Cold Spring Harbor, N.Y., 1989). DNA fragments are purified using the Geneclean II kit, purchased from Bio 101 (La Jolla, Calif.). Recombinant DNA constructs are sequenced using the Sequenase kit (version 2.0, United States Biochemical, Cleveland, Ohio) according to the manufacturer's instructions. DNA containing the human GAP43 promoter sequence (Genbank accession number X840768) is obtained as described in de Groen et al. (*J. Mol. Neurosci.* 6:109–119, 1995) and incorporated into plasmids in operative linkage with reporter gene encoding or neuronal therapeutic agent encoding sequences.

Example 3

Delivery and Expression of Targeted GFP Gene in Lesioned Rat Optic Nerve Repair Model In this example, targeted delivery of the GFP reporter gene to rat optic nerve neurons is conducted using a ligand as a molecular targeting agent in an in vivo model of neuronal regeneration.

Transgene expression of neuronal cells in vivo following experimentally induced axonal lesion is monitored in the rat optic nerve repair model. See, e.g., Logan et al., *Meth. Neurosci.* 21:3–19, 1994, which is hereby incorporated by reference in its entirety. Adult rats are anesthetized by intraperitoneal injection of physiological saline solution containing ketamine (40 mg/kg), acepromazine (1.2 mg/kg) and xylazine (8 mg/kg). The optic nerve is accessed intraorbitally by a dorsolateral approach and severed by transection using manual pressure applied with surgical forceps. (Berry et al., *J. Neurocytol.* 25:147–170, 1996). Care is taken to avoid damaging the central retinal artery or the optic nerve sheath. The conjugate having the following components (in 1–20 µL) is injected under pressure using a glass microsyringe at the optic nerve lesion site:

FGF2-Kn-pCMV promoter-GFP encoding gene], wherein

FGF2 is the ligand protein as described in Sosnowski et al. (1996 *J. Biol. Chem.* 271:33647–33653).

Kn is the poly-L-lysine linker as described in Sosnowski et al. (supra) and having n=84;

and pCMV promoter-GFP encoding gene is the plasmid described in Example 1 and containing the GFP gene under regulation of CMV promoter, and further wherein SPDP conjugation and plasmid complex formation are as described in Sosnowski et al. (1996*J. Biol. Chem.* 271:33647–33653). A similar construct containing the lacZ gene encoding beta-galactosidase instead of GFP was also prepared. (See Example 1.)

Following injection the lesion site is closed by standard surgical procedures. At 7 days post lesion, retinas are dissected and whole mounts observed under the fluorescent microscope for the detection of GFP. For the detection of beta-galactosidase activity, retinas are fixed in 4% paraformaldehyde and then incubated with Xgal, a substrate for this enzyme. FIG. 1 illustrates expression of the reporter genes beta-galactosidase and GFP in retinal ganglion cells.

Example 4

Delivery and Expression of FGF Gene in Lesioned Rat Optic Nerve Repair Model

In this example, GAM delivery of a gene encoding the neuronal therapeutic agent human FGF2 to rat optic nerve neurons is conducted using a collagen GAM in the lesioned rat optic nerve model of in vivo neuronal repair. GAMs having neuronal therapeutic encoding agent DNA condensed on poly-L-lysine linkers are prepared using type I collagen (67 mg/ml, Collagen Corporation, Palo Alto, Calif.) ssentially as described above in Example 1; GAMs have either no targeting agent or he FGF2 ligand as a molecular targeting agent.

Figure 2:
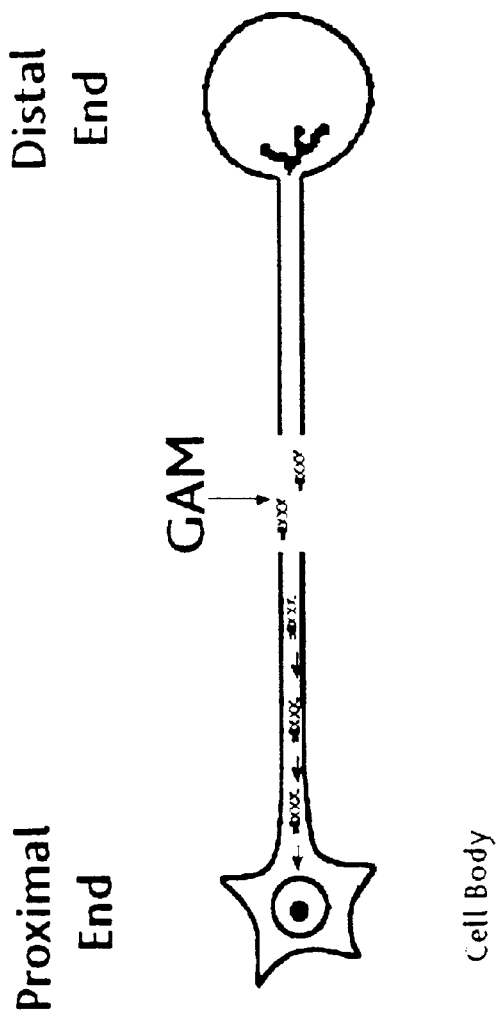
FIG. 2 is a schematic diagram illustrating placement of a GAM at a neuronal lesion site and retrograde axonal transport of neuronal therapeutic encoding agent to the perikaryon.

Experimental lesion of the optic nerve is performed as in Example 3 except that animals are not sacrificed until day 30 and day 100 post-lesion. For each GAM preparation, surgery and GAM implantation at the site of injury are conducted on a group of 20 animals, each divided into four sets of five animals. Optic nerve injury and GAM implantation are performed on both eyes. FIG. 2 is a schematic diagram illustrating placement of a GAM at a neuronal lesion site and retrograde axonal transport of neuronal therapeutic encoding agent to the perikaryon.

At day 30 post-lesion, a first set of animals from each treatment group is injected intravitreally with 5 µl of 20% (w/v) biotinylated dextran amine (BDA, Molecular Probes, Eugene, Oreg.), a qualitative anterograde tracer of axonal regeneration when administered intravitreally. A second set of animals from each group is injected with 1 µl of 20% BDA in the optic nerve at a point 2 mm distal to the lesion site, following surgical access of the site. Administration of BDA in this fashion permits quantification of optic nerve axonal regeneration when labeled retinal ganglion cells (RGC) are counted post mortem. (Berry et al.,*J. Neurocytol.* 25:147–170, 1996.)

Figure 3:
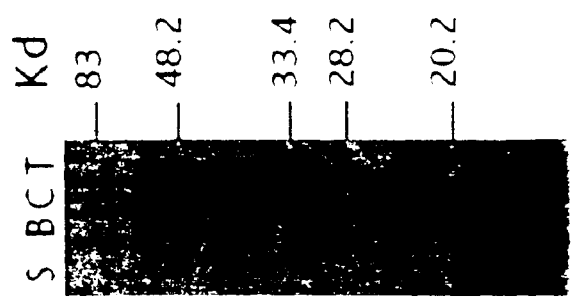
FIG. 3 depicts the results of Western immunoblot analysis showing expression of a neuronal therapeutic encoding agent in the lesioned rat optic nerve in vivo neuronal repair model.

Also at day 30 post-lesion, a third set of animals is sacrificed and retinas collected and snap frozen in liquid nitrogen. The dissected retinas are detergent solubilized and affinity extracted with heparin-Sepharose to isolate expressed FGF molecules for quantification by Western immunoblot analysis according to Coffin et al. (Mol. Biol. Cell 6:1861–1873, 1995), which is hereby incorporated by reference. Bound proteins are resolved by SDS-polyacrylamide gel electrophoresis, blot transferred to a polyvinyldiflouride membrane and detected radioimmunochemically or by chemiluminescence according to well known methods. As shown in FIG. 3, human FGF2 expression is readily detectable in rat retinas recovered from animals to which were administered GAMs having either no targeting agent (lane C) or the FGF2 ligand as a molecular targeting agent (lane T). Under the conditions employed, rat FGF was not detectable in rat brain (lane B) using an antibody that preferentially binds to human FGF2.

At day 10 and 100 post-lesion, a fourth set of animals is sacrificed, perfusion fixed, and optic nerves and retinas are dissected and processed for histochemistry and immunohistochemistry. Briefly, animals are re-anesthetized and perfused through the left ventricle at atmospheric pressure with the descending aorta clamped and both external jugular veins incised with physiological saline for 1 min followed by 4% paraformaldehyde in 0.1M phosphate buffer, pH 7.2, for 5 min. After perfusion, optic nerves are dissected, dehydrated through a graded alcohol series, embedded in a low melting point polyester wax and stored at 4° C. (Logan et al., *Meth. Neurosci.* 21:3–19, 1994) Longitudinal optic nerve microtome sections (7 µm thickness) are cut with a cooled chuck, floated onto a 1% gelatin solution on slides and air dried.

For immunohistochemical identification of specific cellular components within lesions, sections are dewaxed, rehydrated and soaked 5 min in phosphate buffered saline. Immunohistochemical staining of optic nerve sections is performed according to established techniques (Berry et al., *J. Neurocytol.* 25:147–170, 1996) using appropriate dilutions of commercially available primary antibodies specific for the marker proteins listed below. Detection is with fluorophore (FITC or TRITC) or peroxidase conjugated secondary antibodies (Vector Laboratories, Inc., Burlingame, Calif.) and 3,3',4,4'-diaminobenzidine (Vector) as a peroxidase substrate, all according to the supplier's recommendations:

Primary antibodies are: rabbit polyclonal anti-GAP43 (1:5000, G. Wilkin, Imperial College, London), rabbit anti-bovine glial fibrillary acidic protein (astrocytic marker) (1:1000, Sigma, St. Louis, Mo.), rabbit anti-rat fibronectin (1:100, Dakopatts, Ltd., Carpinteria, Calif.), rabbit anti-mouse sarcoma laminin (1:100 Sigma), rabbit anti-rat carbonic anhydrase-II (oligodendrocyte marker) (1:5000, N. Gregson, UMDS, London), anti-rat monocyte marker ED1 (1:200, Serotec, Ltd., Oxford, UK), anti-rat monocytic OX47 (Serotec), anti-RT97 (neurofilament marker) (1:200, Serotec), rabbit anti-tenascin, monoclonal mouse anti-chondroitin-6-sulphate proteoglycan.

Briefly, antibodies are diluted as indicated above in PBS containing 1% (w/v) bovine serum albumin, and 60 µl are applied to sections at 4° C. overnight. Slides are immersion washed twice in PBS, and then incubated for one additional hour in appropriate secondary antibodies (FITC- or TRITC-labeled anti-Ig or ABC kit for HRP detection, all from Vector Laboratories). Slides are washed twice in PBS and HRP labeled sections are developed with diaminobenzidine (Vector). Slides are then examined and evaluated using immunofluorescence microscopy (FITC, TRITC) and dark ground illumination microscopy (HRP) as described. (Berry et al., 1996).

For three-color analysis, the primary antibodies are polyclonal anti-glial fibrillary acidic protein antisera (1:1000, Advanced Immunochemical, Inc., Long Beach, Calif.), mouse monoclonal IgG anti-GAP-43 (1:100, Sigma, St. Louis, Mo.) and affinity purified polyclonal rabbit anti-laminin antibodies (1:100, Sigma). Sections are pretreated for 1 hr at room temperature with 60 μl 1.5% (v/v) normal goat serum in 0.1% bovine serum albumin/PBS, then incubated overnight at 4° C. in 60 μl of a cocktail containing the three primary antibodies diluted to the working concentrations indicated above in 0.1% BSA/PBS. The next day, slides are washed twice in PBS and incubated one hour in the dark with FHTC-goat anti-mouse IgG (Vector Laboratories, Burlingame, Calif.) according to the manufacturer's instructions, then washed twice in PBS again. Rhodamine conjugated goat anti-guinea pig Ig (Chemicon, Temecula, Calif.) is then applied to the sections for an hour according to the manufacturer's instructions, and the slides are again twice washed prior to incubation for one hour in biotinylated goat anti-rabbit IgG (Vector Laboratories, Burlingame, Calif.) according to the manufacturer's instructions. Slides are then washed, incubated in avidin-AMCA conjugate (Vector Laboratories) according to the supplier's recommendations, washed again and fixed in 2% paraformaldehyde prior to visualization by immunofluorescence microscopy using a microscope equipped with a UV light source and filter sets according to the manufacturers' specifications for each fluorophore.

Figure 4:
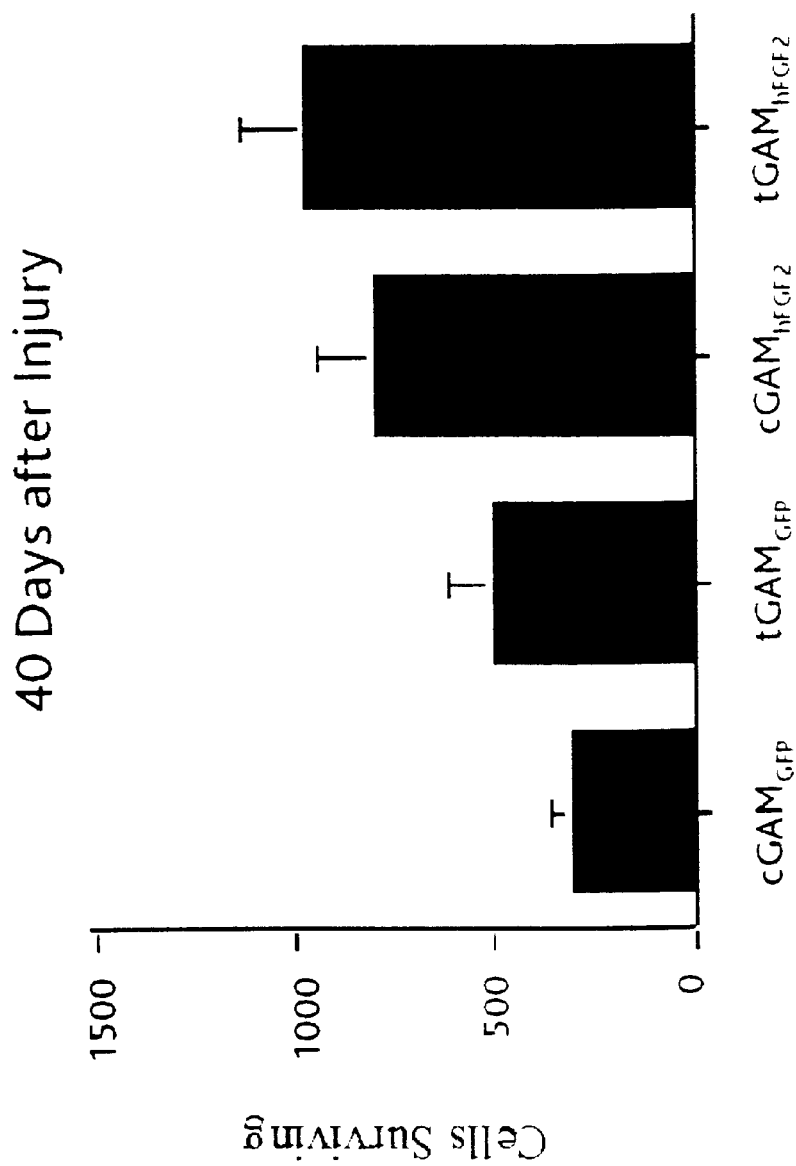
FIG. 4 depicts neuronal survival 40 days after injury in animals to which GAMs were administered.
Figure 5:
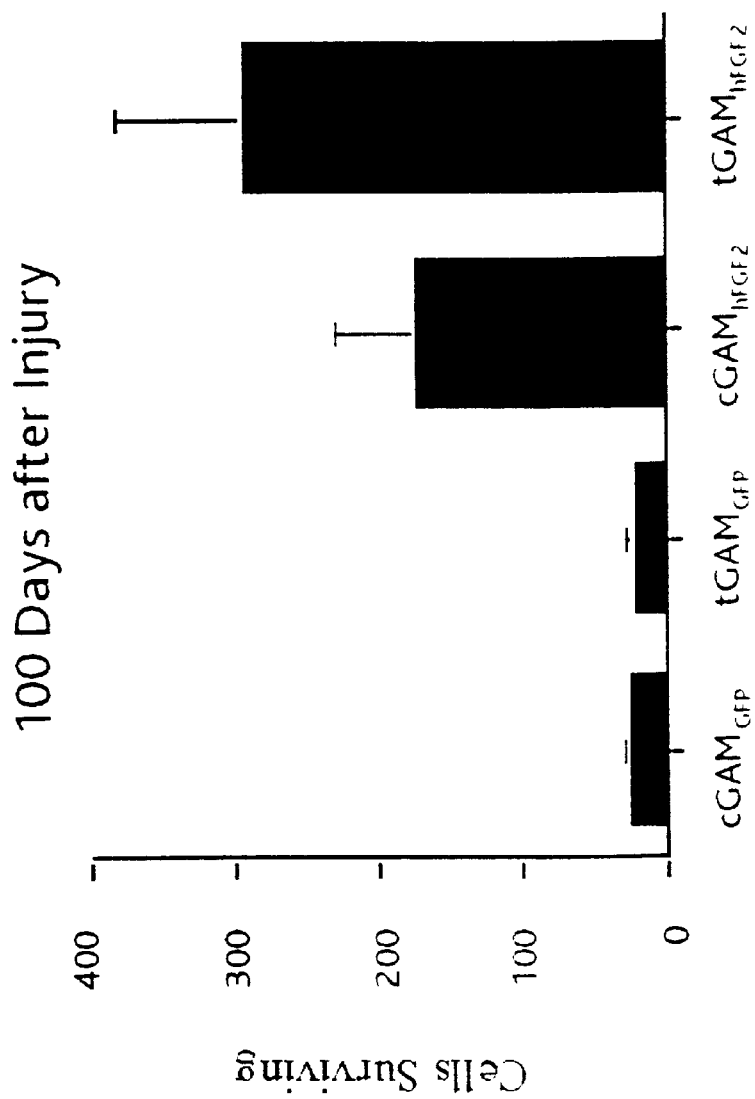
FIGS. 5 depicts neuronal survival 100 days after injury in animals to which GAMs were administered.

At day 30 and 100 post-lesion, an additional set of animals from each treatment group is injected with 1 μl of 20% (w/v) rhodamine dextran amine (RDA, Molecular Probes, Eugene, Oreg.) in the proximal end of the transected optic nerve following surgical access of the site. Administration of RDA in this fashion permits quantification of neuronal survival when labeled retinal ganglion cells (RGC) are counted post mortem. (Berry et al., *J. Neurocytol.* 25:147–170, 1996.) FIGS. 4 and 5 depict neuronal survival 40 days after injury (FIG. 4) and 100 days after injury (FIG. 5) in animals to which GAMs were administered having either condensed neuronal therapeutic encoding agent DNA (GFP or human FGF2) but no targeting agent (cGAM) or condensed neuronal therapeutic encoding agent DNA linked to the FGF2 ligand as a molecular targeting agent (tGAM).

The following GAMs containing FGF-targeted FGF encoding plasmids are prepared according to the methods of Example 1:

| GAM | Matrix Component | Molecular Targeting Component | Linker | Reporter Gene Encoding DNA |
|---|---|---|---|---|
| FGF2-K-GFP/collagen | Type I collagen | FGF2 | poly-L-lysine ($K_{84-100}$) | GFP |

-continued

| GAM | Matrix Component | Molecular Targeting Component | Linker | Reporter Gene Encoding DNA |
|---|---|---|---|---|
| FGF2-K-FGF/collagen | Type I collagen | FGF2 | poly-L-lysine ($K_{84-100}$) | FGF2 (human) |
| K-FGF/collagen | Type I collagen | none | poly-L-lysine ($K_{84-100}$) | FGF2 (human) |
| K-GFP/collagen | Type I collagen | none | poly-L-lysine ($K_{84-100}$) | GFP |

Example 5

Preparation of a Cholera Toxin B-Chain Targeted Conjugate for Delivery of a Neuronal Therapeutic Encoding Agent A. Derivatization of Poly-L-lysine ($K_{100}$) with SPDP.

Poly-L-lysine ($K_{100}$) is modified with a 1.5 molar excess of N-succinimidyl-3-[2-pyridyldithio]proprionate (SPDP, Pierce Chemical Co., Rockford., Ill.) for 30 min at room temperature in conjugation buffer (0.1 M $PO_4$-pH 8.0, 0.1 M NaCl, 1 mM EDTA) and unreacted SPDP is removed by diafiltration using a 10 kDa cutoff membrane. PDP concentration is determined by optical density at 314 nm and $K_{82}$ concentration is determined using the BCA protein assay. PDP- $K_{82}$ is reduced for 10 min at room temperature by the addition of dithiothreitol (DTT) to a final concentration of 5 mM to yield sulfhydryl modified $K_{100}$. Excess DTT is removed by diafiltration.

B. Derivatization of CTb with SPDP

Cholera Toxin B Chain (CTb, Calbiochem, San Diego, Calif.) is equilibrated in conjugation buffer and reacted with a 5-fold molar excess of SPDP for 30 min at room temperature, after which unreacted SPDP is removed by diafiltration. PDP and CTh concentrations are measured as described above to determine a PDP:CTh molar ratio of 2–3.

C. Conjugation of SH-$K_{100}$ to CTb-PDP and Purification of Conjugate

SH-$K_{100}$ and CTb-PDP are combined at a molar ratio of 1:1.5 and reacted overnight at 4° C. The reaction is terminated by removal of unreacted CTb-PDP using a Resource S™ column (Pharmacia, Inc., Piscataway, N.J.) equilibrated in buffer A (0.1 M $PO_4$-pH 8.0, 1 mM EDTA) and eluted with two column volumes of the same buffer followed by a step gradient of three column volumes of 10% buffer B (buffer A made 3M in NaCl) in buffer A, then a 10%–70% buffer B gradient over 24 column volumes and then four column volumes of buffer B undiluted. Pooled fractions in the 20–40% B portion of the gradient contain CTb-$K_{100}$ conjugate and $K_{100}$, the latter being removed either by gel filtration chromatography using a Sephacryl™ S200 column (Pharmacia) isocratically eluted with 10 mM Hepes-pH 7.3–0.13 M NaCl, or by Butyl-650M (TosoHaas, Linton, UK) hydrophobic interaction chromatography of pooled Resources™ fractions made 1.5 M in ammonium sulfate.

Yield and purification of the conjugate are determined using absorbance at 280 nm and BCA assay for protein quantification and integration analysis of chromatography peaks, plus LLS-particle size analysis. From 5 mg of CTb starting material, 3 mg of final product is obtained. Biological activity of the conjugate is also determined, using transfection assays according to references cited herein.

(See, e.g., Sosnowski et al., 1996 *J. Biol. Chem.* 271:33647–33653.)

Figure 6:
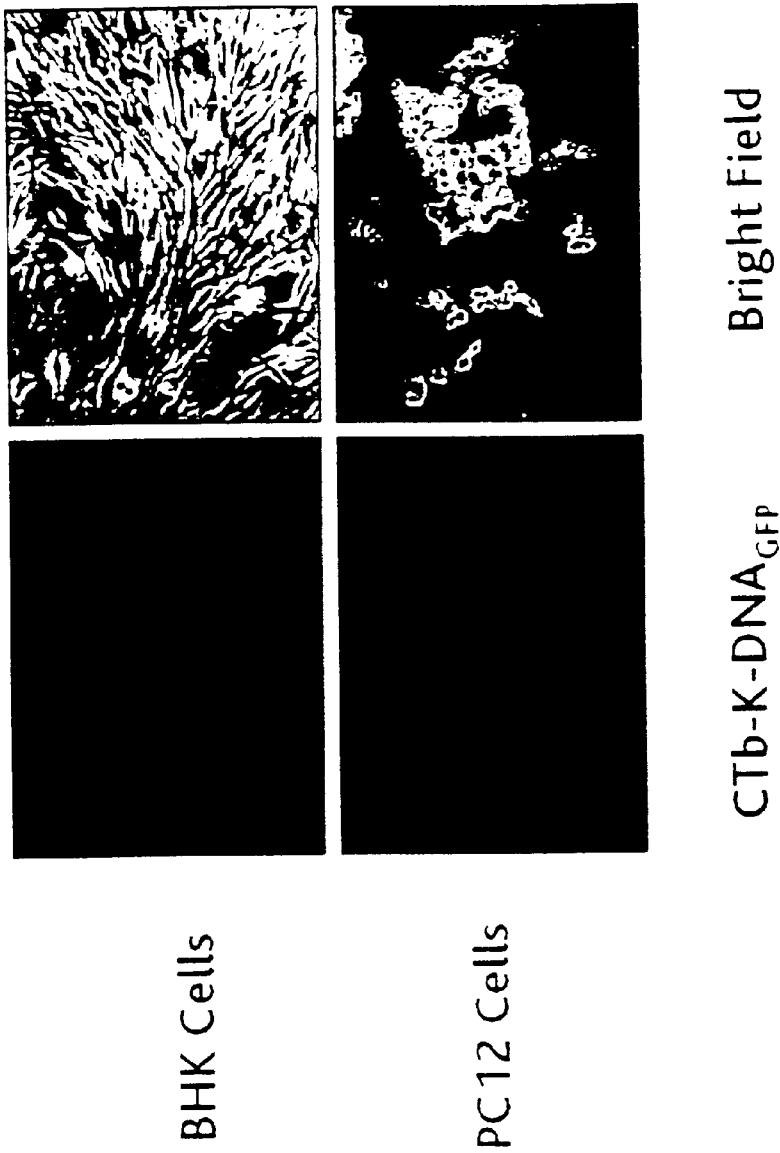
FIG. 6 illustrates target specificity of conjugates having CTb as a targeting agent.

In order to test the target specificity of CTb conjugates, PC12 (rat pheochromocytoma) and BHK cells are plated on a 24 well plate and incubated for 48 hr with CTb-K-$DNA_{GFP}$. GFP expression is analyzed under an inverted fluorescent microscope. Representative results of such analysis are shown in FIG. 6.

Example 6

Neuronal Delivery and Expression of LacZ Gene in Lesioned Rat Spinal Cord

In this Example, a rat model system is presented for introducing experimental CNS lesions and using FGF2 targeted condensed DNAs to deliver genes to injured neurons in the spinal cord. The first order ascending sensory system of the gracile tract and the descending corticospinal system are used to model spinal cord. Both tracts are found in the dorsal funiculi and at the level of T8 are easily lesioned surgically by contusion or section without disturbing the LA/5 root entry zone.

The dorsal funiculus of the spinal cord is crushed at the level of T8 by forceps as follows: The surgical approach is standard through a partial laminectomy, dura and arachnoid are incised, and the points of forceps separated to the medial margins of the dorsal root entry zone along the dorsolateral sulcus, and lowered to a depth of 2 mm. Approximation of the tips crushes the dorsal columns, including all the axons in the ascending gracile tracts and the descending corticospinal tracts bilaterally. The pia remains intact and the patency of the overlying vessels is preserved.

Figure 7:
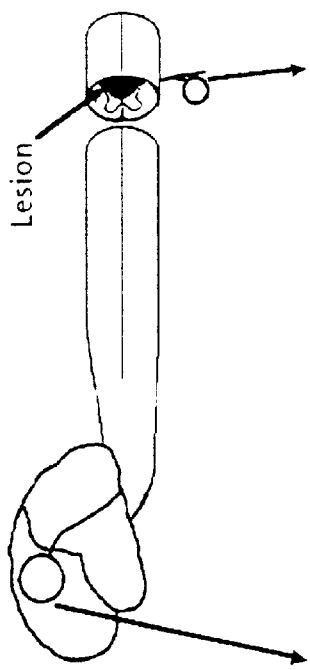
FIG. 7 illustrates bidirectional retrograde axonal delivery and expression of targeted condensed DNAs in a rat model system of spinal cord injury.
Figure 7:
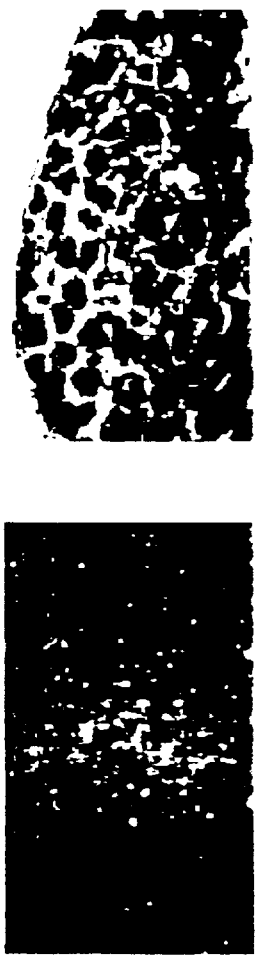

Targeted condensed DNA encoding the LacZ gene is prepared according to Sosnowski et al. (1996 *J. Biol. Chem.* 271:33647–33653). Access to the lesion site for injection of the DNA is through the exposed pia overlying the site of spinal cord transection. At 7 days post-lesion, animals are sacrificed and perfusion fixed as described in Example 3. Brains, spinal cords and dorsal root ganglia (DRG) are dissected and processed for beta-galactosidase histochemistry, also as described in Example 3. FIG. 7 illustrates representative fields showing bidirectional retrograde transfection as evidenced by beta-galactosidase (LacZ) gene expression.

Example 7

Delivery and Expression of Neuronal Therapeutic Encoding Agents in Regenereting Rat Spinal Cord In this Example, a rat model system is presented for introducing experimental CNS lesions and for using GAMs to deliver neuronal therapeutic agent encoding genes to regenerating axons in the spinal cord. The first order ascending sensory system of the gracile tract and the descending corticospinal system are used to model spinal cord regeneration using both short (15 and 30 days post lesion, dpl) and long (60 and 90 dpl) sampling times. Both tracts are found in the dorsal funiculi and at the level of T8 are easily lesioned surgically by contusion or section without disturbing the L4/5 root entry zone.

The dorsal funiculus of the spinal cord is crushed at the level of T8 by forceps as follows: The surgical approach is standard through a partial larninectomy, dura and arachnoid are incised, and the points of forceps separated to the medial margins of the dorsal root entry zone along the dorsolateral sulcus, and lowered to a depth of 2 mm. Approximation of the tips crushes the dorsal columns including all the axons in the ascending gracile tracts and the descending corticospinal tracts bilaterally. Both tracts are found in the dorsal funiculi and at the level of T8 are easily lesioned without disturbing the L4/5 root entry zone. The pia remains intact and the patency of the overlying vessels is preserved.

GAMs are prepared according to Examples 1 and 4. Access to the lesion site for implantation of the GAMs is through the exposed pia overlying the site of spinal cord transection. At intervals of 15, 30, 60 and 90 days post-lesion, animals are sacrificed and perfusion fixed as described in Example 4. Brains, spinal cords and dorsal root ganglia (DRG) are dissected and processed for histochemistry, also as described in Example 4.

Neuronal regeneration and tissue scarring in the spinal cord lesion are monitored as follows: Ipsilateral L4/5 DRG and pyramidal neurons in layers V and VI of the ipsilateral sensorimotor cortex are retrogradely labeled by injecting 2 $\mu$l of a 20% tracer solution (e.g., BDA, FDA) into the cord lesion site 2 days prior to sacrifice. The regenerative response of the gracile tract axons to injury is monitored qualitatively by a lysinated rhodamine dextran amine (LRDA) transganglionic labeling technique after sciatic nerve injection, and that of the corticospinal axons by labeling the pyramids on the ventral surface of the medulla oblongata. Axonal regeneration is detected by the presence of labeled axons crossing the lesion and invading the distal tracts in serial sections through the lesion.

The number of ascending axons regenerating through the lesion is determined as follows: Regenerated gracile tracts are retrogradely labeled following injection of 2 $\mu$l of 20% HRP (Sigma) into the lesion 24 hr prior to autopsy. HRP is injected at T1 (7 segments rostral to the lesion site); the number of retrogradely HRP-filled ipsilateral L4/5 dorsal root ganglia after this injection is scored by counting filled cells in serial sections through the ganglia. A quantitative measure of corticospinal tract regeneration is achieved by counting the numbers of HRP filled pyramidal cells in layers V and VI of the ipsilateral and contralateral sensorimotor neocortex after uptake at T13 (5 segments caudal to the lesion).

The above axon labeling methods are also used to examine re-innervation of targets both at the electron and light microscopic levels. In these studies HRP methods unequivocally identify regenerated DRG terminals in the ipsilateral gracile nucleus, and corticospinal terminations on motor horn cells below the lesion. Immunohistochemical analysis is essentially as described above in Example 4.

Example 8

Delivery and Expression of Neuronal Therapeutic Encoding Agents in Regenerating Rat Spinal Cord In this Example, a rat model system is presented for introducing experimental CNS lesions and using GAMs to deliver neuronal therapeutic encoding agents to modify scar deposition at the site of injury in the spinal cord model. The first order ascending sensory system of the gracile tract and the descending corticospinal system are used to model spinal cord regeneration using both short (2 weeks post-lesion) and long (10 weeks post-lesion) sampling times. Both tracts are found in the dorsal funiculi and at the level of T8 are easily lesioned surgically by contusion or section without disturbing the L4/5 root entry zone.

The injury is performed as described in Example 7.

GAMs are prepared according to Examples 1 and 4. Access to the lesion site for implantation of the GAMs is through the exposed pia overlying the site of spinal cord transection. At intervals of 2 and 10 weeks post-lesion, animals are sacrificed and perfusion fixed as described in Example 4. Brains, spinal cords and dorsal root ganglia (DRG) are dissected and processed for immunohistochemistry, also as described in Example 4.

Evaluation of scar and injury tissue is based on the presence and size of cystic cavitations at the lesion epicenter. Surviving axons are demonstrated using an anti-neurofilament antibody (i.e. RT97) as described in Example 4. To evaluate the number of dividing cells (i.e. proliferating oligodendrocytes) rats receive daily injections of BrdU (Sigma, 50 mg/Kg, i.p.) for 7 days beginning at day 21 after injury. For detection of BrdU, tissue sections are treated with 2N HCl for 1 hr., rinsed and then stained with an antibody against BrdU (Dako, Carpinteria, Calif.), using the protocol described in Example 4. Evaluation of the degree of myelination is performed by staining tissue sections with an antibody against myelin basic protein (MBP) using the protocol described in Example 4.

Example 9

Delivery and Expression of Neuronal Therapeutic Encoding Agents in Regenerating Rat Spinal Cord Using Mixed GAM In this Example, a rat model system is presented for introducing experimental CNS lesions and using a GAM to deliver neuronal therapeutic encoding genes to regenerating axons in the spinal cord. The GAM in this example also contains live cells (i.e., fibroblasts) and for this reason is called a mixed GAM. The GAMs are prepared, essentially as described in Example 1 but in addition, the GAMs are supplemented with mammalian, preferably autologous cells. These cells serve to modify healing time, synthesize matrix and may internalize DNA present in the GAM. The first order ascending sensory system of the gracile tract and the descending corticospinal system are used to model spinal cord regeneration using both short (2 weeks post-lesion) and long (10 weeks post-lesion) sampling times. Both tracts are found in the dorsal funiculi and at the level of T8 are easily lesioned surgically by contusion or section without disturbing the L4/5 root entry zone.

The injury is performed as described in example 7.

GAMs are prepared according to Examples 1 and 4 with the modifications described above. Access to the lesion site for implantation of the GAMs is through the exposed pia overlying the site of spinal cord transection. At intervals of 2 and 10 weeks post-lesion, animals are sacrificed and perfusion fixed as described in Example 4. Brains, spinal cords and dorsal root ganglia (DRG) are dissected and processed for immunohistochemistry, also as described in Example 4.

Evaluation of scar tissue, cell proliferation, axonal growth and myelination is performed as described in Example 8.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises an inducible promoter.

2. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a tissue specific promoter.

3. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a promoter selected from the group consisting of GAP43 promoter, GFAP promoter, neuron specific enolase promoter, FGF-receptor promoter, elastase I gene control region, immunoglobulin gene control region, alpha-1-antitrypsin gene control region, beta-globin gene control region, myelin basic protein gene control region, myosin light chain 2 gene control region, RSV promoter, vaccinia virus 7.5K promoter, SV40 promoter, HSV promoter, MLP adenovirus promoter, MMTV LTR promoter, CMV promoter, metallothionein promoter, a promoter having at least one cAMP response element, tie promoter, VCAM-1 promoter, alpha V-beta 3 integrin promoters, ICAM-3 promoter, CD44 promoter, CD40 promoter, notch 4 promoter, and an event type-specific promoter.

4. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a neuronal cell specific promoter.

5. The device of claim 4 wherein the promoter is selected from the group consisting of GAP43 promoter, FGF receptor promoter and neuron specific enolase promoter.

6. A device for promoting neuronal regeneration or survival, comprising a gene activated matrix comprising a biocompatible matrix and a complex comprising a receptor targeting ligand, a nucleic acid binding domain and a non-viral vector construct encoding a neurotrophic factor; wherein the vector construct comprises a promoter; and wherein the neurotrophic factor is selected from the group consisting of nerve growth factor (NGF), brain-derived neurotrophic factor (BDNF), cardiotrophin-1 (CT-1), choline acetyltransferase development factor (CDF), ciliary neurotrophic factor (CNTF), oncostatin M (OSM); glial cell-line-derived neurotrophic factor (GDNF), insulin, insulin-like growth factor-1 (IGF-1), IGF-2, interleukin-6 (IL-6), leukemia inhibitor factor (LIF), neurite promoting factor (NPF), neurotrophin-3 (NT-3), NT-4, platelet-derived growth factor (PDGF), protease nexin-1 (PN-1), S-100, transforming growth factor-β (TGF-β) and vasoactive intestinal peptide (VIP).

7. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a promoter and is non-covalently associated with the gene activated matrix.

8. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a promoter and is adsorbed to the gene activated matrix.

9. A device for promoting neuronal regeneration, comprising:
  a gene activated matrix comprising a biocompatible matrix and complex comprising a receptor targeting ligand, a nucleic acid binding domain and a non-viral vector construct encoding a neurotrophic factor; wherein the vector construct comprises a promoter and is absorbed to the gene activated matrix.

10. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter and is capable of inducing neuronal axonal generation or regeneration.

11. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the neurotrophic factor is capable of maintaining axonal generation or regeneration.

12. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is an implant for a neuronal injury site.

13. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is formed upon administration.

14. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is a composition selected from the group consisting of a solution, a paste, a suspension, a powder, a semisolid, an emulsion and a gel.

15. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is a paste.

16. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the receptor targeting ligand is capable of binding a neuronal cell surface receptor.

17. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the receptor targeting ligand is conjugated to the vector construct and is capable of binding a neuronal cell surface receptor.

18. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and said nucleic acid binding domain binds to a nucleic acid sequence that forms a portion of the vector construct.

19. A device for promoting neuronal regeneration, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and a conduit having a lumen.

20. The device of claim 19 wherein the conduit comprises the gene activated matrix.

21. The device of claim 19 wherein the lumen contains the gene activated matrix.

22. The device of claim 19 wherein the conduit comprises a bioabsorbable material.

23. The device of claim 22 wherein the bioabsorbable material comprises material selected from the group consisting of gene activated matrix, type I collagen, laminin, polyglycolic acid, glycolide trimethylene carbonate (GTMC), poly (L-lactide-co-6-caprolactone), glycoproteins, proteoglycans, heparan sulfate proteoglycan, nidogen, glycosarninoglycans, fibronectin, epidermal growth factor, fibroblast growth factor, nerve growth factor, cytokines, and DNA encoding growth factors and cytokines.

24. The device of claim 19 wherein the conduit comprises a non-bioabsorbable material.

25. The device of claim 24 wherein the non-bioabsorbable material is selected from the group consisting of polyamide, polyimide, polyurethane, segmented polyurethane, polycarbonate, and silicone.

26. The device of claim 24 wherein the non-bioabsorbable material comprises an etched microporous synthetic polymer surface.

27. The device of claim 19 wherein the conduit is tubular.

28. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises an inducible promoter.

29. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a tissue specific promoter.

30. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter selected from the group consisting of GAP43 promoter, GFAP promoter, neuron specific enolase promoter, FGF-receptor promoter, elastase I gene control region, immunoglobulin gene control region, alpha-1-antitrypsin gene control region, beta-globin gene control region, myelin basic protein gene control region, myosin light chain 2 gene control region, RSV promoter, vaccinia virus 7.5K promoter, SV40 promoter, HSV promoter, MLP adenovirus promoter, MMTV LTR promoter, CMV promoter, metallothionein promoter, a promoter having at least one cAMP response element, tie promoter, VCAM-1 promoter, alpha V-beta 3 integrin promoters, ICAM-3 promoter, CD44 promoter, CD40 promoter, notch 4 promoter, and an event type-specific promoter.

31. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a neuronal cell specific promoter.

32. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter and is non-covalently associated with the gene activated matrix.

33. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter and is adsorbed to the gene activated matrix.

34. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter and is absorbed in the gene activated matrix.

35. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter and is capable of inducing neuronal axonai generution or regeneration.

36. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the neurotrophic factor is capable of maintaining axonal generation or regeneration.

37. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is an implant for a neuronal injury site.

38. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is formed upon administration.

39. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is a composition selected from the group consisting of a solution, a paste, a suspension, a powder, a semisolid, an emulsion and a gel.

40. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the gene activated matrix is a paste.

41. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the receptor targeting ligand is capable of binding a neuronal cell surface receptor.

42. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and the receptor targeting ligand is conjugated to the vector construct and is capable of binding a neuronal cell surface receptor.

43. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and said nucleic acid binding domain binds to a nucleic acid sequence that forms a portion of the vector construct.

44. A device for promoting neuronal survival, comprising:
a gene activated matrix comprising a biocompatible matrix and complex comprising a receptor targeting ligand, a nucleic acid binding domain and a non-viral vector construct encoding a neurotrophic factor; wherein the vector construct comprises a promoter, and a conduit having a lumen.

* * * * *